United States Patent
Atwal et al.

(10) Patent No.: US 6,916,813 B2
(45) Date of Patent: Jul. 12, 2005

(54) (1-PHENYL-2-HETEOARYL)ETHYL-GUANIDINE COMPOUNDS AS INHIBITORS OF MITOCHONDRIAL F1F0 ATP HYDROLASE

(75) Inventors: Karnail S. Atwal, Pennington, NJ (US); Gary J. Grover, Stockton, NJ (US); Charles Z. Ding, Dallas, TX (US); Philip D. Stein, Pennington, NJ (US); John Lloyd, Yardley, PA (US); Saleem Ahmad, Wall, NJ (US); Lawrnce G. Hamann, Cherry Hill, NJ (US); David Green, Haverhill, MA (US); Francis N. Ferrara, Bedminster, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 22 days.

(21) Appl. No.: 10/315,818

(22) Filed: Dec. 10, 2002

(65) Prior Publication Data

US 2004/0039033 A1 Feb. 26, 2004

Related U.S. Application Data

(60) Provisional application No. 60/339,108, filed on Dec. 10, 2001.

(51) Int. Cl.$^7$ ............................ A01N 43/50; A61K 31/415
(52) U.S. Cl. .................. 514/235.8; 514/254.01; 514/314; 514/357; 514/361; 514/374; 514/383; 514/394; 514/397; 514/399; 544/139; 544/370; 546/164; 546/275.1; 548/127; 548/204; 548/262.8; 548/309.7; 548/314.7; 548/315.1; 548/315.4; 548/336.5
(58) Field of Search .............. 514/235.8, 254.01, 514/314, 357, 361, 374, 383, 394, 397, 399; 544/139, 370; 546/164, 275.1; 548/127, 204, 262.8, 309.7, 314.7, 315.1, 315.4, 336.5

(56) References Cited

U.S. PATENT DOCUMENTS

| | | | |
|---|---|---|---|
| 5,478,845 A | 12/1995 | Hansen et al. | 514/323 |
| 5,482,948 A | 1/1996 | Soyka et al. | 514/318 |
| 5,521,177 A | 5/1996 | Ries et al. | 514/370 |
| 6,162,790 A | 12/2000 | Bemis et al. | 514/18 |

FOREIGN PATENT DOCUMENTS

| | | |
|---|---|---|
| WO | WO 93/05026 | 3/1993 |
| WO | WO 96/23771 | 8/1996 |
| WO | WO 00/35449 | 6/2000 |
| WO | WO 00/43415 | 7/2000 |

OTHER PUBLICATIONS

Hawley's Condensed Chemical Dictionary, 12th ed., Richard J. Lewis, Sr. , © 1993 by Van Nostrand Reinhold, p. 594.*

Concise Encyclopedia Chemistry, edited by Drs. Hans–Dieter Jakubke and Hans Jeschkeit, © 1993 by Walter de Gruyter & Co p. 490.*

McGraw–Hill Dictionary of Chemical Terms, 3rd ed. edited by Sybil P. Parker, © 1984 McGraw–Hill, Inc., p. 200.*

Al–Dabbagh and Smith, "Species differences in oxidative drug metabolism: some basic considerations." Archives of toxicology, Supplement. Archiv fur Toxikologie. supplement, vol. 7, pp. 219–231 (1984).*

Hans Bundgaard, Design of Prodrugs, p. 1. © 1985 Elsevier Science Publishers.*

Richard B. Silverman, The Organic Chemistry of Drug Design and Drug Action, pp. 352–400. © 1992 Academic Press, Inc.*

Shimada et al., Chem. Pharm. Bull. vol. 32, No. 12, pp. 4893–4906 (1984).

* cited by examiner

Primary Examiner—James O. Wilson
Assistant Examiner—Zachary C. Tucker
(74) Attorney, Agent, or Firm—Laurelee A. Duncan

(57) ABSTRACT

Compounds having the formula (I), and pharmaceutically acceptable salts thereof,

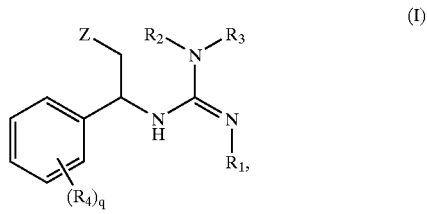

are useful for modulating mitochondrial $F_1F_0$ ATPase activity and treating ischemic conditions including myocardial infarction, congestive heart failure, and cardiac arrhythmias.

25 Claims, No Drawings

(1-PHENYL-2-HETEOARYL)ETHYL-GUANIDINE COMPOUNDS AS INHIBITORS OF MITOCHONDRIAL F1F0 ATP HYDROLASE

RELATED APPLICATIONS

This application claims the benefit of U.S. Provisional Application No. 60/339,108 filed Dec. 10, 2001.

FIELD OF THE INVENTION

This invention relates to compounds that inhibit nitochondrial $F_1F_0$ ATP hydrolase and are useful for treating ischemia-related diseases. The invention further pertains to methods of treating conditions associated with depleted levels of adenosine triphosphate (ATP) due to hydrolysis by mitochondrial $F_1F_0$ ATPase.

BACKGROUND OF THE INVENTION

Ischemic heart disease is a common and serious health problem. Every year, large numbers of patients die from ischemic heart disease and its complications. Many others experience acute myocardial infarcation, congestive heart failure, cardiac arrhythmias, or other disorders.

Myocardial ischemia exists when the heart tissue experiences a demand for oxygen and substrates that exceed the supply. Imbalances between oxygen supply and demand span a large range, and thus, there are various syndromes and biochemical pathways involved in the pathogenesis of ischemia, e.g., from low-grade to severe ischemic conditions. For example, chronic stable angina pectoris is a low-grade condition, in which the resting coronary blood flood may be normal but the blood flow reserve is insufficient to meet an increased energy demand. In more extreme situations, the ischemic muscle can develop an impaired contractile function and potential to generate arrhythmias. Major consequences of myocardial ischemia include mechanical and electrical dysfunction, muscle cell damage, and development of necrosis. Acute ischemic events may develop where there is coronary atherosclerosis. Ultimately, if the ischemia is sufficiently severe there will be an immediate reduction (or cessation) of contractile function in the heart.

The impairment of contractile function in ischemic muscle is associated with mitochondrial levels of adenosine triphosphate (ATP) and adenosine triphosphatases (ATPases). ATPases are enzymes that typically catalyze the hydrolysis of ATP, the main energy currency in cells, to adenosine monophosphate (AMP) or adenosine diphosphate (ADP), plus phosphate ions and energy. The contractile function of the heart is regulated by the transport of calcium, sodium, and potassium ions, which in turn is modulated by ATP and ATPases. More particularly, intracellular ATP is split by Na+,K+ATPase, an enzyme that is responsible for maintaining a gradient of sodium and potassium ions across the cell membrane. The splitting of ATP by Na+,K+ATPase releases the energy needed to transport K+ and Na$^+$ ions against concentration gradients. This enables the existence of a resting potential in the membrane (i.e, Na+ out, K+ in) which initiates the contractile response. Contraction is triggered by Na/Ca exchange and Ca$^{2+}$ transport, the energy for which is generated by the hydrolysis of ATP by Ca$^{2+}$ ATPase.

To maintain homeostasis, the cells' supply of ATP must be replenished as it is consumed (e.g., with muscle contraction). During the steady state, the rate of ATP synthesis needs to be closely matched to its rate of consumption. Arguably, the most important ATPase is the mitochondrial $F_1F_0$-ATPase. Unlike other ATPases which function typically to hydrolyze ATP and release energy, the $F_1F_0$-ATPase has both hydrolytic and synthetic states. As "ATP synthase", the mitochondrial $F_1F_0$-ATPase catalyzes the production of ATP via oxidative phosphorylation of ADP and $P_i$. Thus, $F_1F_0$-ATPase is responsible for producing the cell's main energy source, ATP. In normoxic conditions, mitochondrial $F_1F_0$-ATPase modulates this ATP production via its two units, the $F_1$ and $F_0$ complexes. $F_0$ is the inner membrane domain, and $F_1$ is a catalytic domain consisting of five subunits (($\alpha\beta\chi\delta\epsilon$—the catalytic site is on the $\beta$ unit), that protrude from the $F_0$ domain into the mitochondrial matrix. When sufficient levels of oxygen are present, electrons from ATPase substrates are transferred to oxygen, and protons are transported out of the mithcondrial matrix. This proton/electron transport creates an electrochemical proton gradient across the mitochondrial membrane and through the $F_0$ domain which drives the $F_1$ domain to synthesize ATP.

In ischemic conditions, however, this electrochemical gradient collapses, and $F_1F_0$-ATPase switches to its hydrolytic state. This hydrolysis of ATP seems to serve no useful purpose. Also, as $F_1F_0$-ATPase operates in its hydrolytic state there is a down-regulation of $F_1F_0$-ATP synthase. $F_1F_0$-ATP synthase activities in vesicles from ischemic muscle typically are substantially (up to ~50–80%) less than those of control muscle. A native peptide called $IF_1$ inhibitor protein (or $IF_1$) may be bound to the $F_1$ unit under ischemic conditions to inhibit the ATP hydrolase activity of the enzyme; however, $IF_1$ is highly pH dependent and in severe conditions can provide only a modicum of control. The conversion of $F_1F_0$-ATP synthase to $F_1F_0$-ATP hydrolase is reversible, as addition of substrate and oxygen to the mitochondria of ischemic muscle can reactivate the $F_1F_0$-ATPase and ATP levels to control levels.

As may be appreciated, in ischemic conditions the activity of $F_1F_0$-ATPase produces a futile cycling and waste of ATP. It is believed that this depletion of ATP and/or ATP synthase may suppress the Na+K+ pump to increase cardiac contractility, vasoconstriction, sensitivity to vasoactive agents, and arterial blood pressure. Several inhibitors of $F_1F_0$-ATPase have been described, including efrapeptin, oligomycin, autovertin B, and azide. Oligomycin targets $F_0$ and reportedly postpones cell injury by preserving ATP during ischemia. However, the only known inhibitors of $F_1F_0$-ATPase are large proteins or peptides which are not orally bioavailable.

The instant invention provides N-substituted-N'-(1-phenyl-2-heteraryl)ethyl-guanidine compounds including cyanoguanidine and benzoylguanidine compounds that are potent and selective inhibitors of $F_1F_0$-ATP hydrolase. The compounds of the present invention are useful in treating or preventing conditions associated with ischemia, particularly myocardial ischemia and associated conditions, such as muscle cell damage, necrosis, and cardiac arrhythmias. Also, in view of their inhibitory activity, the inventive compounds may be used to treat cancer and tumor growth. Cyanoguanidine based compounds for treating various other indications (e.g., diseases relating to the CNS-system, gastric secretion, inflammation, HIV, etc.) are disclosed in Shimada et al, *"Synthesis and Gastric Antisecretory Activity of N-Cyano-N'(phenyl-pyridinylmethyl)guanidine Derivatives,"* Chem. Pharm. Bull., Vol. 32(12), (1984), at pp. 4893–4906; WO 00/35449, *"N-Ureidoalkyl-Piperidines as Modulators of Chemokine Receptor Activity,"* to Du Pont Pharmaceuticals Co.; U.S. Pat. No. 5,478,845, *"Piperidine*

*Derivatives,*" issued Dec. 26, 1995 and assigned to Novo Nordisk A/S; WO 93/05026, "*Peptide Isoters Containing a Heterocycle as H.I.V. Inhibitors,*" to Smith-Kline Beecham Corp.; and WO 00/43415, "*Compounds which Inhibit Leukocyte Adhesion Mediated by VLA-*4," to Elan Pharmaceuticals, Inc. Cyano-guanidine compounds useful for lowering blood pressure or treating thrombotic or platelet aggregating conditions are disclosed in U.S. Pat. No. 5,521,177, U.S. Pat. No. 5,482,948, and WO 96/23771.

Each of the patents, patent applications and publications referred to in this application are incorporated herein by reference.

SUMMARY OF THE INVENTION

The invention is directed to compounds having the formula (I):

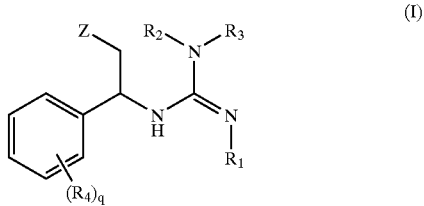

or a pharmaceutically-acceptable salt, hydrate, or prodrug thereof, wherein:

$R_1$ is cyano, —$SO_2R_8$, —$C(=O)R_9$, or heteroaryl;

$R_2$ is (i) independently hydrogen, alkyl, or substituted alkyl, or (ii) taken together with $R_3$ forms a heterocyclo;

$R_3$ is (i) independently alkyl, substituted alkyl, alkylthio, aminoalkyl, carbamyl, A-aryl, A-heterocyclo, A-heteroaryl, or A-cycloalkyl, or (ii) taken together with $R_2$ forms a heterocyclo;

Z is heteroaryl provided that when $R_1$ is cyano, Z is not 2-pyridinyl;

A is a bond, $C_{1-4}$alkylene, $C_{2-4}$alkenylene, substituted $C_{1-4}$alkylene, substituted $C_{2-4}$alkenylene, —C(=O)$NR_{19}$—, —$C_{1-4}$alkylene-C(=O)$NR_{19}$—, or substituted $C_{1-4}$alkylene-C(=O)$NR_{19}$—;

$R_4$ at each occurrence is selected independently of each other $R_4$ from the group consisting of halogen, alkyl, haloalkyl, nitro, cyano, haloalkoxy, $OR_{25}$, $SR_{25}$, $NR_{25}R_{26}$, $NR_{25}SO_2R_{27}$, $SO_2R_{27}$, $SO_2NR_{25}R_{26}$, $CO_2R_{26}$, $C(=O)R_{26}$, $C(=)NR_{25}R_{26}$, $OC(=O)R_{25}$, —OC(=O)$NR_{25}R_{26}$, $NR_{25}C(=O)R_{26}$, $NR_{25}CO_2R_{26}$, aryl, heteroaryl, heterocyclo and cycloalkyl;

$R_8$ is alkyl, substituted alkyl, aryl, or heteroaryl;

$R_9$ is —$NR_{10}R_{11}$, alkyl, substituted alkyl, alkoxy, alkylthio, cycloalkyl, aryl, heteroaryl, heterocycle, or —$CO_2R_{12}$;

$R_{10}$ and $R_{11}$, are (i) independently selected from hydrogen, alkyl, substituted alkyl, alkoxy, heterocyclo, cycloalkyl, aryl, and heteroaryl; or (ii) taken together form a heterocyclo or heteroaryl;

$R_{12}$ and $R_{19}$ are hydrogen or alkyl;

$R_{25}$ and $R_{26}$ are independently selected from hydrogen, alkyl, or substituted alkyl, or taken together form a heterocyclo or heteroaryl ring;

$R_{27}$ is alkyl or substituted alkyl, and q is 0, 1, 2, or 3.

Also included within the scope of the invention are pharmaceutical compositions comprising one or compounds of formula (I), and methods of treating ischemic conditions and/or conditions associated with depleted levels of adenosine triphosphate (ATP) and/or the activity of mitochondrial $F_1F_0$ ATPase. These methods comprise administering an effective amount of at least one compound of formula (I) to a patient in need thereof. Additionally, applicants have discovered that $F_1F_0$-ATP hydrolase can be selectively inhibited via use of a small organic molecule, i.e., a non-peptidic organic compound having less than 1000 molecular weight, and this invention is also claimed herein.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "substituted alkyl" refers to an alkyl group as defined above having one, two, three, or four substituents selected from the group consisting of halogen, trifluoromethyl, alkenyl, alkynyl, nitro, cyano, keto (=O), $OR_a$, $SR_a$, $NR_aR_b$, $NR_aSO_2$, $NR_aSO_2R_c$, $SO_2R_c$, $SO_2NR_aR_b$, $CO_2R_a$, $C(=O)R_a$, $C(=O)NR_aR_b$, $OC(=O)R_a$, —OC(=O)$NR_aR_b$, $NR_aC(=O)R_b$, $NR_aCO_2R_b$, =N—OH, =N—O-alkyl, aryl, heteroaryl, heterocyclo and cycloalkyl, wherein $R_a$ and $R_b$ are selected from hydrogen, alkyl, alkenyl, cycloalkyl, heterocyclo, aryl, and heteroaryl, and $R_c$ is selected from hydrogen, alkyl, cycloalkyl, heterocyclo aryl and heteroaryl. When a substituted alkyl includes an aryl, heterocyclo, heteroaryl, or cycloalkyl substituent, said ringed systems are as defined below and thus may in turn have zero to four substituents (preferably 0–2 substituents), also as defined below. When either $R_a$, $R_b$ or $R_c$ is an alkyl, said alkyl may optionally be substituted with 1–2 of halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl), $SO_2$(alkyl), $SO_2NH_2$, $SO_2$NH(alkyl), $CO_2$H, $CO_2$(alkyl), C(=O)H, C(=O)alkyl, C(=O)$NH_2$, C(=O)NH (alkyl), C(=O)N(alkyl)$_2$, OC(=O)alkyl, —OC(=O)$NH_2$, —OC(=O)NH(alkyl), NHC(=O)alkyl, and/or $NHCO_2$ (alkyl). "Alkyl" when used in conjunction with another group such as in arylalkyl refers to a substituted alkyl in which at least one of the substituents is the specifically-named group. For example, the term arylalkyl includes benzyl, or any other straight or branched chain alkyl having at least one aryl group attached at any point of the alkyl chain. As a further example, the term carbamylalkyl includes the group —(CH$_2$)$_n$—NH—C(=O)alkyl, wherein n is 1 to 12.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alknyl groups, respectively, as defined above.

When reference is made to a substituted alkylene, alkenylene, or alkynylene group, these groups are substituted with one to four substitutents as defined above for alkyl groups. A substituted alkylene, alkenylene, or alkynylene may have a ringed substituent attached in a spiro fashion as in

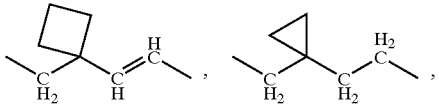

and so forth.

The term "alkoxy" refers to an alkyl or substituted alkyl group as defined above having one, two or three oxygen atoms (—O—) in the alkyl chain. For example, the term "alkoxy" includes the groups —O—$C_{1-12}$alkyl, —$C_{1-6}$alkylene-O—$C_{1-6}$alkyl, —$C_{1-4}$alkylene-O-phenyl, and so forth.

The term "thioalkyl" or "alkylthio" refers to an alkyl or substituted alkyl group as defined above having one or more sulfur (—S—) atoms in the alkyl chain. For example, the term "thioalkyl" or "alkylthio" includes the groups —$(CH_2)_n$—S—$CH_2$aryl, —$(CH_2)_n$—S—aryl, etc. etc.

The term "aminoalkyl" refers to an alkyl or substituted alkyl group as defined above having one or more nitrogen (—NR'—) atoms in the alkyl chain. For example, the term "aminoalkyl" includes the groups —NR'—$C_{1-12}$alkyl and —$CH_2$—NR'-aryl, etc. (where R' is hydrogen, alkyl or substituted alkyl as defined above.) "Amino" refers to the group —$NH_2$.

When a subscript is used as in $C_{1-8}$alkyl, the subscript refers to the number of carbon atoms the group may contin. Zero when used in a subscript denotes a bond, e.g., $C_{0-4}$alkyl refers to a bond or an alkyl of 1 to 4 carbon atoms. When used with alkoxy, thioalkyl or aminoalkyl, a subscript refers to the number of carbon atoms that the group may contain in addition to heteroatoms. Thus, for example, monovalent. $C_{1-2}$aminoalkyl includes the groups —$CH_2$—$NH_2$, —NH—$CH_3$, —$(CH_2)_2$—$NH_2$, —NH—$CH_2$—$CH_3$, —$CH_2$—$NH_2$—$CH_3$, and —N—$(CH_3)_2$. A lower aminoalkyl comprises an aminoalkyl having one to four carbon atoms.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. For example, a monovalent alkoxy includes groups such as —O—$C_{1-12}$alkyl, —$C_{1-6}$alkylene-O—$C_{1-6}$alkyl, etc., whereas a bivalent alkoxy includes groups such as —O—$C_{1-2}$alkylene-, —$C_{1-6}$alkylene-O—$C_{1-6}$alkylene-, etc.

The term "acyl" refers to a carbonyl

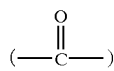

linked to an organic group i.e.,

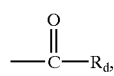

wherein $R_d$ may be selected from alkyl, alkenyl, substituted alkyl, substituted alkenyl, aryl, heterocyclo, cycloalkyl, or heteroaryl, as defined herein.

The term "alkoxycarbonyl" refers to a group having a carboxy or ester group

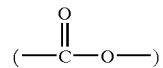

linked to an organic radical, i.e.,

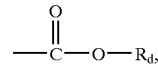

wherein $R_d$ is as defined above for acyl.

The term "carbamyl" refers to a functional group in which a nitrogen atom is directly bonded to a carbonyl, i.e., as in —$NR_eC(=O)R_f$ or —$C(=O)NR_eR_f$, wherein $R_e$ and $R_f$ can be hydrogen, alkyl, substituted alkyl, alkenyl, substituted alkenyl, alkoxy, cycloalkyl, aryl, heterocyclo, or heteroaryl, or they may join to form a ring.

The term "sulfonyl" refers to a sulphoxide group (i.e., —$S(O)_{1-2}$) linked to an organic radical $R_c$, as defined above.

The term "sulfonamide" or "sulfonamido" refers to the group —$S(O)_2NR_eR_f$, wherein $R_e$ and $R_f$ are as defined above. Preferably when one of $R_e$ and $R_f$ is optionally substituted heteroaryl or heterocycle (as defined below), the other of $R_e$ and $R_f$ is hydrogen or alkyl.

The term "cycloalkyl" refers to fully saturated and partially unsaturated hydrocarbon rings of 3 to 9, preferably 3 to 7 carbon atoms. The term "cycloalkyl" includes such rings having zero to four substituents (preferably 0–2 substituents), selected from the group consisting of halogen, alkyl, substituted alkyl (e.g., trifluoromethyl), alkenyl, substituted alkenyl, alkynyl, nitro, cyano, keto, $OR_d$, $SR_d$ $NR_dR_e$ $NR_cSO_2$, $NR_cSO_2R_e$, C(=O)H, acyl, —$CO_2H$, alkoxycarbonyl, carbamyl, sulfonyl, sulfonamide, —OC(=O)$R_d$, =N—OH, =N—O-alkyl, aryl, heteroaryl, heterocyclo, a 4 to 7 membered carbocyclic ring, and a five or six membered ketal, e.g., 1,3-dioxolane or 1,3-dioxane, wherein $R_c$, $R_d$ and $R_e$ are defined as above. The term "cycloalkyl" also includes such rings having a phenyl ring fused thereto or having a carbon-carbon bridge of 3 to 4 carbon atoms. Additionally, when a cycloalkyl is substituted with a further ring, i.e., aryl, arylalkyl, heteroaryl, heteroarylalkyl, heterocyclo, heterocycloalkyl, cycloalkylalkyl, or a further cycloalkyl ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), N(alkyl)$_2$, $NHSO_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and $NHCO_2$(alkyl).

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl, 2-naphthyl, and anthracenyl, with phenyl being preferred. The term "aryl" includes such rings having zero to four substituents (preferably 0–2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_c$, $C(=O)H$, acyl, $—CO_2H$, alkoxycarbonyl, carbamyl, sulfonyl, sulfonamide, $—OC(=O)R_d$, heteroaryl, heterocyclo, cycloalkyl, phenyl, benzyl, napthyl, including phenylethyl, phenyloxy, and phenylthio, wherein $R_c$, $R_d$ and $R_e$ are defined as above. Additionally, two substituents attached to an aryl, particularly a phenyl group, may join to form a further ring such as a fused or spiro-ring, e.g., cyclopentyl or cyclohexyl or fused heterocycle or heteroaryl. When an aryl is substituted with a further ring, such ring in turn may be substituted with one to two of $CO_{4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), $N(alkyl)_2$, $NHSO_2$, $NHSO_2$(alkyl), $SO_2$(alkyl), $SO_2NH_2$, $SO_2NH$(alkyl), $CO_2H$, $CO_2$(alkyl), $C(=O)H$, $C(=O)$alkyl, $C(=O)NH_2$, $C(=O)NH$(alkyl), $C(=O)N(alkyl)_2$, $OC(=O)$alkyl, $—OC(=O)NH_2$, $—OC(=O)NH$(alkyl), $NHC(=O)$alkyl, and $NHCO_2$(alkyl).

The term "heterocyclo" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom selected from O, S and N. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to four substituents (preferably 0–2 substituents), selected from the group consisting of halo, alkyl, substituted alkyl (e.g., trifluoromethyl), alkenyl, substituted alkenyl, alkynyl, nitro, cyano, keto, $OR_d$, $SR_d$, $NR_dR_e$, $NR_dSO_2$, $NR_dSO_2R_c$, $SO_2R_d$, $C(=O)H$, acyl, $—CO_2H$, alkoxycarbonyl, carbamyl, sulfonyl, sulfonamide, $—OC(=O)R_d$, =N—OH, =N—O-alkyl, aryl, heteroaryl, cycloalkyl, a five or six membered ketal, e.g., 1,3-dioxolane or 1,3-dioxane, or a monocyclic 4 to 7 membered non-aromatic ring having one to four heteroatoms, wherein $R_c$, $R_d$ and $R_e$ are defined as above. The term "heterocyclo" also includes such rings having a phenyl ring fused thereto or having a carbon-carbon bridge of 3 to 4 carbon atoms. Additionally, when a heterocyclo is substituted with a further ring, i.e., aryl, arylalkyl, heteroaryl, heteroarylalkyl, cycloalkyl, cycloalkylalkyl, heterocycloalkyl, or a further heterocyclo ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), NH2, NH(alkyl), N(alkyl)2, NHSO2, NHSO2(alkyl), S02(alkyl), $SO_2NH_2$, $SO_2NH$(alkyl), $CO_2H$, $CO_2$(alkyl), $C(=O)H$, $C(=O)$alkyl, $C(=O)NH_2$, $C(=O)NH$(alkyl), $C(=O)N(alkyl)_2$, $OC(=O)$alkyl, $—OC(=O)NH_2$, $—OC(=O)NH$(alkyl), $NHC(=O)$alkyl, and $NHCO_2$(alkyl).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom selected from O, S and N in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero to four substituents (preferably 0–2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2$, $NR_dSO_2R_c$, $SO_2R_d$, $C(=O)H$, acyl, $—CO_2H$, alkoxycarbonyl, carbamyl, sulfonyl, sulfonamide, $—OC(=O)R_d$, heterocyclo, cycloalkyl, aryl, or a monocyclic 4 to 7 membered aromatic ring having one to four heteroatoms, including phenylethyl, phenyloxy, and phenylthio, wherein $R_c$, $R_d$ and $R_e$ are defined as above. Additionally, when a heteroaryl is substituted with a further ring, i.e., aryl, arylalkyl, heterocyclo, heterocycloalkyl, cycloalkyl, cycloalkylalkyl, heteroarylalkyl, or a further heteroaryl ring, such ring in turn may be substituted with one to two of $C_{0-4}$alkyl optionally substituted with halogen, trifluoromethyl, alkenyl, alkynyl, nitro, cyano, keto (=O), OH, O(alkyl), phenyloxy, benzyloxy, SH, S(alkyl), $NH_2$, NH(alkyl), $N(alkyl)_2$, $NHSO_2$, $NHSO_2$(alkyl),n $SO_2$(alkyl), $SO_2NH_2$, $SO_2NH$(alkyl), $CO_2H$, $CO_2$(alkyl), $C(=O)H$, $C(=O)$alkyl, $C(=O)NH_2$, $C(=O)NH$(alkyl), $C(=O)N(alkyl)_2$, $OC(=O)$alkyl, $—OC(=O)NH_2$, $—OC(=O)NH$(alkyl), $NHC(=O)$alkyl, and $NHCO_2$(alkyl).

Exemplary monocyclic heteroaryl groups include pyrrolyl, pyrazolyl, pyrazolinyl, imidazolyl, oxazolyl, isoxazolyl, thiazolyl (i.e., 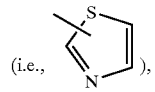), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

Throughout the specification, groups and substituents thereof may be chosen by one skilled in the field to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the formula I, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asynmmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

In addition, compounds of the formulas I may have prodrug forms. Any compound that will be converted in vivo to provide the bioactive agent (i.e., a compound of formula I) is a prodrug within the scope and spirit of the invention.

For example, pro-drug compounds of the formulas I may be carboxylate ester moieties. A carboxylate ester may be conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, p. 309–396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, Vol. 8, p. 1–38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

Preferred Compounds

Preferred compounds of the present invention are those having the following formula, or salts, hydrates, and pro-drugs thereof,

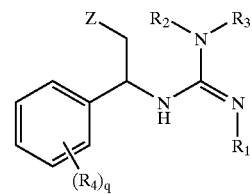

in which:

Z is triazolyl optionally substituted with one to two $R_7$ or imidazolyl optionally substituted with one to two $R_7$ and/or having fused thereto a benzene ring in turn optionally substituted with one to two $R_7$;

$R_1$ is cyano or —C(=O)$R_9$;

$R_2$ is hydrogen, alkyl, or benzyl;

$R_3$ is aryl or arylalkyl optionally substituted with alkyl, halogen, trifluoromethyl, OCF$_3$, cyano, nitro, amino, hydroxy, or methoxy;

$R_4$ is halogen, alkyl, trifluoromethyl, or OCF$_3$;

$R_7$ is alkyl, carbamyl or carbamyl$C_{1-4}$alkyl;

$R_9$ is —$NR_{10}R_{11}$, alkyl, substituted alkyl, alkoxy, alkylthio, cycloalkyl, aryl, heteroaryl, heterocycle, or —$CO_2R_{12}$;

$R_{10}$ and $R_{11}$ are (i) independently selected from hydrogen, alkyl, substituted alkyl, alkoxy, heterocyclo, cycloalkyl, aryl, and heteroaryl; or (ii) taken together form a heterocyclo or heteroaryl;

$R_{12}$ is hydrogen or alkyl; and q is 0, 1, 2, or 3.

Further preferred are compounds having the following formula, or salts, hydrates, or prodrugs thereof,

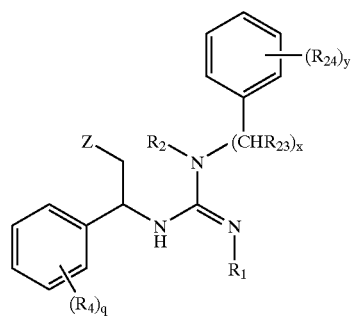

in which

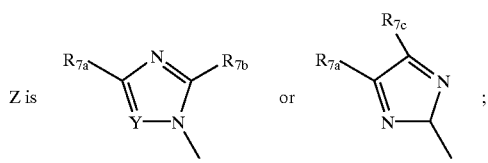

Y is N or $CR_{7c}$;

$R_1$ is cyano or —$C(=O)R_9$;

$R_2$ is hydrogen or $C_{1-4}$alkyl;

$R_4$ is halogen, $C_{1-4}$alkyl, trifluoromethyl, or $OCF_3$;

$R_{7a}$, $R_{7b}$ and $R_{7c}$ are alkyl, carbamyl or carbamyl$C_{1-4}$alkyl, or $R_{7a}$ and $R_{7c}$ join to form an optionally substituted fused phenyl ring;

$R_9$ is —$NR_{10}R_{11}$, alkyl, substituted alkyl, alkoxy, alkylthio, cycloalkyl, aryl, heteroaryl, heterocycle, or —$CO_2R_{12}$;

$R_{10}$ and $R_{11}$ are (i) independently selected from hydrogen, alkyl, substituted alkyl, alkoxy, heterocyclo, cycloalkyl, aryl, and heteroaryl; or (ii) taken together form a heterocyclo or heteroaryl;

$R_{12}$ is hydrogen or alkyl;

$R_{23}$ is hydrogen, alkyl, hydroxyalkyl, or phenyl;

$R_{24}$ is alkyl, halogen, trifluoromethyl, cyano, halogen, hydroxy, $OCF_3$, methoxy, phenyloxy, benzyloxy, cyano, or acyl, or two $R_{24}$ groups join to form a fused cycloalkyl or benzene ring;

q is 1 or 2;

x is 0, 1, or 2; and y is 0, 1, 2, or 3.

More preferred are compounds having the following formula, or salts, hydrates, or prodrugs thereof,

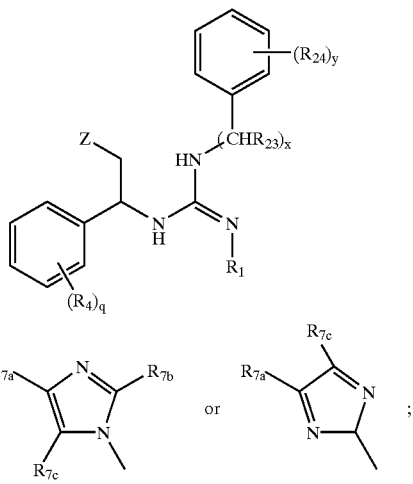

$R_1$ is cyano or —$C(=O)R_9$;

$R_4$ is halogen, $C_{1-4}$alkyl, trifluoromethyl, or $OCF_3$;

$R_7$ and $R_{7c}$ join to form a fused benzene ring optionally substituted with $C_{1-4}$alkyl or —$(CH_2)_{1-2}$—$NHC(=O)C_{1-4}$alkyl, $R_{7b}$ is hydrogen, $C_{1-4}$alkyl, or —$(CH_2)_{1-2}$—$NHC(=O)C_{1-4}$alkyl;

$R_9$ is a) —$NR_{10}R_{11}$;

b) $C_{1-8}$alkyl optionally substituted with one to two of:
  i) $SR_{13}$, $OR_{13}$, $NR_{13a}R_{13b}$, halogen, trifluoromethyl, $CO_2R_{13a}$, and $C(=O)NR_{13a}R_{13b}$;
  ii) cycloalkyl optionally substituted with one to two of $C(=O)H$, $C_{1-4}$acyl, alkenyl, carbamyl, and/or phenyl in turn optionally substituted with halogen;
  iii) phenyl or napthyl optionally substituted with one to two of halogen, nitro, amino, alkyl, hydroxy, $C_{1-4}$alkoxy, or having fused thereto a five or six membered heterocyclo;
  iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;

c) $C_{1-4}$alkoxy;

d) $C_{1-4}$alkylthio;

e) $CO_2$alkyl;

f) 3 to 6 membered cycloalkyl optionally having up to four substituents selected from alkyl, halogen, cyano, alkenyl, acyl, alkylthio, carbamyl, and/or phenyl in turn optionally substituted with halogen; or having an aryl fused thereto;

g) phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, $NH(C_{1-4}$alkyl), $N(C_{1-4}$alkyl)$_2$, NHC(=O)alkyl, C(=O)alkyl, and/or $C_{1-4}$alkyl in turn optionally substituted with one to three of trifluoromethyl, hydroxy, cyano, phenyl, pyridinyl; and/or a five or six membered heteroaryl or heterocyle in turn optionally substituted with keto or having a benzene ring fused thereto;

h) pyridinyl, thiazolyl, furanyl, thiophenyl, and pyrrolyl optionally substituted with one to two of halogen, alkyl, and phenyl in turn optionally substituted with halogen or trifluoromethyl;

$R_{10}$ is hydrogen, alkyl, or alkoxy;

$R_{11}$ is alkyl, substituted alkyl, alkoxy, heterocyclo, cycloalkyl, aryl, or heteroaryl; or $R_{10}$ and $R_{11}$, taken together form a heterocyclo or heteroaryl;

$R_{23}$ is hydrogen, alkyl, hydroxyalkyl, or phenyl;

$R_{24}$ is alkyl, halogen, trifluoromethyl, cyano, halogen, hydroxy, $OCF_3$, methoxy, phenyloxy, benzyloxy, cyano, or acyl, or two $R_{24}$ groups join to form a fused cycloalkyl or benzene ring;

q is 0, 1, or 2;

x is 0 or 1; and y is 0, 1, or 2.

Most preferred are compounds as immediately defined above wherein $R_1$ is cyano or —C(=O)$R_9$; $R_9$ is optionally substituted phenyl or phenyl $C_{1-4}$alkyl; x is 0 or 1; and q and y are 1 or 2.

Utility

The compounds of this invention by inhibiting $F_1F_0$-ATPase may be used to help conserve ATP under conditions of oxygen deprivation. Thus, the compounds may be useful in treating or preventing any condition associated with depleted levels of ATP and/or tissue ischeria (from mild to acute or severe). As used herein with reference to the utilities described below, the terms "treating" or "treatment" encompass both responsive and prophylaxis measures designed to inhibit or delay the onset of the disease or disorder, or to alleviate, ameliorate, lessen, or cure the disease or disorder and/or its symptoms.

In view of their $F_1F_0$-ATPase inhibitory activity, the inventive compounds are useful in treating cardiovascular diseases including, without limitation, congestive heart failure, cardiac arrhythmias, unstable angina, and high blood pressure. The compounds also are useful to treat ischemia, including ischemia resulting from vascular occlusion, cerebral infarction, stroke and related cerebral vascular diseases (including cerebrovascular accident and transient ischemic attack), and accurate coronary syndromes such as myocardial infarction, coronary artery disease, unstable angina, and non-Q wave MI.

Additionally, the compounds are useful in treating or preventing symptoms or consequences occurring from thrombosis and/or the formation of atherosclerotic plaques, atherosclerosis, peripheral arterial disease, coagulation syndromes, and intermittent claudication. The compounds may be used to treat thrombotic or thromboembolic conditions such as thromboembolic stroke (including that resulting from atrial fibrillation 10 or from ventricular mural thrombus); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, hormome replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregancy including fetal loss; thromboembolic consequenses of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation); coagulation syndromes; vascular remodeling atherosclerosis, restenosis and systemic infection; prevention of metastesis and tumor implantation; diabetic complications including retinopathy, nephropathy and neuropathy; inflammation; Kasabach-Merritt syndrome; atrial fibrillation; ventricular enlargement (including dilated cardiac myopathy and heart failure); restenosis (e.g., following arterial injury-induced either endogenously or exogenously). Compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation. Additionally, the compounds may be used for preservation of tissue as related to organ transplantation.

The inventive compounds also are useful in treating diseases or disorders in other tissues or muscles that are associated with ischemic conditions. For example, the compounds may be used to treat muscle cell damage and necrosis.

Additionally, the inventive compounds may be useful as anti-cancer and/or anti-tumor agents. It is reported that inhibitors of mitochondrial $FIF_0$-ATPase selectively kill metabolically active tumor cells that do not exhibit the Warburg effect, i.e., cells that do not maintain a high level of anaerobic carbon metabolism even in the presence of oxygen. See Salomon et al., "*Understanding and Exploiting the Mechanistic Basis for Selecivity of Polyketide Inhibitors of $F_1F_0$-ATPase,*" Proc. Natl. Acad. Sci. Vol. 97 (26) (2000), at pp. 14766–14771. Accordingly, the compounds of the present invention are useful in treating tumor growth, as an adjunct to chemotherapy, and for treating cancer, more particularly, cancer of the lung, prostate, colon, breast, ovaries, and bone.

The inventive compounds may also be used in combination with other $F_1F_0$-ATPase inhibitors such as efrapeptin, oligomycin, autovertin B, and azide, and/or in combination with other cardiovascular drugs. Additionally, the compounds may be used in combination with other therapeutic agents such as potassium channel openers, calcium channel blockers, sodium hydrogen exchanger inhibitors, anti-arrhythmic agents, thrombin inhibitors, platelet aggregation inhibitors or anti-platelet agents, fibrinogen antatagonists, diuretics, anti-hypertensive agents, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-oxidant agents; angiogenesis modulators; anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

For example, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include:

- anti-arrhythmic agents including Class I agents (such as propafenone); Class II agents (propranolol); Class III agents (such as sotalol, dofetilide, amiodarone, azimilide and ibutilide); Class IV agents (such as ditiazem and verapamil); K$^+$ channel openers such as IAch inhibitors, and IKur inhibitors (e.g., compounds such as those disclosed in U.S. application Ser. No. 09/729,731, filed Dec. 5, 2000;
- alpha- or beta- adrenergic blockers (such as propranolol, nadolol and carvedilol), or -β-adrenergic agonists such as albuterol, terbutaline, formoterol, salmeterol, bitolterol, pilbuterol, and/or fenoterol;
- angiotensin-II receptor antagonists (e.g., irbesartan, losartan or valsartan);
- anticholinergics such as ipratropium bromide;
- anti-diabetic agents such as biguamides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguamide/ glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;
- anti-depressant or anti-anxiety agents such as nefazodone, sertraline, diazepam, lorazepam, buspirone, and hydroxyzine pamoate;
- anti-diabetic agents such as biguamides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguamide/ glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors;
- anti-hypertensive agents such as angiotensin-converting enzyme (ACE) inhibitors (e.g., captopril, lisinopril, zofenopril, ramipril, fosinopril, enalapril, ceranopril, cilazopril, delapril, pentopril, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors;
- anti-inflammatory agents such as cromolyn, nedocromil, theophyline, zileuton, zafirlukast, montelcukast and/or pranleukast or corticosteroids including beclomethasone, triamcinolone, budesonide, fluticasone, flumisolide or dexamethasone; prednisono; daxamethasone etanercept, protien tyrosine kinase (PTK) inhibitors; cyclooxygenase inhibitors (including NSAIDs, and COX-1 and/or COX-2 inhibitors); aspirin; or indomethacin; lipoxygenase inhibitors; chemokine receptor modulators (including CCR1, CCR2, CCR3, CXCR2 receptor antagonists); secretory and cytoslic phospholipase A2 inhibitors; VLA4 atitagonists; cytokine modulators (e.g. TNF-alpha converting enzyme (TACE) inhibitors, Interleukin-1 converting enzyme (ICE) inhibitors, Interleukin-1 receptor antagonists);
- angiogenesis modulators such as endostatin;
- anti-oxidant agents and/or lipid peroxidation inhibitors such as probucol, BO-653, Vitamin A, Vitamin E, AGI-1067;
- anti-platelet agents such as GPIIb/GPIIIa blockers, (e.g., abciximab, eptifibatide, tirofiban); P2Y$_{12}$ antagonists (e.g., clopidogrel, ticlopidine, CS-747); or thromboxane receptor antagonists (e.g., ifetroban);
- anti-osteoporosis agents including alendronate and raloxifene.
- anti-obesity agents including orlistat and aP2 inhibitors (such as those disclosed in U.S. Ser. No. 09/519,079 filed Mar. 6, 2000);
- anti-proliferative agents for use in combination with the compounds of the present invention include cyclosporin A, paclitaxel, FK 506, and adriamycin;
- anti-ulcer and gastroesophageal reflux disease agents including famotidine, ranitidine, and omeprazole;
- sodium hydrogen exchanger-1 (NHE-1) inhibitors such as cariporide;
- calcium channel blocking agents such as verapamil, nifedipine, diltiazem, amlodipine and mybefradil;
- cardiac glycosides such as digitalis and ouabain;
- diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride;
- hormone replacement therapies including estrogen (e.g., congugated estrogens) and estradiol;
- lipid profile modulators including HMG-CoA reductase inhibitors (e.g., pravastatin, simvastatin, atorvastatin, fluvastatin, cerivastatin, AZ4522, itavastatin [Nissan/ Kowa]), ZD-4522 (a.k.a. rosuvastatin, or atavastatin or visastatin)); squalene synthetase inhibitors; fibrates; bile acid sequestrants (such as questran); ACAT1 inhibitors; ACAT2 inhibitors; dual ACAT1/2 inhibitors; MTP inhibitors; cholesterol absorption inhibitors; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists;
- mineralocorticoid receptor antagonists such as spironolactone and eplirinone.
- microsomal triglyceride transport protein inhibitors (such as disclosed in U.S. Pat. Nos. 5,739,135, 5,712,279 and 5,760,246);
- phosphodiesterase (PDE) inhibitors including dipyridamole, cilostazol, or sildenafil, or PDE inhibitors in combination with aspirin, ifetroban, picotamide, ketanserin, clopidogrel, and/or thromboxane receptor antagonists or thromboxane A synthetase inhibitors (such as picotamide);

serotonin-2-receptor antagonists (such as ketanserin), fibrinogen receptor antagonists, and thrombolytic agents, such as tissue plasminogen activator (natural or recombinant), streptokinase, reteplase, activase, lanoteplase, urokinase, prourokinase, tenecteplase (TNK), lanoteplase (nPA), anisolated, streptokinase plasminogen activator complex (ASPAC), factor VIIa inhibitors, factor Xa inhibitors, thrombin inhibitors (such as hirudin and argatroban), animal salivary gland plasminogen activators, PAI-1 inhibitors such as XR-330 and T-686, and inhibitors of α-2-antiplasmin such as anti-α-2-antiplasmin antibody, prostacyclin mimetics.

The inventive compounds may also be useful in combination with other anticancer strategies and chemotherapies such as taxol and/or cisplatin. The compounds may be used in conjunction with anti-tumor agents such as paclitaxel, adriamycin, epithilones, cisplatin, and carboplatin.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to allow for increased efficacy and/or reduced doses of any of the above agents and therefore minimize potential hemorrhagic side-effects.

The compounds of formula I may be administered by any means suitable for the condition to be treated. Systematic treatment is typically preferred for cancerous conditions, although other modes of delivery are contemplated. The compounds may be delivered orally, such as in the form of tablets, capsules, granules, powders, or liquid formulations including syrups; sublingually; bucally; transdermally; parenterally, such as by subcutaneous, intravenous, intramuscular or intrasternal injection or infusion (e.g., as sterile injectable aqueous or non-aqueous solutions or suspensions); nasally such as by inhalation spray; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. An exemplary effective amount of compounds of formula I may be within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

Assay

Mitochondria were isolated from bovine hearts and purified through a Percoll gradient, sonicated to generate sub mitochondrial particles (SMP), centrifuged, and stored at −80° C. See Gasnier F. et al, *"Use of Percoll Gradients for Isolation of Human Placenta Mitochondria Suitable for Investigating Outer Membrane Proteins,"* Anal. Biochem., Vol 212(1) (1993) at pp. 173–178; and Matsuno-Yagi A et al, *"Studies on the Mechanism of Oxidative Phosphorylation: Effects of Specific $F_0$ Modifiers on Ligand-Induced Conformation Changes of $F_1$,"* Proc. Nat'l Acad. Sci. USA, Vol. 82(22) (1985), at pp. 7550–7554.) ATP hydrolyase activity was determined using SMP and the well-characterized coupled enzyme system in which ATP hydrolysis and subsequent ADP generation is coupled through pyruvate kinase and lactate dehydrogenase to NAD+generation which was monitored by a decrease in absorbance at 340 nm (see Pullman, M. E. et al, *"Partial Resolution of the Enzymes Catalyzing Oxidative Phosphorylation,"* J. Biol. Chem. Vol.

235 (1960), at pp. 3322–3329.) Similarly, compound effects on ATP synthase activity were determined using SMP in the well-characterized coupled enzyme assay in which ATP generation is coupled to NADPH synthesis through the hexokinase and glucose-6-phosphate dehydrogenase pathway (Cross & Kohlbrenner, "*The Mode of Inhibition of Oxidative Phosphorylation by Efrapeptin (A23871). Evidence for an Alternating Site Mechanism for ATP Synthesis,*" *J. Biol. Chem.*, Vol. 253 (1978) at pp. 4865–4873.) NADPH increase was monitored spectrophotometrically by an increase in absorbance at 340 nm. Compounds were dissolved in 100% dimethyl sulfoxide and tested at increasing concentrations for enzyme inhibition. The concentration of compound causing 50% inhibition of the enzyme ($IC_{50}$) was calculated after the data was fitted using the Levenburg Marquardt algorithm and Microsoft Excel.

Compounds of formula (I), and more particularly, the compounds of Examples 1 through 494 hereof, were tested in this assay and found to have a measurable level of activity for inhibiting $F_1F_0$-ATP hydrolase. Each of the compounds of Examples 1–494 is a non-peptidic small organic compound with less than 1000 molecular weight, with preferred compounds having less than 750 molecular weight.

Abbreviations

The following abbreviations are employed in the Examples and elsewhere herein:
Ph=phenyl
Bn=benzyl
Me=methyl
Et=ethyl
MeOH=methanol
EtOH=ethanol
Pr=propyl
Bu=butyl
AcOH=acetic acid
DBU=1,8-diazabicyclo[5,4,0]undec-7-ene
DIP-Cl=B-chlorodiisopinocampheylborane
DMF=N,N-dimethylformamide
DPPA=Diphenylphosphoryl azide
EDC=N-(3-dimethylaminopropyl)-N'-ethylcarbodiimide
EtOAc=ethyl acetate
$NaBH_4$=sodium borohydride
$NaHCO_3$=sodium bicarbonate
KCNS=potassium isothiocyanate
Pd/C=palladium on carbon
$PtO_2$=platinum oxide
$Ph_3P$=triphenylphosphine
TEA=triethylamine or $Et_3N$
THF=tetrahydrofuran
TFA=trifluoroacetic acid
min=minute(s)
h or hr=hour(s)
L=liter
mL=milliliter
µL=microliter
g=gram(s)
mg=milligram(s)
mol=mole(s)
mmol=millimole(s)
meq=milliequivalent
rt=room temperature
sat or sat'd=saturated
aq.=aqueous
TLC=thin layer chromatography
LC/MS=high performance liquid chromatography/mass spectrometry
MS or Mass Spec=mass spectrometry
mp=melting point

Process of Preparation

Inventive compounds that are inhibitors of mitochondrial $F_1F_0$ ATP hydrolase may be prepared by methods illustrated in the following Schemes I to IX. Starting materials are commercially available or can be readily prepared by one of ordinary skill in the art using known methods. For all of the schemes and compounds, the groups $R_1$–$R_4$ are as described above for a compound of Formula I and X is halogen, unless otherwise indicated. The group "Z" as used in these schemes corresponds to the group $NR_5R_6$, as described for a compound of Formula I, unless indicated otherwise. Groups designated generally as "R" are selected from substituents as set forth in the above definitions.

Solvents, temperatures, pressures, and other reaction conditions may readily be selected by one of ordinary skill in the art. High Speed Analoging (HSA) may be employed in the preparation of compounds, for example, where the intermediates possess a carboxylic acid or amino group. For ease of reference, abbreviations listed above are used in these schemes.

Scheme I

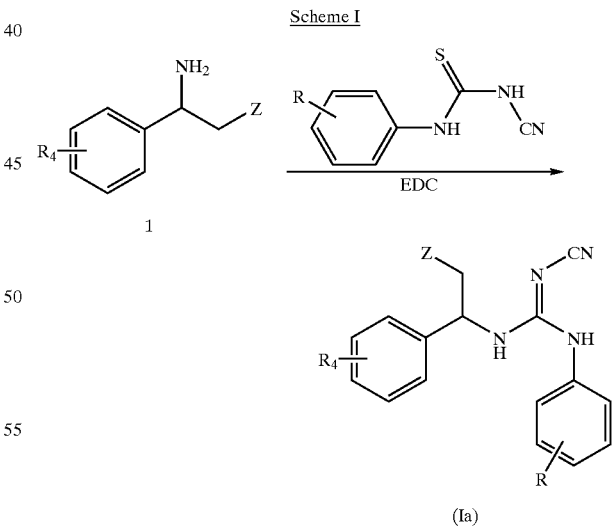

N-Arylcyanoguanidines of formula (Ia) were prepared by coupling 1-aryl-2-heteroaryl ethylamines 1 with N-aryl-N'-cyanothiourea in the presence of N-dimethylaminopropyl-N'-ethylcarbodiimide in solvent such as DMF. Ethylamines 1 may be prepared as described below in Schemes VI and VIII.

Scheme II

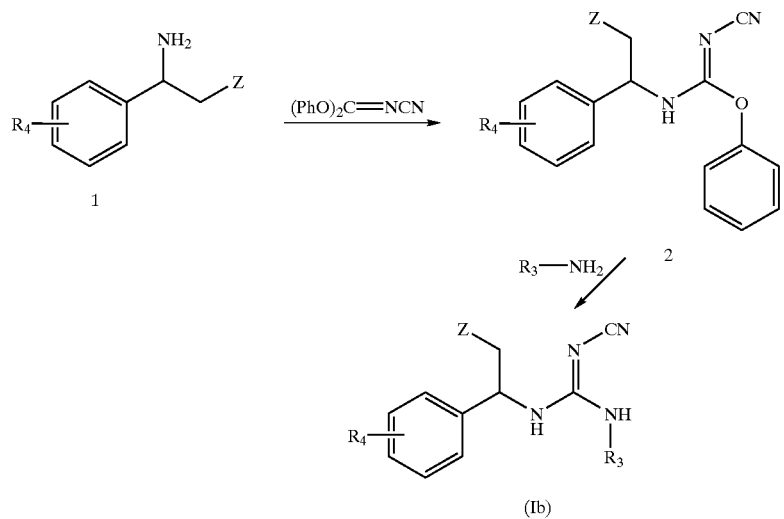

Cyanoguanidines of formula (Ib) were prepared by reacting 1-Aryl-2-heteroaryl ethylamines 1 (Schemes VI-VIII) with diphenylcyanoimidate to give compound 2. Subsequent reaction of 2 with amine $R_3$—$NH_2$ in a solvent such as acetonitrile at temperatures at around 80° C. gave cyanoguanidine (Ib). This synthetic scheme is advantageous for nucleophilic amines (R—$NH_2$), such as benzylamine.

Scheme III

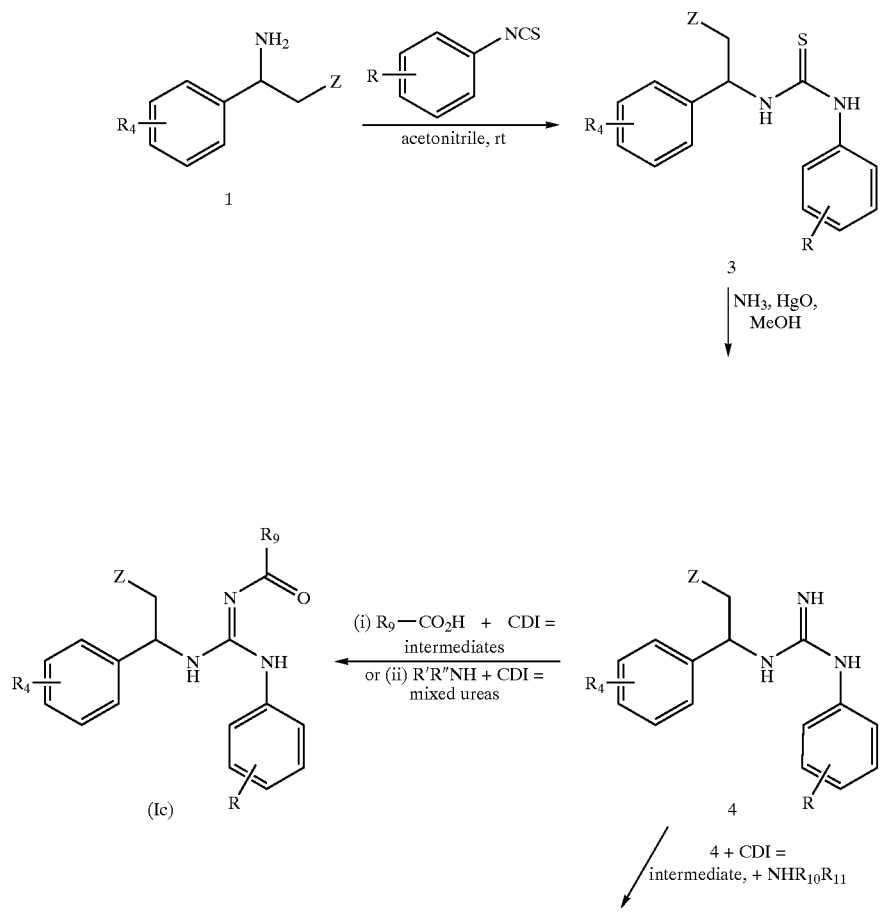

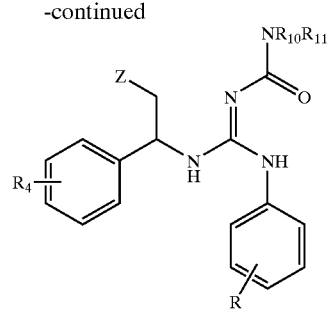

(Id)

1-Aryl-2-heteroaryl ethylamines 1 were used to prepare acylguanidines of formula (Ic) and ureidoguanidines of formula (Id). Reaction of ethylamines 1 with arylisothiocyanate in acetonitrile gave thiourea 3. Thiourea 3 was converted to guanidinie 4 by reaction with $NH_3$ in the presence of a metal reagent, such as HgO in solvent such as MeOH. Acyl guanidines (Ic) were prepared by two methods: (i) first reacting the corresponding acids ($R_9$—$CO_2H$) with CDI to produce intermediates, and then reacting the intermediates with guanidine 4, and (ii) reacting amines R'R"NH with CDI to produce mixed ureas, and then reacting the mixed ureas with guanidine 4. Ureidoguanidines of formula (Id) were prepared by first reacting guanidine 4 with CDI, and then reacting the intermediate with amine ($R_{10}R_{11}NH$).

Scheme IV

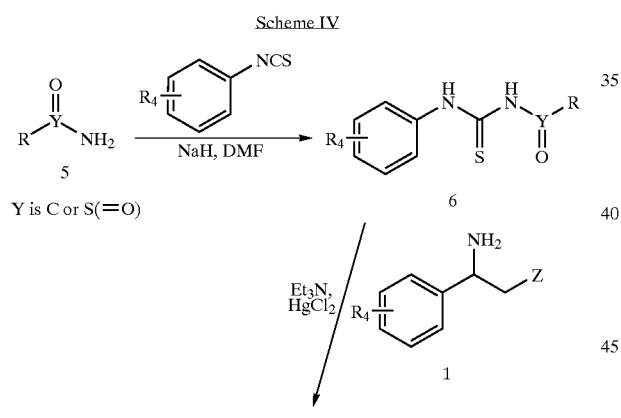

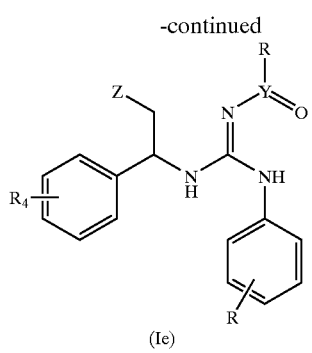

(Ie)

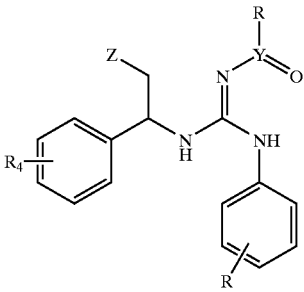

(Ie)

Treatment of urea 5 (Y═C) with a base such as sodium hydride in DMF, followed by addition of arylisothiocyanate gave thiourea 6. Treatment of 6 with 1-aryl-2-heteroaryl ethylamine 1 in the presence of a metal salt such as $HgCl_2$ gave acylguanidines of Formula (Ie). The same procedure may be followed to produce sulfonylguanidines of Formula (Ie) [Y═S(═O)] starting with sulfonamides 5 in step 1.

Scheme V

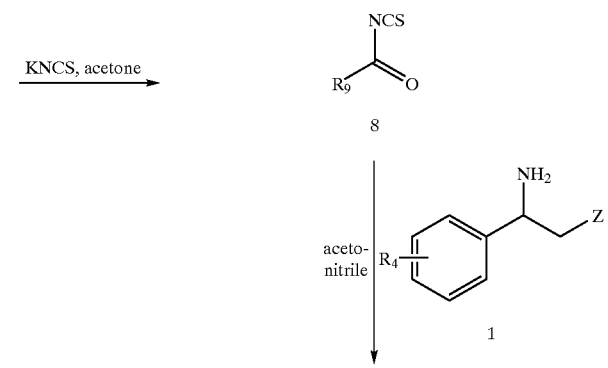

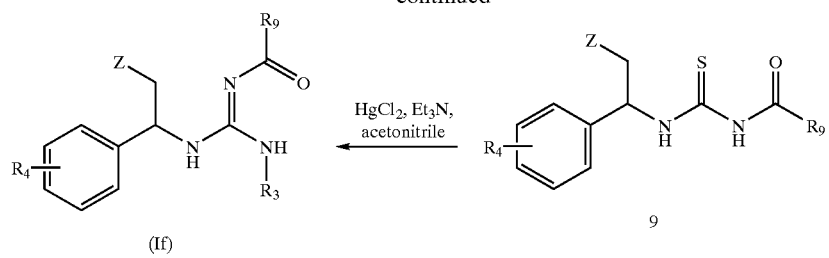

(If)

Acylguanidines of formula (If) were prepared by first converting acyl chloride 7 to acylisothiocyanate 8 by reaction with an isothiocyanate such as potassium isothiocyanate. Treatment of 8 with 1-aryl-2-heteroaryl ethylamine 1 gave acylthiourea 9. Treatment of 9 with TEA and a metal salt such as $HgCl_2$ in acetonitrile gave compounds (If).

Alcohol 12 was converted to amine 1 by reaction with an azide such as DPPA and DBU, followed by reduction with reducing agents such as $Ph_3P$ and water in a solvent such as THF.

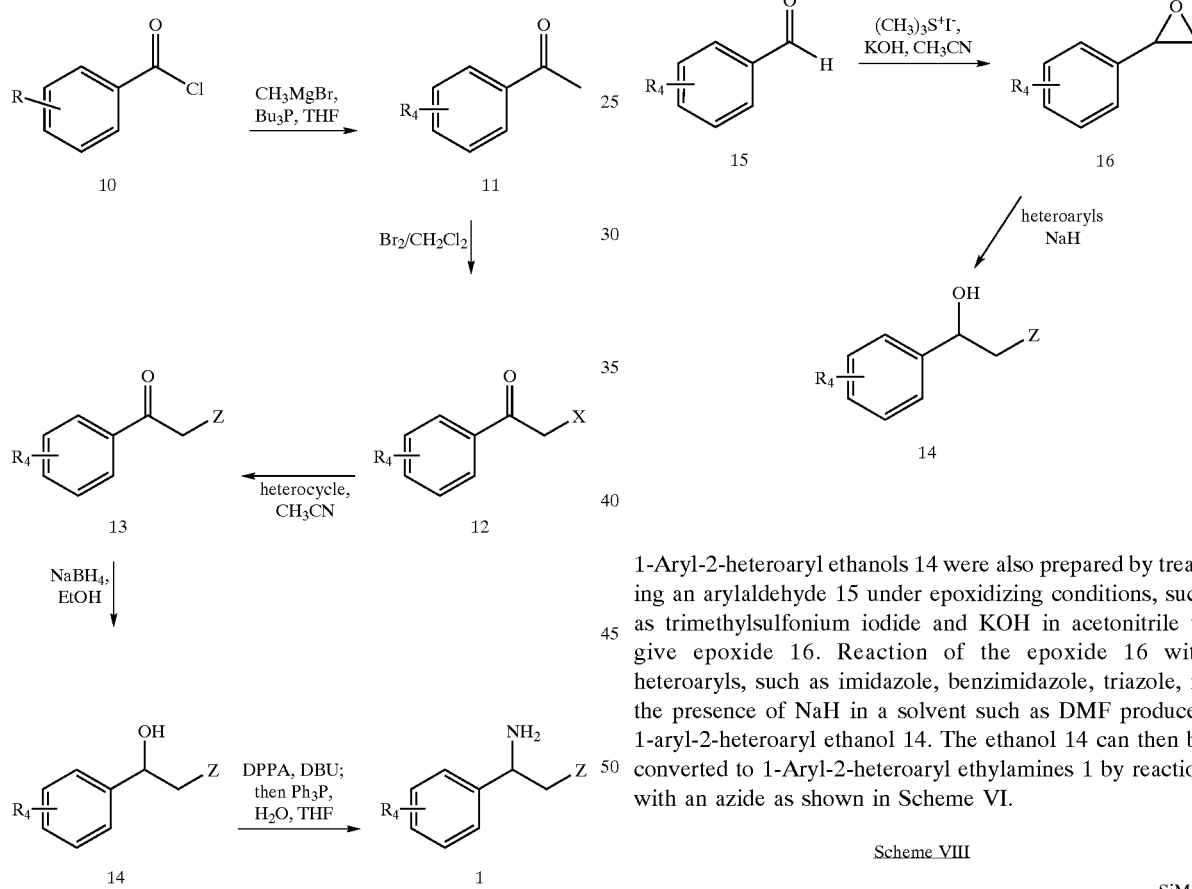

1-Aryl-2-heteroaryl ethylamines 1 (used in Schemes I–V) were prepared from aroylchlorides 10 and directly from acetophenones 11. Aroylchlorides 10 were reacted with methylmagnesium bromide in the presence of tributylphosphine in THF to give substituted acetophenone 11. Halogentation of acetophenones such as by bromination ($Br_2$/$CH_2Cl_2$), gave haloacetophenones 12. Displacement of the halogen in 12 with nucleophilic heteroaryls, such imidazole, benzimidazole, or triazole, in solvent, such as acetonitrile, gave compound 13. Reduction of ketone 13 with a reducing agent, such as sodium borohydride, in a solvent such as EtOH, gave substituted 1-aryl-2-heteroaryl ethanol 12.

1-Aryl-2-heteroaryl ethanols 14 were also prepared by treating an arylaldehyde 15 under epoxidizing conditions, such as trimethylsulfonium iodide and KOH in acetonitrile to give epoxide 16. Reaction of the epoxide 16 with heteroaryls, such as imidazole, benzimidazole, triazole, in the presence of NaH in a solvent such as DMF produced 1-aryl-2-heteroaryl ethanol 14. The ethanol 14 can then be converted to 1-Aryl-2-heteroaryl ethylamines 1 by reaction with an azide as shown in Scheme VI.

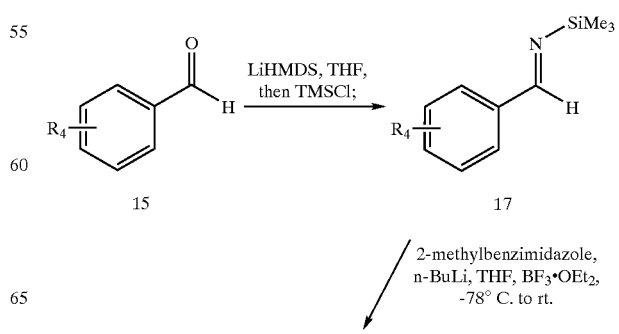

1-Aryl-2-heteroaryl ethylamines 1

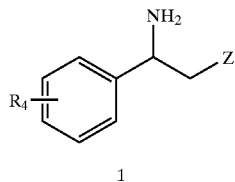

(where Z = 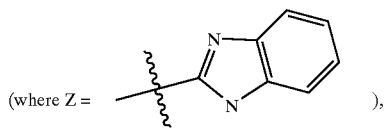 ), can also be prepared by reacting arylaldehydes 15 with LiHMDS in THF and then with TMSCl to produce compounds 17. Compounds 17 when reacted with 2-methylbenzimidazole, N-BuLi, and $BF_3OEt_2$ gave ethylamines 1.

Scheme IX

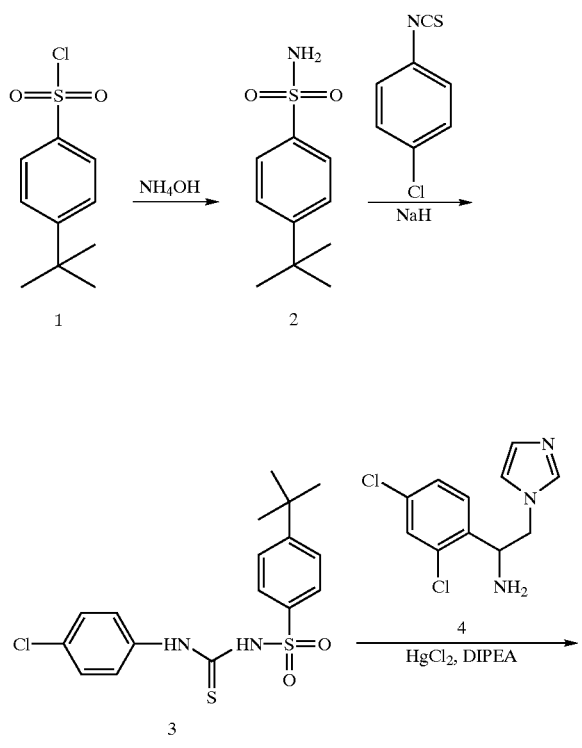

N-(Aryl)sulphonylguanidines can be prepared by treatment of arylsulphonyl chlorides 1 with ammonium hydroxide to produce arylsulphonamines 2, which yield thioureas 3 upon treatment with isothiocyanates and a base, such as sodium hydride. Reaction of these N-aryl-N'-arylsulphonylthioureas with a benzylic amine such as 4, in the presence of $HgCl_2$ and a base, such as DIPEA, yields N-(aryl) sulphonylguanidines 5.

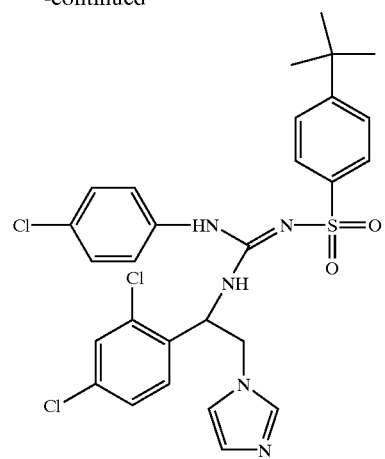

The invention will now be further described by the following working examples, which are illustrative rather than limiting. All temperatures are in degrees Celsius (° C.) unless otherwise indicated.

EXAMPLE 1
N-(2,4-Dichlorophenyl)-N'-[1-(2,5-bistrifluoromethylphenyl)-2-(imidazol-1-yl)-ethyl]-N''-cyanoguanidine

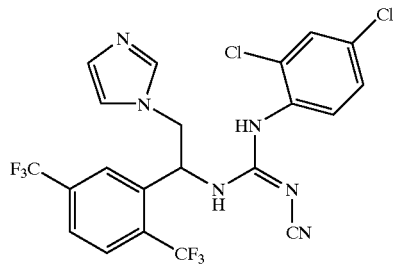

A. 2,5-Bistrifluoromethyl-1-methylcarbonylbenzene.

To a stirred solution of 2,5-trifluoromethylbenzoyl chloride (10 g, 36 mmol) in THF (150 mL) at –20° C., was added tributylphosphine (10 mL, 40 mmol) over 5 min. After stirring for 20 min, a solution of methylmagnesium bromide (3M, 12 mL) in THF was added rapidly (1 min). After addition, the reaction mixture was allowed to stir for 30 min, 1N HCl solution (20 mL) was added, and the mixture was concentrated in vacuo. The residue was partitioned between ether and 1N HCl solution. The aqueous solution was extracted with ether, the combined organic layers were dried and concentrated, and the residue was purified by silica gel column chromatography (5% EtOAc in hexanes) to give 5.1 g (56%) of Compound A as an oil.

B. T-Bromomethylcarbonyl-2,5-bistrifluoromethylbenzene.

To a stirred solution of Compound A (5.1 g, 20 mmol) in $CH_2Cl_2$ at rt was added a solution of Br (1.03 g) in $CH_2Cl_2$. The mixture was allowed to stir for 6 h and then washed with saturated $NaHCO_3$. The organic layer was dried and concentrated to give Compound B as a yellow oil (6.5 g, 97%).

C. 2,5-Bistrifluoromethyl-1-(imidazol-1-yl)methylcarbonyl)benzene.

To a stirred solution of Compound B (6.5 g, 19.5 mmol) in CH₂Cl₂ (100 mL) was added imidazole (3.32 g, 48.7 mmol), and the mixture was allowed to stir at rt for 18 h. The solvent was removed, and the residue was partitioned between EtOAc (200 mL) and water. The organic layer was washed with ammonium chloride solution, dried, and concentrated to give Compound C as a solid, which was directly used in next step without further purification.

D. 1-(2,5-Bistrifluoromethylphenyl)-2-(imidazol-1-yl)ethanol.

To a stirred solution of Compound C (4.2 g, 13.5 mmol) in EtOH at 0° C. was added NaBH₄ (260 mg, 6.8 mmol) in one portion. This was allowed to stir at 0° C. for 2 h. The solvent was removed, and the residue was partitioned between EtOAc and NaHCO₃ solution. The organic layer was separated, dried, and concentrated to give Compound D as a solid (4.1 g, 94%).

E. 1-(2,5-Bistrifluoromethylphenyl)-2-(imidazol-1-yl)ethylamine.

To a stirred suspension of Compound D (4.0 g, 12.3 mmol) in toluene (40 mL) at 0° C., was added DPPA (2.9 mL, 13.6 mmol), followed by addition of DBU (2.2 mL, 14.8 mmol). The stirred reaction mixture was allowed to heat at 60° C. for 18 h. The mixture was allowed to cool and was then partitioned between EtOAc and water. The organic layer was washed with brine (3×50 mL), dried, concentrated, and re-dissolved in acetonitrile. Water (1.0 mL) was added to the solution, followed by Ph₃P (4 g, 15.1 mmol), and the mixture was allowed to heat at reflux for 18 h. The solution was cooled and concentrated. The residue was partitioned between EtOAc and 10% HCl solution. The aqueous solution was extracted with EtOAc and basified (pH 12) with ION NaOH solution at 0° C. The aqueous solution was extracted with EtOAc, and combined extracts were dried (Na₂SO₄) and concentrated to give Compound E as a solid.

F. N-(2,4-Dichlorophenyl)-N'-[1-(2,5-bistrifluoromethylphenyl)-2-(imidazol-1-yl)-ethyl]-N''-cyanoguanidine. To a stirred solution of Compound E (1.1 g, 3.4 mmol) in DMF at rt was added N-cyano-N'-(2,4-dichlorophenyl)thiourea (1.1 g, 4.1 mmol), followed by EDC (800 mg, 4.1 mmol). The mixture was allowed to stir at rt for 18 h and then partitioned between EtOAc and saturated ammonium chloride solution. The organic layer was separated and washed with saturated ammonium chloride solution (3×50 mL). The organic layer was dried, concentrated, and the residue was purified by silica gel column chromatography (EtOAc, MeOH, NR4OH; 95:5:0.1) to give Example 1 as a solid (350 mg). MS (ES): m/z 535 [M+H]⁺.

EXAMPLES 2–11
N-(aryl)-N'-[1-(2,5-bistrifluoromethylphenyl)-2-(imidazol-1-yl)-ethyl]-N''-cyanoguanidines

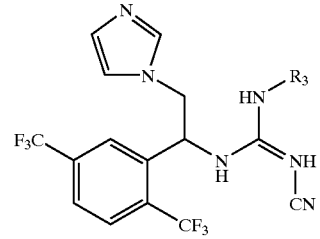

(Ig)

Compounds having the formula (Ig), wherein R₃ has the values listed in Table 1 were prepared by following the procedure described for Example 1, except in Step F, different ureas were used.

TABLE 1

| Example # | R₃ | Data |
|---|---|---|
| 2 | 3,4-dichlorophenyl | MS 535 [M + H]⁺ |
| 3 | 2,5-dichlorophenyl | MS 535 [M + H]⁺ |
| 4 | 4-bromo-2-methylphenyl | MS 559 [M + H]⁺ |
| 5 | 4-fluoro-2-methylphenyl | MS 498 [M + H]⁺ |
| 6 | 4-chloro-2-methylphenyl | MS 514 [M + H]⁺ |

TABLE 1-continued

| Example # | R3 | Data |
|---|---|---|
| 7 | 4-chlorophenyl | MS 500 [M + H]+ |
| 8 | 2-chloro-4-methylphenyl | MS 514 [M + H]+ |
| 9 | 2-chlorophenyl | MS 500 [M + H]+ |
| 10 | 3-chlorophenyl | MS 500 [M + H]+ |
| 11 | phenyl | MS 466 [M + H]+ |

EXAMPLE 12

N-(Diphenylmethyl)-N'-[1-(2,5-bistrifluoromethylphenyl)-2-(imidazol-1-yl)-ethyl]-N"-cyanoguanidine

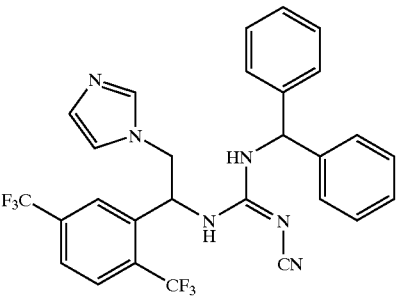

A. N-[1-(2,5-Bistrifluoromethylphenyl)-2-(imidazol-1-yl)-ethyl]-N'-cyano-phenylureanate. To a stirred solution of 1-(2,5-bistrifluoromethylphenyl)-2-(imidazol-1-yl) ethylamine (220 mg, 0.68 mmol) in acetonitrile (5 mL) at rt was added diphenyl cyanocarbonimidate (178 mg, 71 mmol). The reaction mixture was allowed to stir at rt for 18 h. The solvent was removed, and the residue was purified by silica gel column chromatography (EtOAc, MeOH; 9:1) to give 160 mg (55%) of Compound A.

B. N-(Diphenylmethyl)-N'-[1-(2,5-bistrifluoromethylphenyl)-2-(imidazol-1-yl)-ethyl]-N"-cyanoguanidine. To a stirred solution of Compound A (10 mg) in acetonitrile (2 mL) at rt was added diphenylmethylamine (20 mg). The reaction mixture was heated at reflux for 18 h. The mixture was then concentrated and the residue purified by silica gel column chromatography (EtOAc, MeOH, NH4OH; 90:10:0.1) to give Example 12 (5 mg). MS (ES): m/z 556 [M+H]+.

EXAMPLES 13–76

N-Substituted-N'-[1-(2,5-bistrifluoromethylphenyl)-2-(imidazol-1-yl)-ethyl]-N"-cyanoguanidines

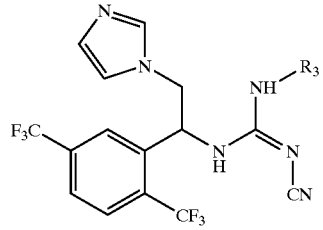

(Ih)

Compounds having the formula (Ih), wherein $R_3$ has the values listed in Table 2 were prepared by following the same or similar procedure described for Example 12, except in Step B, different amines were used.

TABLE 2

| Example # | R3 | Data |
|---|---|---|
| 13 | benzyl | MS 480 [M + H]+ |
| 14 | 3-(trifluoromethyl)benzyl | MS 548 [M + H]+ |
| 14 | 4-bromobenzyl | MS 559 [M + H]+ |
| 15 | 4-(aminosulfonyl)phenethyl | MS 559 [M + H]+ |
| 16 | 3,5-dichlorobenzyl | MS 549 [M + H]+ |

TABLE 2-continued

| Example # | R₃ | Data |
|---|---|---|
| 17 | 4-bromophenethyl | MS 559 [M + H]⁺ |
| 18 | 3,4-dichlorobenzyl | MS 549 [M + H]⁺ |
| 19 | naphthalen-2-ylmethyl | MS 530 [M + H]⁺ |
| 20 | 2,4-dichlorobenzyl | MS 549 [M + H]⁺ |
| 21 | 4-chlorophenethyl | MS 514 [M + H]⁺ |
| 22 | 3,4,5-trimethoxybenzyl | MS 570 [M + H]⁺ |
| 23 | 4-phenoxyphenethyl | MS 572 [M + H]⁺ |
| 24 | 3,5-dimethoxybenzyl | MS 540 [M + H]⁺ |
| 25 | 4-methoxyphenethyl | MS 524 [M + H]⁺ |
| 26 | benzothiophen-3-ylmethyl | MS 536 [M + H]⁺ |
| 27 | 3,5-difluorobenzyl | MS 516 [M + H]⁺ |
| 28 | 3-iodobenzyl | MS 606 [M + H]⁺ |
| 29 | benzo[1,3]dioxol-5-ylmethyl | MS 524 [M + H]⁺ |
| 30 | benzylthioethyl | MS 540 [M + H]⁺ |
| 31 | N-methyl-N-phenylaminopropyl | MS 537 [M + H]⁺ |
| 32 | N-ethyl-N-(3-methylphenyl)aminoethyl | MS 551 [M + H]⁺ |
| 33 | 2-oxopyrrolidin-1-ylpropyl | MS 515 [M + H]⁺ |
| 34 | (4-methoxynaphthalen-2-yl)aminocarbonylpropyl | MS 617 [M + H]⁺ |
| 35 | 2-chloro-6-phenoxybenzyl | MS 606 [M + H]⁺ |
| 36 | 4-(4,5-dihydro-1,2,3-thiadiazol-4-yl)phenethyl | MS 564 [M + H]⁺ |

TABLE 2-continued

| Example # | R₃ | Data |
|---|---|---|
| 37 | 1-(naphthalen-1-yl)ethyl | MS 544 [M + H]⁺ |
| 38 | 3-(5-benzyloxy-1H-indol-3-yl)propyl | MS 639 [M + H]⁺ |
| 39 | 2-(2,4-dichlorophenyl)ethyl | MS 563 [M + H]⁺ |
| 40 | 3,3-diphenylpropyl | MS 570 [M + H]⁺ |
| 41 | 1-(ethoxycarbonyl)piperidin-4-yl | MS 545 [M + H]⁺ |
| 42 | trans-2-phenylcyclopropyl | MS 506 [M + H]⁺ |
| 43 | 2-(2-methoxyphenyl)ethyl | MS 524 [M + H]⁺ |
| 44 | 2-(naphthalen-1-ylamino)ethyl | MS 559 [M + H]⁺ |
| 45 | 2-phenylpropyl | MS 508 [M + H]⁺ |
| 46 | 4-methylcyclohexyl | MS 486 [M + H]⁺ |
| 47 | 2,3-dimethylcyclohexyl | MS 500 [M + H]⁺ |
| 48 | 1-(2,5-dichlorophenyl)ethyl | MS 549 [M + H]⁺ |
| 49 | 4-tert-butylcyclohexyl | MS 528 [M + H]⁺ |
| 50 | 3-(1H-indol-3-yl)propyl | MS 533 [M + H]⁺ |
| 51 | 2-(piperidin-1-yl)ethyl | MS 501 [M + H]⁺ |
| 52 | 3-(morpholin-4-yl)propyl | MS 517 [M + H]⁺ |
| 53 | 2-(3,4-dimethoxyphenyl)ethyl | MS 554 [M + H]⁺ |

TABLE 2-continued

| Example # | R₃ | Data |
|---|---|---|
| 54 | 3,4-bis(benzyloxy)phenethyl | MS 706 [M + H]⁺ |
| 55 | indan-1-yl | MS 506 [M + H]⁺ |
| 56 | 2-[1-(4-chlorophenyl)cyclopropyl]ethyl | MS 554 [M + H]⁺ |
| 57 | 1,2,3,4-tetrahydronaphthalen-1-yl | MS 520 [M + H]⁺ |
| 58 | (2-benzyl-3-hydroxypropyl) | MS 524 [M + H]⁺ |
| 59 | 1-phenylethyl | MS 494 [M + H]⁺ |
| 60 | (1-hydroxy-3-methoxy-1-phenylpropan-2-yl) | MS 554 [M + H]⁺ |
| 61 | 2-methyl-N-(naphthalen-2-yl)propanamido | MS 587 [M + H]⁺ |
| 62 | 3-(3-hydroxy-4-methylphenyl)-1-ethylpropyl | MS 582 [M + H]⁺ |
| 63 | 1-(4-chlorophenyl)ethyl | MS 542 [M + H]⁺ |
| 64 | (1-benzylpyrrolidin-3-yl) | MS 549 [M + H]⁺ |
| 65 | norbornan-2-yl | MS 484 [M + H]⁺ |
| 66 | bis(4-methoxyphenyl)methyl | MS 616 [M + H]⁺ |
| 67 | 2-(4-ethylphenyl)ethyl | MS 522 [M + H]⁺ |
| 68 | 1-(4-methylphenyl)-2-phenyl-2-yl | MS 584 [M + H]⁺ |
| 69 | (2-((benzylthio)methyl)-3-hydroxypropyl) | MS 570 [M + H]⁺ |
| 70 | (1-benzyl-2-methoxyethyl) | MS 538 [M + H]⁺ |
| 71 | (1,2-diphenylethyl) | MS 570 [M + H]⁺ |
| 72 | (2-benzyl-3-hydroxypropyl) (S) | MS 524 [M + H]⁺ |

TABLE 2-continued

| Example # | R₃ | Data |
|---|---|---|
| 73 | (S)-2-phenyl-2-hydroxyethyl stereochem | MS 510 [M + H]⁺ |
| 74 | (R)-2-phenyl-2-hydroxyethyl stereochem | MS 510 [M + H]⁺ |
| 75 | chroman-3,4-diol with t-butyl hydroxymethyl substituent | MS 652 [M + H]⁺ |
| 76 | 2-hydroxy-2-phenylethyl | MS 510 [M + H]⁺ |

EXAMPLES 77–81

N'-[1-(2,5-bistrifluoromethylphenyl)-2-(imidazol-1-yl)-ethyl]-N''-cyanoguanidines

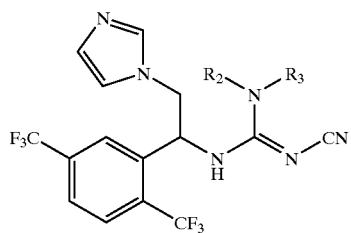

(Ii)

The compounds having the formula (Ii), wherein —NR₂R₃ taken together have the values listed in Table 3, were prepared by following the procedure described above for Example 12, except different amines were used in Step B.

TABLE 3

| Example # | —NR₂R₃ | Data |
|---|---|---|
| 77 | N-methyl-N-benzyl | MS 494 [M + H]⁺ |
| 78 | N,N-dibenzyl | MS 570 [M + H]⁺ |

TABLE 3-continued

| Example # | —NR₂R₃ | Data |
|---|---|---|
| 79 | N-methyl-N-(3,4-dichlorobenzyl) | MS 563 [M + H]⁺ |
| 80 | 4-benzylpiperazin-1-yl | MS 549 [M + H]⁺ |
| 81 | 2,6-dimethylmorpholin-4-yl | MS 488 [M + H]⁺ |

EXAMPLE 82

N-(2,4-Dichlorophenyl)-N'-[1-(2,4-dichlorophenyl)-2-(imidazol-1-yl)-ethyl]-N''-cyanoguanidine

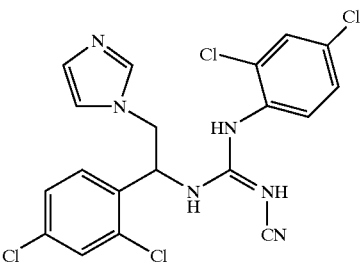

The general procedure described in Example 1 (Steps C–F) was followed to synthesize Example 82; however, in Step C, trichloroacetophenone was used instead of 1-bromomethylcarbonyl-2,5-bistrifluoromethylbenzene to produce the intermediate 1-(2,4-dichlorophenyl)-2-(imidazol-1-yl)ethylamine as a white solid, and then this intermediate was used in step F instead of 1-(2,5-bistrifluoromethylphenyl)-2-(imidazol-1-yl)ethylamine, to provide Example 82 as a solid. MS (ES): m/z 468 [M+H]⁺.

EXAMPLES 83–104

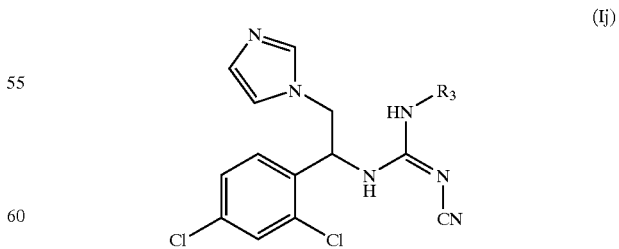

(Ij)

Compounds having the formula (Ij), wherein R₃ has the values listed in Table 4, were prepared by following the procedure described above in Example 82, except different cyanothioureas were used in Step F.

TABLE 4

| Example # | R₃ | Data |
|---|---|---|
| 83 | 2,3-dichlorophenyl | MS 468 [M + H]⁺ |
| 84 | 3,5-dichlorophenyl | MS 468 [M + H]⁺ |
| 85 | 3,4-dichlorophenyl | MS 468 [M + H]⁺ |
| 86 | 4-chlorophenyl | MS 433 [M + H]⁺ |
| 87 | 2-chlorophenyl | MS 433 [M + H]⁺ |
| 88 | 3-chlorophenyl | MS 433 [M + H]⁺ |
| 89 | 2,5-dichlorophenyl | MS 468 [M + H]⁺ |
| 90 | 2,6-dichlorophenyl | MS 468 [M + H]⁺ |
| 91 | 3-(benzyloxy)phenyl | MS 505 [M + H]⁺ |
| 92 | 2,4-dimethylphenyl | MS 427 [M + H]⁺ |
| 93 | 3-chloro-2-methylphenyl | MS 447 [M + H]⁺ |
| 94 | 3,4-dimethoxyphenyl | MS 459 [M + H]⁺ |
| 95 | 4-methylphenyl | MS 413 [M + H]⁺ |
| 96 | 4-fluorophenyl | MS 417 [M + H]⁺ |
| 97 | 2,4,6-trimethylphenyl | MS 441 [M + H]⁺ |
| 98 | 3-(trifluoromethyl)phenyl | MS 467 [M + H]⁺ |
| 99 | 4-chloro-2-methylphenyl | MS 447 [M + H]⁺ |
| 100 | 2-naphthyl | MS 449 [M + H]⁺ |

TABLE 4-continued

| Example # | R3 | Data |
|---|---|---|
| 101 | 4-(F3C)-C6H4- | MS 467 [M + H]+ |
| 102 | 2-(CF3)-C6H4- | MS 467 [M + H]+ |
| 103 | 4-(F3C-O)-C6H4- | MS 483 [M + H]+ |
| 104 | 4-Br-2-CH3-C6H3- | MS 492 [M + H]+ |

EXAMPLE 105

N-[1-(2,4-Dichlorophenyl)-2-(imidazol-1-yl)-ethyl]-N'-[(3-phenyl)propyl]-N"-cyanoguanidine

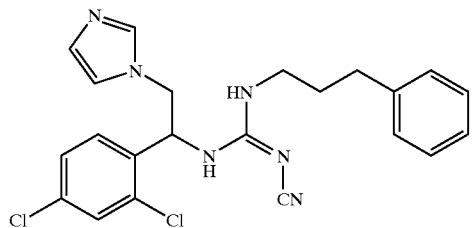

The procedure described for Example 12 was followed, except 1-(2,4-dichlorophenyl)-2-(imidazol-1-yl)-ethylamine was used in Step A to produce the intermediate N-[1-(2,4-Dichlorophenyl)-2-(imidazol-1-yl)-ethyl]-N'-(3-phenylpropyl)-N"-cyanoguanidine, and then that intermediate was used in Step B with 3-phenylpropylamine (instead of diphenylmethylamine) to produce Example 105.

EXAMPLES 106–128

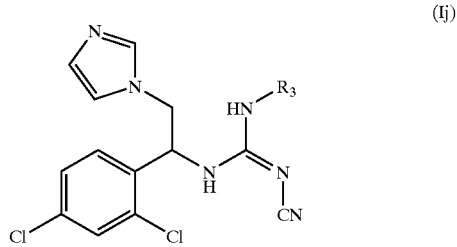

(Ij)

Compounds having formula (Ij), wherein $R_3$ has the values listed in Table 5, were prepared by following the procedure described above for Example 105, except using different amines in Step B.

TABLE 5

| Example # | R3 | Data |
|---|---|---|
| 105 | Ph-(CH2)3- | MS 441 [M + H]+ |
| 106 | n-Bu— | MS 379 [M + H]+ |
| 107 | HO(CH2)3— | MS 381 [M + H]+ |
| 108 | EtOEt— | MS 395 [M + H]+ |
| 109 | HO(CH2)4— | MS 395 [M + H]+ |
| 110 | CH3-CH(OH)-CH2- | MS 381 [M + H]+ |
| 111 | 1-benzylpiperidin-4-yl | MS 496 [M + H]+ |
| 112 | 3-Cl-C6H4-(CH2)2- | MS 461 [M + H]+ |
| 113 | PhCH2-S-CH2CH2- | MS 473 [M + H]+ |
| 114 | 2-(2-(HOCH2)-C6H4-S)-C6H4-CH2CH2- | MS 551 [M + H]+ |

TABLE 5-continued

| Example # | R₃ | Data |
|---|---|---|
| 115 | 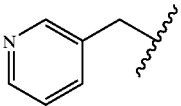 | MS 414 [M + H]⁺ |
| 116 | 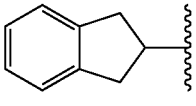 | MS 439 [M + H]⁺ |
| 117 | 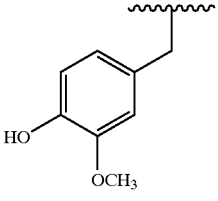 | MS 459 [M + H]⁺ |
| 118 | 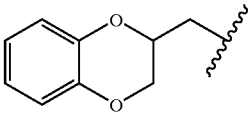 | MS 471 [M + H]⁺ |
| 119 | 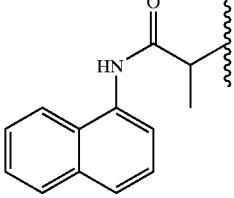 | MS 520 [M + H]⁺ |
| 120 | 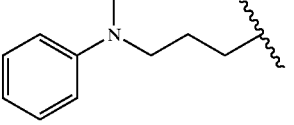 | MS 470 [M + H]⁺ |
| 121 | 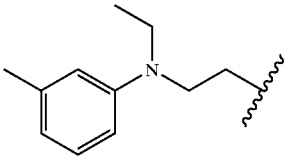 | MS 484 [M + H]⁺ |
| 122 | 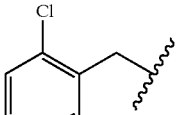 | MS 447 [M + H]⁺ |
| 123 | 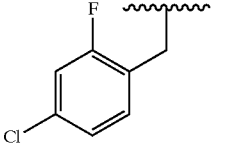 | MS 465 [M + H]⁺ |
| 124 | 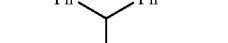 | MS 489 [M + H]⁺ |
| 125 |  | MS 427 [M + H]⁺ |
| 126 | 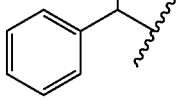 | MS 487 [M + H]⁺ |
| 127 | 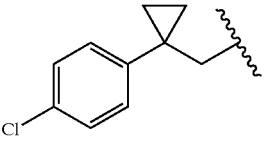 | MS 517 [M + H]⁺ |
| 128 | 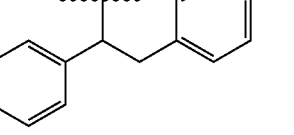 | MS 485 [M + H]⁺ |

EXAMPLE 129

(2,5-Dichlorophenyl)-N'-[1-(2,4-dichlorophenyl)-2-(imidazol-1-yl)-ethyl]-N''-cyanoguanidine

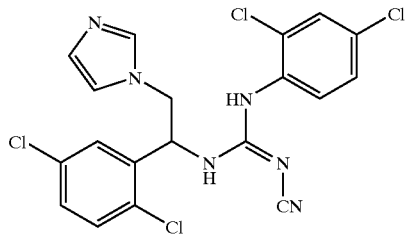

Steps B to E of Example 1 were followed, starting with 2,5-dichlorophenylmethyl-carbonylbenzene in Step B, to produce after Step E the intermediate 1-(2,5-Dichlorophenyl)-2-(imidazol-1-yl)ethylamine; and then this amine was used as Compound E in Step F of Example 1 to obtain the titled compound as a solid. MS (ES): m/z 467 [M+H]⁺.

EXAMPLES 130–135

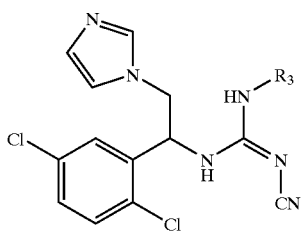

(Ik)

Compounds having formula (Ik), wherein R₃ has the values listed in Table 6, were prepared by following the procedure as described above for Example 129, except in Step F, different N-aryl-N'-cyanothioureas were used instead of N-cyano-N'-(2,4-dichlorophenyl)thiourea.

TABLE 6

| Example # | R₃ | Data |
|---|---|---|
| 130 | 2-methyl-4-bromophenyl | MS 492 [M + H]⁺ |
| 131 | 2-chloro-4-methylphenyl | MS 447 [M + H]⁺ |
| 132 | 3,4-dichlorophenyl | MS 468 [M + H]⁺ |
| 133 | 3,5-dichlorophenyl | MS 468 [M + H]⁺ |
| 134 | 2,4-dimethylphenyl | MS 427 [M + H]⁺ |
| 135 | 2-methyl-4-chlorophenyl | MS 447 [M + H]⁺ |

EXAMPLE 136

N-(2,5-Dichlorophenyl)-N'-[1-(2,4-dichlorophenyl)-2-(imidazol-1-yl)-ethyl]-N''-cyanoguanidine

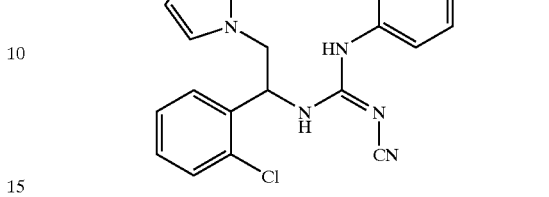

The procedure of Example 1 was followed, except in Step B, 2-chlorophenylmethylketone was used as Compound A (instead of 2,5-bistrifluoromethyl-1-methylcarbonylbenzene), to produce after Step E 1-(2-Chlorophenyl)-2-(imidazol-1Interleukin-1 receptor antagonists); solid. MS (ES): m/z 433 [M+H]⁺.

EXAMPLE 137–147

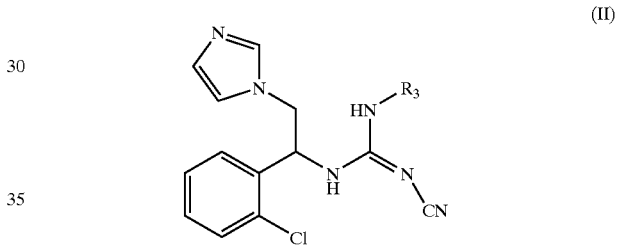

(II)

Compounds having the formula (II), wherein R₃ has the values listed in Table 7 were prepared by following the procedure as described for Example 136, except different N-aryl-N'-cyanothioureas were used in Step F.

TABLE 7

| Example # | R₃ | Data |
|---|---|---|
| 137 | 4-phenoxyphenyl | MS 456 [M + H]⁺ |
| 138 | 2-methyl-4-chlorophenyl | MS 413 [M + H]⁺ |
| 139 | indanyl | MS 404 [M + H]⁺ |

TABLE 7-continued

| Example # | R₃ | Data |
|---|---|---|
| 140 | 3-BnO-phenyl | MS 470 [M + H]⁺ |
| 141 | 4-F-2-CH₃-phenyl | MS 396 [M + H]⁺ |
| 142 | 2-Cl-4-CH₃-phenyl | MS 413 [M + H]⁺ |
| 143 | 4-Br-2-CH₃-phenyl | MS 457 [M + H]⁺ |
| 144 | 3,5-diCl-phenyl | MS 433 [M + H]⁺ |
| 145 | 3,4-diCl-phenyl | MS 433 [M + H]⁺ |
| 146 | 4-Cl-phenoxy | MS 399 [M + H]⁺ |
| 147 | 4-Cl-phenethyl | MS 392 [M + H]⁺ |

EXAMPLE 148

N-(4-Chlorophenyl)-N'-[1-(2,3-dichlorophenyl)-2-(imidazol-1-yl)-ethyl]-N''-cyanoguanidine

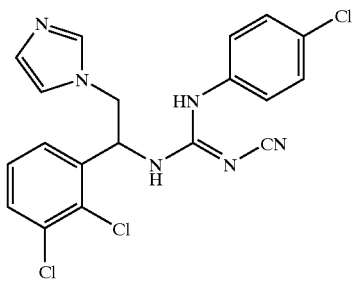

The procedure of Example 1 was followed, except 2,3-Dichlorophenylmethylketone was used in Step B instead of 2,5-bistrifluoromethyl-1-methylcarbonylbenzene, to produce after Step E 1-(2,3-Dichlorophenyl)-2-(imidazol-1-yl) ethylamine, and then step F was followed with this ethylamine to obtain Example 148 as a solid. MS (ES): m/z 433 [M+H]⁺.

EXAMPLES 149–154

(Im)

Compounds having formula (Im), wherein R₃ has the values listed in Table 8, were prepared by following the procedure described for Example 148, except different N-aryl-N'-cyanothioureas were used in Step F.

TABLE 8

| Example # | R₃ | Data |
|---|---|---|
| 149 | 2,4-diCH₃-phenyl | MS 427 [M + H]⁺ |
| 150 | 4-F-2-CH₃-phenyl | MS 431 [M + H]⁺ |

TABLE 8-continued

| Example # | R₃ | Data |
|---|---|---|
| 151 | 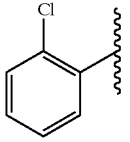 2-Cl-phenyl | MS 433 [M + H]⁺ |
| 152 | 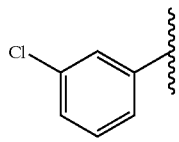 3-Cl-phenyl | MS 433 [M + H]⁺ |
| 153 | 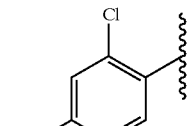 2-Cl-4-Me-phenyl | MS 447 [M + H]⁺ |
| 154 | 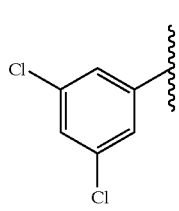 3,5-diCl-phenyl | MS 468 [M + H]⁺ |

EXAMPLE 155

N-(2,4-Dichlorophenyl)-N'-[1-(2,4-bistrifluoromethylphenyl)-2-(imidazol-1-yl)-ethyl]-N"-cyanoguanidine

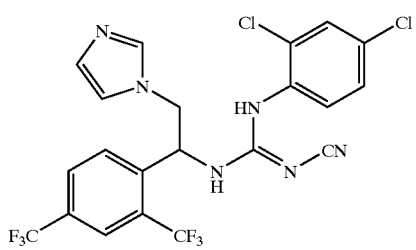

The procedure of Example 1 was followed, except 2,4-bistrifluoromethyl-phenylmethylketone was used as Compound A in Step B to produce 1-(2,4-Bistrifluoromethylphenyl)-2-(imidazol-1-yl)ethylamine (after Step E), and then Step F was followed with this ethylamine to obtain Example 155 as a solid. MS (ES): m/z 535 [M+H]⁺.

EXAMPLES 156–171

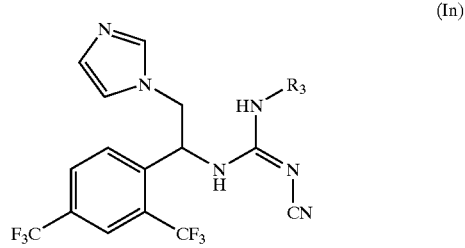

(In)

Compounds having the formula (In) were prepared wherein R₃ has the values listed in Table 9, following the procedure as described for Example 155, except different N-aryl-N'-cyanothioureas were used in Step F.

TABLE 9

| Example # | R₃ | Data |
|---|---|---|
| 156 | 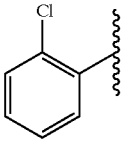 2-Cl-phenyl | MS 500 [M + H]⁺ |
| 157 | 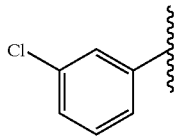 3-Cl-phenyl | MS 500 [M + H]⁺ |
| 158 | 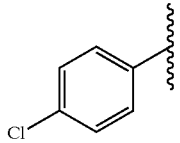 4-Cl-phenyl | MS 500 [M + H]⁺ |
| 159 | 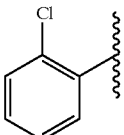 2,4-diCl-phenyl | MS 535 [M + H]⁺ |
| 160 | 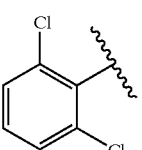 2,6-diCl-phenyl | MS 535 [M + H]⁺ |
| 161 | 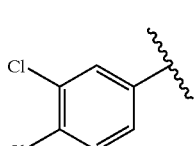 3,4-diCl-phenyl | MS 535 [M + H]⁺ |

TABLE 9-continued

| Example # | R₃ | Data |
|---|---|---|
| 162 | 3,5-dichlorophenyl | MS 535 [M + H]⁺ |
| 163 | 4-phenoxyphenyl | MS 558 [M + H]⁺ |
| 164 | 4-chloro-2-methylphenyl | MS 514 [M + H]⁺ |
| 165 | indanyl | MS 506 [M + H]⁺ |
| 166 | 4-fluoro-2-methylphenyl | MS 498 [M + H]⁺ |
| 167 | 2,4-dimethylphenyl | MS 494 [M + H]⁺ |
| 168 | 2-chloro-4-methylphenyl | MS 514 [M + H]⁺ |
| 169 | 4-bromo-2-methylphenyl | MS 559 [M + H]⁺ |
| 170 | cyclohexyl | MS 472 [M + H]⁺ |
| 171 | 4-chlorophenylpropyl | MS 528 [M + H]⁺ |

EXAMPLE 172

N-(2,4-Dichlorophenyl)-N'-[1-(2,4-bistrifluoromethylphenyl)-2-[1-(1,2,4-triazolyl)]-ethyl]-N''-cyanoguanidine

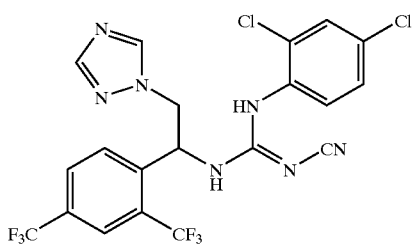

Example 172 was synthesized following the procedure described for Example 155, except triazole was used instead of imidazole (i.e., as per Example 1, Step C), to produce 1-(2,4-Bistrifluoromethylphenyt)-2-[1-(1,2,4-triazolyl)]ethylamine, and this ethylamine was used in the last step to make the titled compound as a solid. MS (ES): m/z 536 [M+H]⁺.

EXAMPLES 173–175

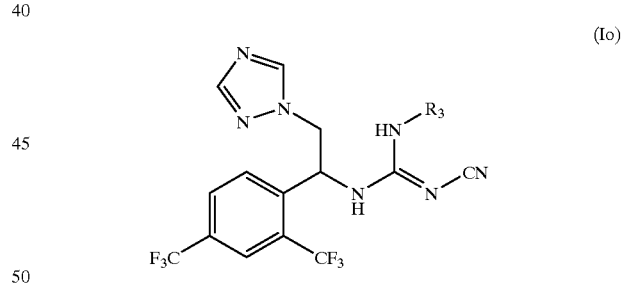

(Io)

Compounds having the formula (Io), wherein R₃ has the values listed in Table 10, were prepared by following the procedure described for Example 172, except different N-aryl-N'-cyanothioureas were used in the last step.

TABLE 10

| Example # | R₃ | Data |
|---|---|---|
| 173 | 4-bromo-2-methylphenyl | MS 560 [M + H]⁺ |

TABLE 10-continued

| Example # | R₃ | Data |
|---|---|---|
| 174 | | MS 559 [M + H]⁺ |
| 175 | | MS 507 [M + H]⁺ |

EXAMPLE 176

N-(3,4-Dichlorophenyl)-N'-[1-(2,4-bistrifluoromethylphenyl)-2-[benzimidazol-1-yl)]-ethyl]-N''-cyanoguanidine

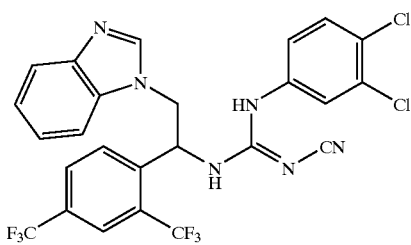

The procedure described for Example 172 was followed using benzimidazole instead of triazole to produce 1-(2,4-Bistrifluoromethylphenyl)-2-(benzimidazol-1-yl) ethylamine, and then this ethylamine was used in the last step to make Example 176. MS (ES): m/z 585 [M+H]⁺.

EXAMPLE 177

N-[1-(2,4-bistrifluoromethylphenyl)-[1-benzimidazolyl)]-ethyl]-N'-(indan-7-yl)-N''-cyanoguanidine

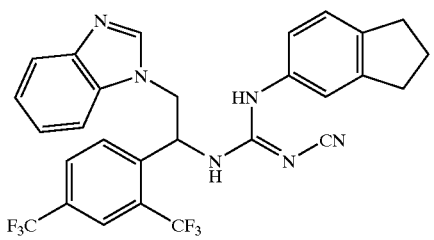

Example 177 was prepared in the same manner as for Example 176, except N-(indan-7-yl)-N'-cyanothiourea was used in the last step. MS (ES): m/z 556 [M+H]⁺.

EXAMPLES 178–180

N-(Disubstitutedphenyl)-N'-[1-(2,3-dichlorophenyl)-2-[1-(1,2,4-triazol-1-yl)]-ethyl]-N''-cyanoguanidines

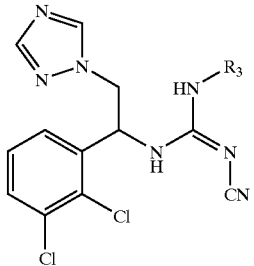

(Ip)

Compounds having the formula (Ip), wherein R₃ has the values listed in Table 11, were prepared by using the procedure described for Example 148 with triazole instead of imidazole to produce 1-(2,3-Dichlorophenyl)-2-[1-(1,2,4-triazolyl)]ethylaamine, and then this ethylamine was used in the last step with different N-aryl-N'-cyanothioureas to obtain the desired compound.

TABLE 11

| Example # | R₃ | Data |
|---|---|---|
| 178 | Cl, Cl phenyl | MS 469 [M + H]⁺ |
| 179 | Cl, CH₃ phenyl | MS 448 [M + H]⁺ |
| 180 | Cl, Cl phenyl | MS 469 [M + H]⁺ |

EXAMPLES 181–189

N-(Substitutedphenyl)-N'-[1-(2,4-dichlorophenyl)-2-(benzimidazol-1-yl)-ethyl]-N''-cyanoguanidines

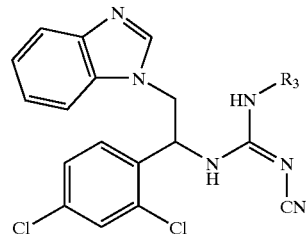

(Iq)

Compounds of formula (Iq), wherein R₃ has the values listed in Table 12, were prepared by first following the process described in Example 82, using benzimidazole instead of imidazole, to obtain 1-(2,4-Dichlorophenyl)-2-(benzimidazol-1-yl)ethylamine (as a white solid). Then this ethylamine was used in the last step with different cyanothioureas (e.g., Example 1, Step F), to obtain the desired compound.

TABLE 12

| Example # | R₃ | Data |
|---|---|---|
| 181 | (3,5-dichlorophenyl) | MS 518 [M + H]⁺ |
| 182 | (2-methyl-4-fluorophenyl) | MS 481 [M + H]⁺ |
| 183 | (2,4-dimethylphenyl) | MS 477 [M + H]⁺ |
| 184 | (indanyl) | MS 489 [M + H]⁺ |
| 185 | (2-chloro-4-methylphenyl) | MS 497 [M + H]⁺ |
| 186 | (2-methyl-4-chlorophenyl) | MS 497 [M + H]⁺ |
| 187 | (4-phenoxyphenyl) | MS 541 [M + H]⁺ |
| 188 | (2-methyl-4-bromophenyl) | MS 542 [M + H]⁺ |

TABLE 12-continued

| Example # | R₃ | Data |
|---|---|---|
| 189 | (3-benzyloxyphenyl) | MS 555 [M + H]⁺ |

EXAMPLE 190

N-[1-(2,4-Dichlorophenyl)-2-(imidazol-1-yl)-ethyl]-N'-diphenylmethyl-N"-(4-carbonylguanidine Hydrochloride

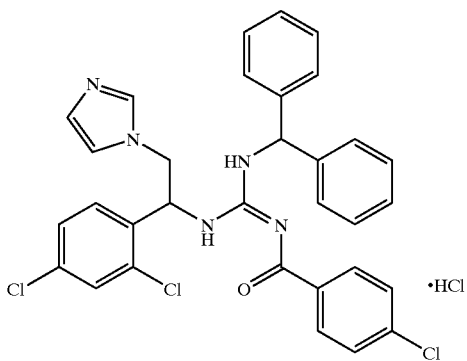

A. N-[1-(2,4-Dichlorophenyl)-2-(imidazol-1-yl)-ethyl]-N'-(4-chlorophenyl)carbonyl thiourea. To a stirred solution of 4-chlorobenzoyl chloride (175 mg, 1.0 mmol) in anhydrous acetone was added KNCS (100 mg, 1.0 mmol) at rt. The reaction mixture was heated at reflux for 40 min, then cooled to rt, and 1-(2,4-dichlorophenyl)-2-(imidazol-1-yl)ethylamine (250 mg, 1.0 mmol) was added. The reaction was allowed to proceed for 2 h. The precipitate was filtered and the filtrate concentrated to give Compound A, which was used in the next step without further purification.

B. N-[1-(2,4-Dichlorophenyl)-2-(imidazol-1-yl)-ethyl]-N'-diphenylmethyl-N"-(4-chlorophenyl)carbonylguanidine Hydrochloride. To a stirred solution of Compound A in CH₂Cl₂ was added diphenylmnethylamine (150 mg), followed by TEA and mercuric chloride (270 mg). The mixture was allowed to stir at rt for 3 h. The reaction mixture was diluted with EtOAc. The precipitate was filtered, the filtrate concentrated, and the residue purified by column chromatography (EtOAc, MeOH, NH₄OH; 90:10:0.1) to give, after conversion to HCl salt with HCl solution in ether, the titled compound a solid. MS (ES): m/z 602 [M+H]⁺.

EXAMPLE 191

N-[1-(2,4-Dichlorophenyl)-2-(imidazol-1-yl)-ethyl]-N'-phenyl-N''-phenylcarbonylguanidine

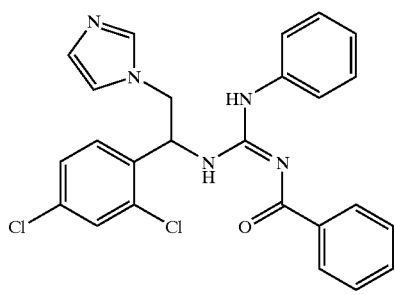

A. N-[1-(2,4-Dichlorophenyl)-2-(imidazol-1-yl)-ethyl]-N'-phenyl)carbonyl thiourea. Compound A was prepared by following the procedure of Example 190, Step A, except benzoyl chloride was used instead of 4-chlorobenzoyl chloride.

B. N-[1-(2,4-Dichlorophenyl)-2-(imidazol-1-yl)-ethyl]—N'-phenyl-N''-phenylcarbonylguanidine. Step B of Example 190 was followed using Compound A, above, and aniline (instead of diphenylmethylamine) to obtain Example 191. MS (ES): m/z 478 [M+H]+.

EXAMPLES 192–227

N-[1-(2,4-Dichlorophenyl)-2-(imidazol-1-yl)-ethyl]-N'-substituted-N''-phenylcarbonylguanidines

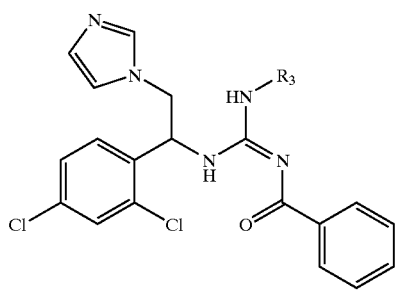

(Ir)

Compounds having the formula (If) wherein $R_3$ has the values listed in Table 13, were prepared by following the process described in Example 191 except using different arylamines in step B.

TABLE 13

| Example # | $R_3$ | Data |
|---|---|---|
| 192 | 3-Cl-phenyl | MS 512 [M + H]+ |
| 193 | 4-CH₃-phenyl | MS 492 [M + H]+ |
| 194 | 4-Cl-phenyl | MS 512 [M + H]+ |
| 195 | 2-Cl-5-CH₃-phenyl | MS 526 [M + H]+ |
| 196 | 2,4-diCl-phenyl | MS 547 [M + H]+ |
| 197 | 4-CN-phenyl | MS 503 [M + H]+ |
| 198 | 3,4-diCl-phenyl | MS 547 [M + H]+ |
| 199 | 4-CO₂CH₃-phenyl | MS 536 [M + H]+ |
| 200 | 4-CF₃-phenyl | MS 546 [M + H]+ |
| 201 | 4-Br-phenyl | MS 557 [M + H]+ |

TABLE 13-continued

| Example # | R₃ | Data |
|---|---|---|
| 202 | 4-chloro-3-methylphenyl | MS 526 [M + H]⁺ |
| 203 | 4-propylphenyl | MS 520 [M + H]⁺ |
| 204 | 4-cyclohexylphenyl | MS 560 [M + H]⁺ |
| 205 | 3-bromo-2-methylphenyl | MS 571 [M + H]⁺ |
| 206 | 4-phenylphenyl | MS 554 [M + H]⁺ |
| 207 | 4-(trifluoromethoxy)phenyl | MS 562 [M + H]⁺ |
| 208 | 4-acetylphenyl | MS 520 [M + H]⁺ |
| 209 | 4-(methylsulfonyl)phenyl | MS 556 [M + H]⁺ |
| 210 | 4-sulfamoylphenyl | MS 557 [M + H]⁺ |
| 211 | 4-phenoxyphenyl | MS 570 [M + H]⁺ |
| 212 | 4-(1,1,1,3,3,3-hexafluoro-2-hydroxypropan-2-yl)phenyl | MS 644 [M + H]⁺ |
| 213 | naphthalen-2-yl | MS 528 [M + H]⁺ |
| 214 | 4-(2-hydroxypropan-2-yl)phenyl | MS 536 [M + H]⁺ |
| 215 | 4-ethylphenyl | MS 506 [M + H]⁺ |
| 216 | 4-chloro-3-(trifluoromethyl)phenyl | MS 580 [M + H]⁺ |
| 217 | 4-tert-butyl-2,6-dimethylphenyl | MS 562 [M + H]⁺ |
| 218 | naphthalen-1-yl | MS 528 [M + H]⁺ |

TABLE 13-continued

| Example # | R₃ | Data |
|---|---|---|
| 219 | 4-(methylthio)phenyl | MS 524 [M + H]⁺ |
| 220 | 2-chloro-4-(phenyl(cyano)methyl)phenyl | MS 627 [M + H]⁺ |
| 221 | 4-(cyanomethyl)phenyl | MS 517 [M + H]⁺ |
| 222 | 2,3-dihydro-1H-inden-5-yl | MS 518 [M + H]⁺ |
| 223 | 4-chloro-3-nitrophenyl | MS 557 [M + H]⁺ |
| 224 | 4-(1-hydroxyethyl)phenyl | MS 522 [M + H]⁺ |
| 225 | 3,4,5-trichlorophenyl | MS 581 [M + H]⁺ |
| 226 | 4-isopropylphenyl | MS 520 [M + H]⁺ |
| 227 | 4-(pyridin-4-ylmethyl)phenyl | MS 569 [M + H]⁺ |

EXAMPLES 228–230

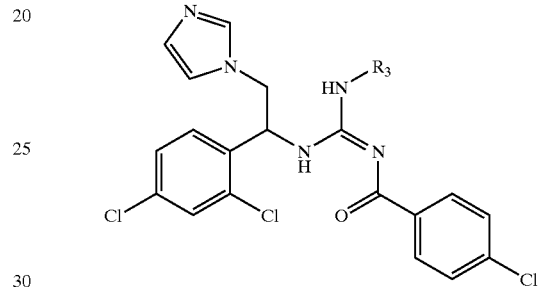

(Is)

Compounds having the formula (Is) wherein R₃ has the values listed in Table 14, were prepared by following the process described in Example 190 except using different arylamines in step B.

TABLE 14

| Example # | R₃ | Data |
|---|---|---|
| 228 | 4-chlorophenyl | MS 547 [M + H]⁺ |
| 229 | 4-bromophenyl | MS 591 [M + H]⁺ |

TABLE 14-continued

| Example # | R₃ | Data |
|---|---|---|
| 230 | 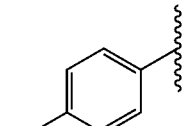 | MS 580 [M + H]⁺ |

EXAMPLE 231

N-[1-(2,4-Dichlorophenyl)-2-(imidazol-1-yl)-ethyl]-N'-(4-chlorophenyl)-N''-(4-cyanophenyl) carbonylguanidine hydrochloride

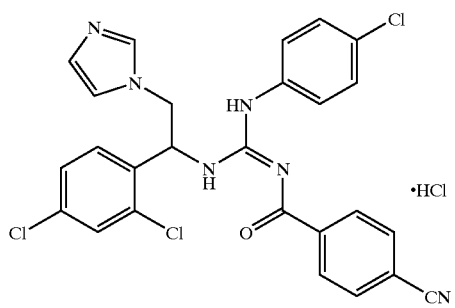

A. N-(4-Chlorophenyl)-N'-[1-(2,4-dichlorophenyl)-2-(imidazol-1-yl)-ethyl]thiourea. To a stirred solution of 1-(2,4-dichlorophenyl)-2-(imidazol-1-yl)ethylaruine (255 mg, 1.0 mmol) in acetonitrile was added 4-chlorophenylisothiocyanate (170 mg, 1.0 mmol). The reaction mixture was allowed to stir at rt for 18 h. The solvent was evaporated to give Compound A as a solid, which was used directly in the next step.

B. N-(4-Chlorophenyl)-N'-[1-(2,4-dichlorophenyl)-2-(imidazol-1-yl)-ethyl]guanidine. Compound A was mixed with a solution of ammonium hydroxide (10 mL, 7M) in MeOH. To this stirred solution was added mercuric oxide (red, 1.5 mmol). The suspension was allowed to stir at rt for 18 h. The mixture was filtered, and the filtrate concentrated and partitioned between aqueous NaOH solution and EtOAc. The organic layer was separated, dried, and concentrated to give Compound B as an oil.

C. N-[1-(2,4-Dichlorophenyl)-2-(imidazol-1-yl)-ethyl]-N'-(4-chlorophenyl)-N''-(4-cyanophenyl)carbonylguanidine hydrochloride. To a stirred solution of 4-cyanobenzoic acid (43 mg, 0.3 mmol) in 5 mL of anhydrous THF was added carbonyl diimidazole (48 mg, 0.3 mmol). This was allowed to stir at rt for 2 h. A solution of Compound B (120 mg, 0.3 mmol) in anhydrous THF (1 mL) was added, and the mixture was allowed to stir at rt for 18 h. The solvent was removed, and the residue partitioned between EtOAc and NaHCO₃ solution. The organic layer was separated, dried, and concentrated. The residue was purified by silica gel column chromatography (EtOAc, MeOH, NH₄OH; 90:10:0.1) to give an oil, which was dissolved in MeOH. HCl solution in ether was added, and the solvent was removed to give the title compound as a solid. MS (ES): m/z 537 [M+H]⁺.

EXAMPLES 232–271

N-[1-(2,4-Dichlorophenyl)-2-(imidazol-1-yl)-ethyl]-N'-(4-chlorophenyl)-N''-carbonylguanidines

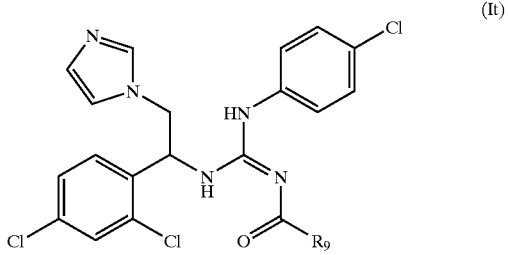

(It)

Compounds having the formula (It) wherein R₉ has the values listed in Table 15, were prepared by following the process described for Example 231 except instead of 4-cyanobenzoic acid, different carboxyclic acids were used in Step C.

TABLE 15

| Example # | R₉ | Data |
|---|---|---|
| 232 |  | MS 478 [M + H]⁺ |
| 233 | 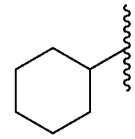 | MS 518 [M + H]⁺ |
| 234 | 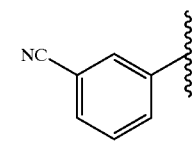 | MS 537 [M + H]⁺ |
| 235 | 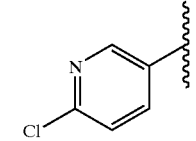 | MS 548 [M + H]⁺ |
| 236 |  | MS 677 [M + H]⁺ |
| 237 | 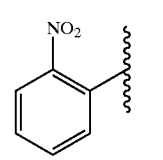 | MS 557 [M + H]⁺ |

TABLE 15-continued

| Example # | R$_9$ | Data |
|---|---|---|
| 238 | 2-methylphenyl | MS 526 [M + H]$^+$ |
| 239 | 2-fluorophenyl | MS 530 [M + H]$^+$ |
| 240 | 4-chloro-2-nitrophenyl | MS 592 [M + H]$^+$ |
| 241 | 3-methylphenyl | MS 526 [M + H]$^+$ |
| 242 | pyridin-3-yl | MS 513 [M + H]$^+$ |
| 243 | 3,5-dichlorophenyl | MS 581 [M + H]$^+$ |
| 244 | 3-chlorophenyl | MS 547 [M + H]$^+$ |
| 245 | 3-(methoxycarbonyl)phenyl | MS 570 [M + H]$^+$ |
| 246 | 3-fluorophenyl | MS 530 [M + H]$^+$ |
| 247 | 3-chloro-4-fluorophenyl | MS 565 [M + H]$^+$ |
| 248 | furan-2-yl | MS 502 [M + H]$^+$ |
| 249 | furan-3-yl | MS 502 [M + H]$^+$ |
| 250 | thiophen-2-yl | MS 518 [M + H]$^+$ |
| 252 | 3-(trifluoromethyl)phenyl | MS 580 [M + H]$^+$ |
| 252 | 2,3-dichloro-fluorophenyl | MS 565 [M + H]$^+$ |
| 253 | 3-(methylsulfonyl)phenyl | MS 590 [M + H]$^+$ |
| 254 | 3-chloro-4-hydroxyphenyl | MS 563 [M + H]$^+$ |
| 255 | 3-(dimethylamino)phenyl | MS 555 [M + H]$^+$ |
| 256 | 3-acetamidophenyl | MS 569 [M + H]$^+$ |

TABLE 15-continued

| Example # | R9 | Data |
|---|---|---|
| 257 | NC-phenyl (3-CN) | MS 537 [M + H]+ |
| 258 | NC-phenyl (3-CN) | MS 537 [M + H]+ |
| 259 | 3-methylthiophen-2-yl | MS 532 [M + H]+ |
| 260 | CH3-S-CH2- | MS 496 [M + H]+ |
| 261 | isopropyl | MS 464 [M + H]+ |
| 262 | cyclopentylmethyl | MS 518 [M + H]+ |
| 263 | ethoxymethyl | MS 494 [M + H]+ |
| 264 | (CH3)2N-CH2- | MS 493 [M + H]+ |
| 265 | cyclopentyl | MS 504 [M + H]+ |
| 266 | 1-methylcyclopropyl | MS 490 [M + H]+ |
| 267 | cyclopropyl | MS 476 [M + H]+ |
| 268 | H3CO-phenyl (4-OMe) | MS 542 [M + H]+ |

TABLE 15-continued

| Example # | R9 | Data |
|---|---|---|
| 269 | 2-methoxyphenyl | MS 542 [M + H]+ |
| 270 | 4-(dimethylamino)phenyl | MS 555 [M + H]+ |
| 271 | 4-ethoxyphenyl | MS 556 [M + H]+ |

EXAMPLE 272

N-[1-(2,4-Dichlorophenyl)-2-(imidazol-1-yl)-ethyl]-N'-(4-tert-butylcyclohexyl)-N''-(3-cyanophenylcarbonyl)guanidine

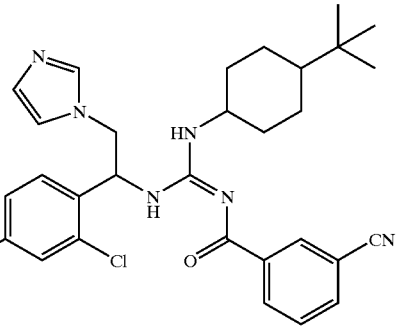

Example 272 was prepared by following the procedure of Example 190, except 3-cyanobenzoyl chloride was used instead of 4-chlorobenzoyl chloride in Step A to obtain N-[1-(2,4-Dichlorophenyl)-2-(imidazol-1-yl)-ethyl]-N'-(3-cyanophenyl)carbonyl thiourea, and tert-butylcyclohexylamine was used in Step B instead of diphenylmethylamine to obtain the titled compound. MS (ES): m/z 565 [M+H]+.

EXAMPLES 273–301

N-[1-(2,4-Dichlorophenyl)-2-(imidazol-1-yl)-ethyl]-
N'-(Substituted)-N"-(3-cyanophenylcarbonyl)
guanidines

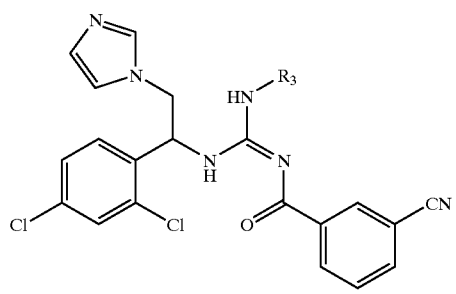

(Iu)

Compounds having the formula (Iu) wherein $R_3$ has the values listed in Table 16, were prepared by following the process described for Example 272 except different amines were used in Step B.

TABLE 16

| Example # | $R_3$ | Data |
|---|---|---|
| 273 | 4-(trifluoromethyl)phenyl | MS 571 [M + H]⁺ |
| 274 | 1-phenylethyl | MS 531 [M + H]⁺ |
| 275 | 2-benzyl-3-hydroxypropyl | MS 561 [M + H]⁺ |
| 276 | 2-(dimethylamino)ethyl | MS 498 [M + H]⁺ |
| 277 | 6-chloropyridin-3-yl | MS 538 [M + H]⁺ |
| 278 | 6-methoxypyridin-3-yl | MS 534 [M + H]⁺ |

TABLE 16-continued

| Example # | $R_3$ | Data |
|---|---|---|
| 279 | 3-methylisothiazol-5-yl | MS 524 [M + H]⁺ |
| 280 | 5-(trifluoromethyl)-1,3,4-thiadiazol-2-yl | MS 579 [M + H]⁺ |
| 281 | 3-methylisoxazol-5-yl | MS 508 [M + H]⁺ |
| 282 | 2-chloro-4-cyanophenyl | MS 562 [M + H]⁺ |
| 283 | 4-cyanophenyl | MS 528 [M + H]⁺ |
| 284 | 4-(methylthio)phenyl | MS 549 [M + H]⁺ |
| 285 | 2-(ethoxycarbonylmethyl)thiazol-4-yl | MS 596 [M + H]⁺ |
| 286 | 5-(ethylthio)-1,3,4-thiadiazol-2-yl | MS 571 [M + H]⁺ |
| 287 | 5-chlorothiazol-2-yl | MS 544 [M + H]⁺ |

TABLE 16-continued

| Example # | R₃ | Data |
|---|---|---|
| 288 | (isobenzofuranone, 5-yl) | MS 559 [M + H]⁺ |
| 289 | 3-phenyl-1,2,4-thiadiazol-5-yl | MS 587 [M + H]⁺ |
| 290 | benzothiazol-6-yl | MS 560 [M + H]⁺ |
| 291 | 1-ethyl-2-methylbenzimidazol-5-yl | MS 585 [M + H]⁺ |
| 292 | 5-tert-butylisoxazol-3-yl | MS 550 [M + H]⁺ |
| 293 | 4-(ethoxycarbonyl)-1H-pyrazol-3-yl | MS 565 [M + H]⁺ |
| 294 | 4-[(3,4-dimethylisoxazol-5-yl)sulfamoyl]phenyl | MS 677 [M + H]⁺ |
| 295 | 3-methyl-4-nitroisoxazol-5-yl | MS 553 [M + H]⁺ |
| 296 | 3,4-dimethylisoxazol-5-yl | MS 522 [M + H]⁺ |
| 297 | 2-methylbenzothiazol-5-yl | MS 574 [M + H]⁺ |
| 298 | 5,6-dihydro-4H-cyclopenta[d]thiazol-2-yl | MS 550 [M + H]⁺ |
| 299 | 3-(ethoxycarbonyl)-4-cyanoisoxazol-5-yl | MS 591 [M + H]⁺ |
| 300 | 3-tert-butylisoxazol-5-yl | MS 550 [M + H]⁺ |
| 301 | 3-phenylisoxazol-5-yl | MS 570 [M + H]⁺ |

EXAMPLE 302

N-(4-Chlorophenyl)-N'-[1-(2,4-dichlorophenyl)-2-(2-methylimidazol-1-yl-yl)-ethyl]-N"-(3-cyanophenylcarbonyl) guanidine

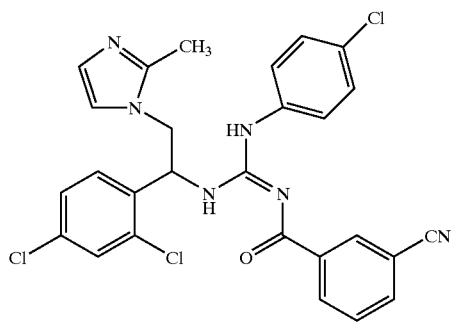

The procedure described in Example 1, Steps A–E, was followed except in Step C, trichloroacetophenone was used for Compound B and 2-methylimidazole was used instead of imidazole to prepare (after Step E), 1-(2,4-dichlorophenyl)-2-(2-methylimidazol-1-yl-yl)ethylamine. Then this ethylamine and 3-cyanobenzoic acid were used in the procedure described in Example 231, Steps A to B, to prepare the titled compound as a solid. MS (ES): mnz 551 [M+H]$^+$.

EXAMPLES 303–306

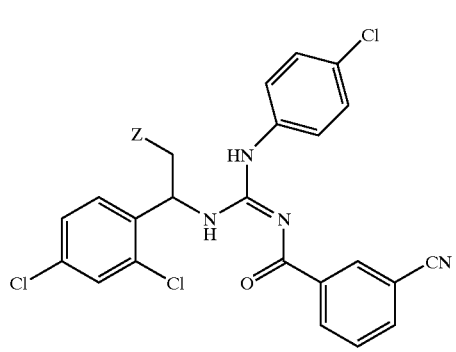

Compounds having the formula (Iv) wherein Z (or NR$_5$R$_6$ in Formula I) has the values listed in Table 17 were prepared by following the procedure described for Example 302, except instead of methylimidazole, different heteroaryls or substituted heteroaryls were used.

TABLE 17

| Example # | Z | Data |
|---|---|---|
| 303 | 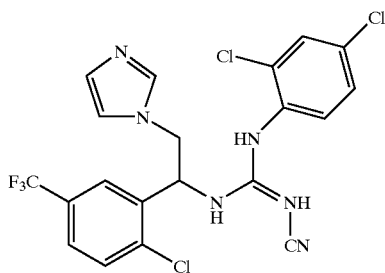 | MS 551 [M + H]$^+$ |

TABLE 17-continued

| Example # | Z | Data |
|---|---|---|
| 304 | benzimidazole | MS 587 [M + H]$^+$ |
| 305 | acetamido-ethyl-imidazole | MS 622 [M + H]$^+$ |
| 306 | triazole | MS 538 [M + H]$^+$ |

EXAMPLE 307

N-(2,4-Dichlorophenyl)-N'-[1-(2-chloro-5-trifluoromethylphenyl)-2-(imidazol-1-yl)-ethyl]-N"-cyanoguanidine A. 2-Chloro-5-trifluoromethylphenylethylene oxide. To a stirred solution of 2-chloro-5-trifluoromethylbenzalhyde (2.05 g, 10 mmol) in acetonitrile (50 mL) at rt was added trimethylsulfonium iodide (2.04 g, 10 mmol) and 0.5 mL of water, followed by powdered KOH (1.05 g). The suspension was heated on an oil-bath at 70° C. under argon for 6 h. The reaction mixture was cooled, ether was added, and the suspension was filtered. The filtrate was concentrated and the residue purified by flash column chromatography (hexanes/EtOAc, 9:1) to give Compound A as a yellow oil (1.8 g).

B. 1-(2-Chloro-5-trifluoromethylphenyl)-2-(imidazol-1-yl) ethanol. To a stirred solution of Compound A (600 mg, 2.7 mmol) and imidazole (550 mg, 8 mmol) in DMF at rt was added sodium hydride (200 mg, 8 mmol) in one portion. This was allowed to stir at rt for 2 h. The reaction mixture was partitioned between EtOAc and water. The organic layer was separated, washed with saturated ammonium chloride solution, dried, and concentrated to give Compound B as an oil, which was used directly in the next step.

C. N-(2,4-Dichlorophenyl)-N'-[1-(2-chloro-5-trifluoromethylphenyl)-2-(imidazol-1-yl)-ethyl]-N"-cyanoguanidine. Step E of Example 1 was followed with t-(2-chloro-5-trifuoromethylphenyl)-2-(imidazol-1-yl) ethanol to prepare 1-(2-Chloro-5-trifuoromethylphenyl)-2-(imidazol-1-yl)ethylamine, and then this ethylamine was used in Step F of Example 1 to produce Example 307. MS (ES): m/z 501 [M+H]+.

EXAMPLE 308

N-(2,4-Dichlorophenyl)-N'-[1-(2,5-bistrifluoromethylphenyl)-2-(benzimidazol-1-yl)-ethyl]-N"-cyanoguanidine

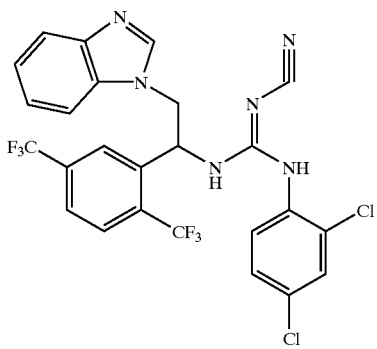

The procedure described for Example 307 was followed except in Step A, 2,5-bistrifluoromethylbenzadehyde was used to give 2,5-Bistrifluoromethylphenylethylene oxide. Step B gave bistrifuoromethylphenyl)-2-(benzimidazol-1-yl)ethanol, which was used in Step C to give 1-(2-Chloro-5-trifuoromethylphenyl)-2-(benzimidazol-1-yl)ethylamine and Example 308. MS (ES): m/z 585 [M+H]+.

EXAMPLE 309

N-[1-(2,4-Dichlorophenyl)-2-(imidazol-1-yl)-ethyl]-N'-(4-trifluoromethylphenyl)-N"-(pyridin-3-ylamino)carbonylguanidine dihydrochloride

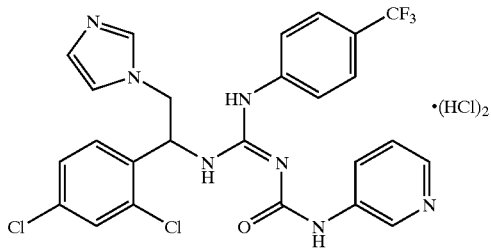

A. N-(4-Trifluoromethylphenyl)-N'-[1-(2,4-dichlorophenyl)-2-(imidazol-1-yl)-ethyl]thiourea. Compound A was prepared by following the procedure of Example 231, except 4-trifluoromethylphenylisothiocyanate was used.

B. N-(4-Chlorophenyl)-N'-[1-(2,4-dichlorophenyl)-2-(irmdazol-1-yl)-ethyl] guanidine. Compound B was prepared by following the procedure of Example 231, Step B, except the thiourea used was Compound A.

C. N-[1-(2,4-Dichlorophenyl)-2-(imidazol-1-yl)-ethyl]-N'-(4-trifluoromethylphenyl)-N"-(pyridin-3-ylamino) carbonylguanidine dihydrochloride. To a stirred solution of 3-aminopyridine (200 mg, 2.2 mmol) in 5 mL of anhydrous acetonitrile was added carbonyl diimidazole (330 mg, 2.2 mmol). This was allowed to stir at rt for 2 h. A solution of Compound B (700 mg, 1.5 mmol) in anhydrous acetonitrile (1 mL) was added. This was allowed to stir at rt for 18 h. The solvent was removed and the residue partitioned between EtOAc and NaHCO$_3$ solution. The organic layer was separated, dried, and concentrated; the residue was purified by silica gel column chromatography (EtOAc, MeOH, NH$_4$OH; 90:10:0.1) to give an oil. The oil was dissolved in MeOH, and to this was added HCT solution in ether. The solvent was removed to give the titled compound as a solid. MS (ES): nmz 562 [M+H]+.

EXAMPLES 310–313

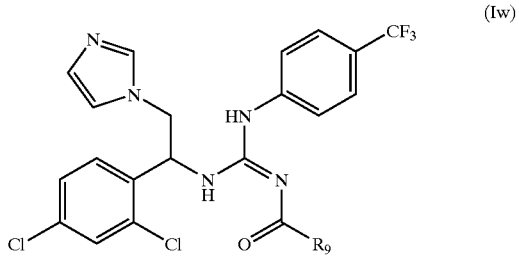

(Iw)

Coumpounds having the formula (Iw) wherein R$_9$ has the values listed in Table 18 were prepared by following the procedure described for Example 309, except in Step C, different amines were used instead of 3-aminopyridine.

TABLE 18

| Example # | R$_9$ | Data |
|---|---|---|
| 310 | morpholine-N-yl | MS 555 [M + H]+ |
| 311 | 4-methylpiperazin-1-yl | MS 568 [M + H]+ |
| 312 | bis(2-methoxyethyl)amino | MS 601 [M + H]+ |
| 313 | 2-(pyridin-2-yl)ethylamino | MS 590 [M + H]+ |

EXAMPLE 314

N-[1-(2,4-Dichlorophenyl)-2-(imidazol-1-yl)-ethyl]-N'-(4-chlorophenyl)-N''-(4-chlorophenylmethylamino)carbonylguanidine [Hydrochloride?]

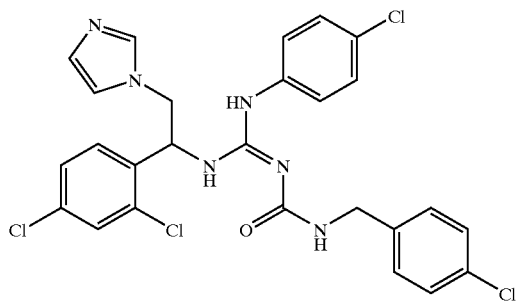

To a stirred solution of N-[1-(2,4-dichlorophenyl)-2-(imidazol-1-yl)-ethyl]-N'-(4-chlorophenyl)guanidine of Example 231 (step B) in THF was added carbonyldimidazole. The reaction mixture was allowed to stir at rt for 2 h, then 4-chlorophenylmethylamine was added. This was allowed to stir at rt for 18 h. The solvent was removed and the residue partitioned between EtOAc and ammonium chloride solution. The organic layer was separated, dried, concentrated, and purified by silica gel column chromatography (EtOAc, MeOH, NH$_4$OH; 90:10:0.1) to give an oil. The oil was dissolved in MEOH, and to this was added HCl solution in ether. The solvent was removed to give the title compound as a solid. MS (ES): r/z 576 [M+H]$^+$.

EXAMPLES 315–386

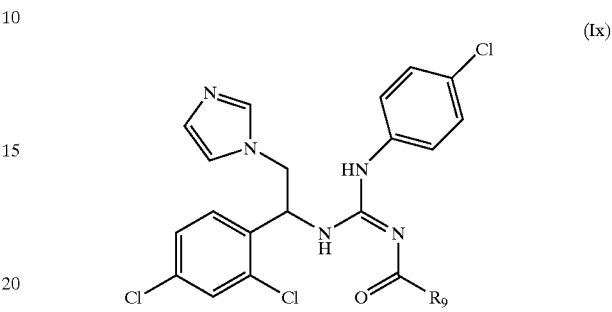

(Ix)

Compounds having the formula (1x) wherein R$_9$ has the values listed in Table 19 were prepared by following the procedure described for Example 314 except instead of 4-chlorophenylmethylamine, different amines were used.

TABLE 19

| Example # | R$_9$ | Data |
|---|---|---|
| 315 | (tetrahydropyridinyl) | MS 517 [M + H]$^+$ |
| 316 | (N-isopropyl-cyclohexyl) | MS 575 [M + H]$^+$ |
| 317 | (N-methyl-anthracenylmethyl) | MS 641 [M + H]$^+$ |
| 318 | (N-propyl-cyclopropylmethyl) | MS 547 [M + H]$^+$ |

TABLE 19-continued
| Example # | R9 | Data |
|---|---|---|
| 319 | 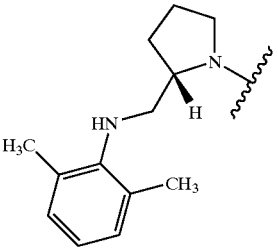 | MS 639 [M + H]+ |
| 320 | 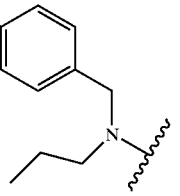 | MS 628 [M + H]+ |
| 321 | 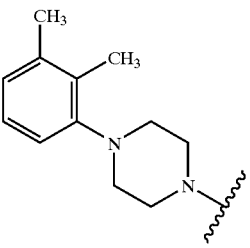 | MS 624 [M + H]+ |
| 322 | 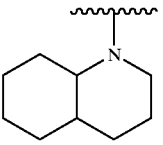 | MS 573 [M + H]+ |
| 323 | 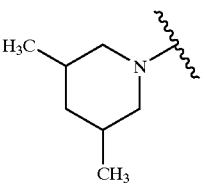 | MS 547 [M + H]+ |
| 324 | 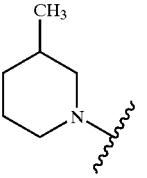 | MS 533 [M + H]+ |
| 325 | 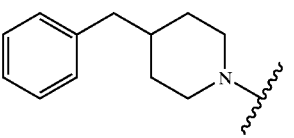 | MS 609 [M + H]+ |

TABLE 19-continued
| Example # | R9 | Data |
|---|---|---|
| 326 | 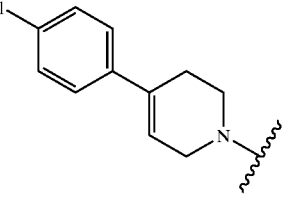 | MS 628 [M + H]+ |
| 327 | 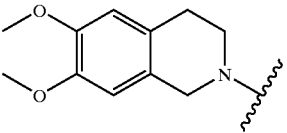 | MS 627 [M + H]+ |
| 328 | 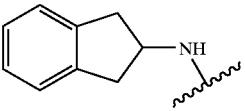 | MS 567 [M + H]+ |
| 329 | 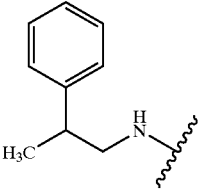 | MS 569 [M + H]+ |
| 330 | 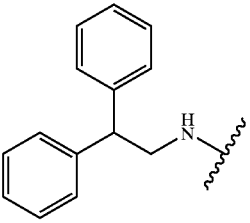 | MS 631 [M + H]+ |
| 331 | 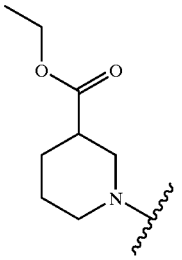 | MS 591 [M + H]+ |
| 332 | 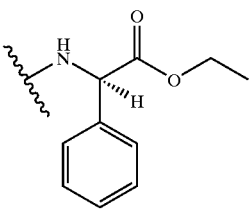 | MS 613 [M + H]+ |

TABLE 19-continued
| Example # | R9 | Data |
|---|---|---|
| 333 | 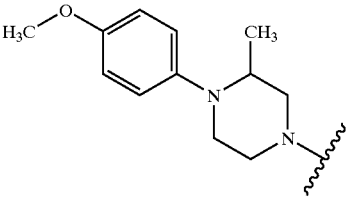 | MS 640 [M + H]+ |
| 334 | 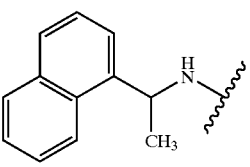 | MS 605 [M + H]+ |
| 335 | 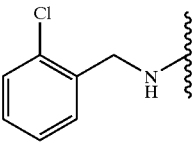 | MS 575 [M + H]+ |
| 336 | 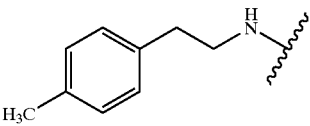 | MS 569 [M + H]+ |
| 337 | 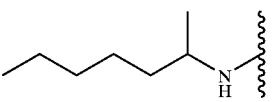 | MS 549 [M + H]+ |
| 338 | 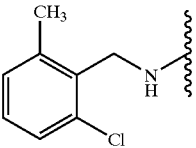 | MS 589 [M + H]+ |
| 339 | 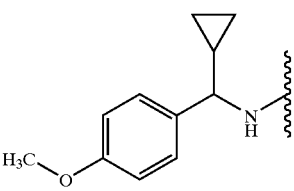 | MS 611 [M + H]+ |
| 340 | 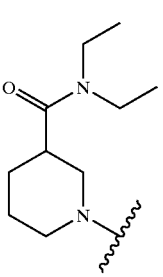 | MS 618 [M + H]+ |

TABLE 19-continued

| Example # | R₉ | Data |
|---|---|---|
| 341 | 3-methylphenyl-N(ethyl)-CH₂CH₂-NH- | MS 612 [M + H]⁺ |
| 342 | PhCH₂CH₂CH₂-NH- | MS 569 [M + H]⁺ |
| 343 | 2-fluoro-4-chlorobenzyl-NH- | MS 593 [M + H]⁺ |
| 344 | 2,4-dichlorophenethyl-NH- | MS 623 [M + H]⁺ |
| 345 | 1-(2,3-dihydro-1,4-benzodioxin-6-yl)-2-phenoxyethyl-NH- | MS 705 [M + H]⁺ |
| 346 | 2-methoxyphenethyl-NH- | MS 585 [M + H]⁺ |
| 347 | 2-(pyridin-2-yl)ethyl-N(propyl)- | MS 584 [M + H]⁺ |
| 348 | cyclopentyl-NH- | MS 519 [M + H]⁺ |

TABLE 19-continued

| Example # | R₉ | Data |
|---|---|---|
| 349 | pentyl-NH- | MS 535 [M + H]⁺ |
| 350 | 2-fluorobenzyl-NH- | MS 559 [M + H]⁺ |
| 351 | 3-methylbenzyl-NH- | MS 555 [M + H]⁺ |
| 352 | 1-phenyl-1,3,8-triazaspiro[4.5]decan-4-one-8-yl | MS 665 [M + H]⁺ |
| 353 | 1-(3,4-dimethoxyphenyl)-2-phenylethyl-NH- | MS 691 [M + H]⁺ |
| 354 | 2,6-difluorobenzyl-NH- | MS 577 [M + H]⁺ |
| 355 | 2-(cyclohex-1-en-1-yl)ethyl-NH- | MS 559 [M + H]⁺ |
| 356 | cyclohexylmethyl-NH- | MS 547 [M + H]⁺ |

TABLE 19-continued

| Example # | R₉ | Data |
|---|---|---|
| 357 | naphthyl-NHC(O)CH(CH₃)NH- | MS 648 [M + H]⁺ |
| 358 | benzyl-NH- | MS 541 [M + H]⁺ |
| 359 | (thiophen-2-yl)methyl-NH- | MS 547 [M + H]⁺ |
| 360 | trans-2-phenylcyclopropyl-NH- | MS 567 [M + H]⁺ |
| 361 | PhN(CH₃)CH₂CH₂CH₂NH- | MS 598 [M + H]⁺ |
| 362 | 3-methoxyphenethyl-NH- | MS 585 [M + H]⁺ |
| 363 | 4-methoxyphenethyl-NH- | MS 585 [M + H]⁺ |
| 364 | (5-methylfuran-2-yl)methyl-NH- | MS 545 [M + H]⁺ |
| 365 | 4-(2-oxo-2,3-dihydro-1H-benzimidazol-1-yl)piperidin-1-yl- | MS 651 [M + H]⁺ |

TABLE 19-continued

| Example # | R$_9$ | Data |
|---|---|---|
| 366 | 2-aminobenzyl-NH- | MS 556 [M + H]$^+$ |
| 367 | 2,6-dimethoxybenzyl-NH- | MS 601 [M + H]$^+$ |
| 368 | 2-(5-methoxy-1H-indol-3-yl)ethyl-NH- | MS 624 [M + H]$^+$ |
| 369 | N-(4-methoxynaphthalen-2-yl)-3-aminopropanamide | MS 678 [M + H]$^+$ |
| 370 | ethoxycarbonylmethyl-N(CH$_3$)- | MS 551 [M + H]$^+$ |
| 371 | 4-(1,2,3-thiadiazol-4-yl)benzyl-NH- | MS 625 [M + H]$^+$ |
| 372 | 1-(ethoxycarbonyl)piperidin-4-yl-NH- | MS 592 [M + H]$^+$ |
| 373 | 4-ethoxy-4-oxobutyl-NH- | MS 565 [M + H]$^+$ |

TABLE 19-continued

| Example # | R₉ | Data |
|---|---|---|
| 374 | tetrahydrofuran-2-ylmethyl-NH- | MS 535 [M + H]⁺ |
| 375 | 3-amino-hexahydroazepin-2-one-NH- | MS 562 [M + H]⁺ |
| 376 | (1H-benzimidazol-2-yl)methyl-NH- | MS 581 [M + H]⁺ |
| 377 | quinuclidin-3-yl- | MS 545 [M + H]⁺ |
| 378 | 1-(3-aminopropyl)pyrrolidin-2-one- | MS 576 [M + H]⁺ |
| 379 | 2-(pyridin-2-yl)ethyl-NH- | MS 556 [M + H]⁺ |
| 380 | 2-(pyridin-3-yl)ethyl-NH- | MS 556 [M + H]⁺ |
| 381 | 3-(imidazol-1-yl)propyl-NH- | MS 559 [M + H]⁺ |
| 382 | 6-(dimethylamino)hexyl-NH- | MS 578 [M + H]⁺ |
| 383 | 2-(pyridin-4-yl)ethyl-NH- | MS 556 [M + H]⁺ |
| 384 | 4-hydroxybutyl-NH- | MS 523 [M + H]⁺ |

TABLE 19-continued

| Example # | R9 | Data |
|---|---|---|
| 385 | (1-methylpiperidin-4-yl)(methyl)amino group | MS 562 [M + H]+ |
| 386 | 2-(dimethylamino)ethyl(ethyl)amino group | MS 550 [M + H]+ |

EXAMPLES 387 AND 388

(S)-N-[1-(2,4-Dichlorophenyl)-2-(imidazol-1-yl)-ethyl]-N'-(4-chlorophenyl)-N"-(4-cyanophenyl) carbonylguanidine Hydrochloride (Ex. 387) and (R)-N-[1-(2,4-Dichlorophenyl)-2-(imidazol-1-yl)-ethyl]-N'-(4-chlorophenyl)-N"-(4-cyanophenyl) carbonylguanidine Hydrochloride (Ex. 388)

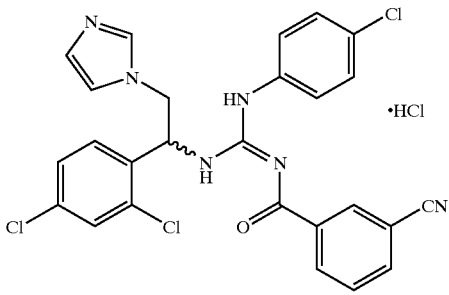

A. (R) and (S)-2-Chloro-1-(2,4-dichlorophenyl)ethanol. To a stirred solution of DIP-Cl (15 g, 46.8 mmol) in THF (100 mL) at −78° C. under argon atmosphere was added chloroacetophenone (5.5 g, 24.6 mmol) in THF (10 mL) via an additional funnel. This was allowed to stir at −78° C. and slowly warmed to rt for 18 h. To the resulting mixture was added MeOH (10 mL) followed by saturated NaHCO$_3$ solution. The mixture was concentrated and the residue partitioned between EtOAc and saturated NaHCO$_3$ solution. The organic layer was separated, dried, and concentrated, and the residue was purified by silica gel column chromatography (8:1, hexanes/EtOAc) to give Compound A as an oil (5 g, 90%). The R-enantiomer was made by starting with (−) DIP-Cl (to give Ex. 387), and the S-enantiomer with (+) DIP-Cl (Ex. 388).

B. (R) and (S)-1-(2,4-Dichlorophenyl)-(imidazol-1-yl) ethanol. To a stirred solution of Compound A (5.0 g, 22.2 mmol) in DMF was added imidazole (2.0 g, 29.4 mmol). This was cooled to 0° C., and sodium hydride (1.0 g, 42 mmol) was added. The resultant mnixture was allowed to stir at 0° C. for 2 h and at rt for 18 h. The reaction was quenched with water (10 mL), and resultant mixture was partitioned between water and EtOAc. The organic layer was separated, dried, concentrated, and the residue was purified by column chromatography (EtOAc, MeOH, NH$_4$OH; 90:10:0.1) to give Compound B as a solid (4.0 g, 70%).

C. (S) and (R)-1-(2,4-Dichlorophenyl)-2-(imidazol-1-yl) ethylamine. Step E of Example 1 was followed to obtain Compound C except 1-(2,4-dichlorophenyl)-(imidazol-1-yl) ethanol was used.

D. (S) and (R)-N-[1-(2,4-Dichlorophenyl)-2-(imidazol-1-yl)-ethyl]-N'-(4-chlorophenyl)-N"-(4-cyanophenyl) carbonylguanidine hydrochloride. Steps A-C of Example 231 were followed to obtain the Compound of Examples 387 and 388 as a white solid, except in Step A, 1-(2,4-Dichlorophenyl)-2-(imidazol-1-yl)ethylamine was used and in Step C$_{1-3}$-cyanobenzoic acid. The S-enantiomer was made by starting with (−) DIP-Cl, and the R-enantiomer with (+) DIP-Cl. MS (ES): m/z 537 [M+H]+.

EXAMPLE 389

N-(Diphenylmethyl)-N'-[1-(2,4-dichlorophenyl)-2-(imidazol-1-yl) ethyl]-N"-(thiazol-2-yl)guanidine hydrochloride

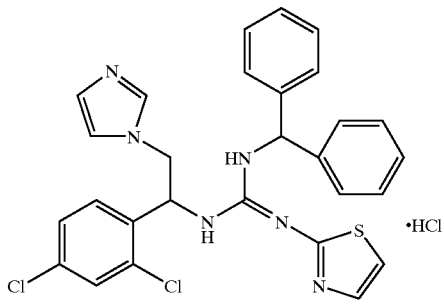

To a stirred solution of 2-aminothiazole (100 mg) in acetonitrile (3 mL) was added thiocarbonyl dimidazole (180 mg, 1.0 mmol). The mixture was allowed to stir at rt for 2 h and at 65° C. for 5 h, and then 1-(2,4-dichlorophenyl)-2-(imidazol-1-yl)ethylamine (250 mg, 1.0 mmol) was added. This was allowed to stir for 5 h at 65° C. The mixture was cooled to rt, and diphenylmethylamine was added, followed by TEA and mercuric chloride. The suspension was allowed to stir at rt for 3 h and filtered. The filtrate was concentrated and the residue purified by column chromatography (EtOAc, MeOH, NH$_4$OH; 90:10:0.1) to give after conversion to HCT salt, the title compound as a yellow solid (100 mg). MS (ES): m/z 547 [M+H]$^+$.

EXAMPLE 390

N-(4-chlorophenyl)-N'-[1-(2,4-dichlorophenyl)-2-(imidazol-1-yl)ethyl]-N''-(pyridin-4-ylcarbonyl) guanidine hydrochloride

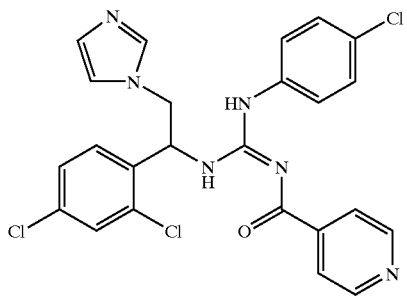

To a stirred solution of isoniconamide (150 mg, 1.2 mmol) in DMF (3 mL) at rt was added sodium hydride (60% in oil, 120 mg, 3.0 mmol). After the mixture was allowed to stir at rt for 2 h, 4-chlorophenylthioisocyanate was added, and then it was allowed to stir for an additional 2 h. 1-(2,4-Dichlorophenyl)-2-(imidazol-1-yl)ethylamine (200 mg, 0.78 mmol) was added, followed by mercuric chloride (300 mg). The suspension was allowed to stir at rt for 3 h, diluted with EtOAc, and filtered. The filtrate was concentrated, and the residue was purified by column chromatography (EtOAc, MeOH, NH$_4$OH; 90:10:0.1) to give, after conversion to HCl salt, the title compound as a yellow solid (190 mg). MS (ES): m/z 513 [M+H]$^+$.

EXAMPLES 391–395

N-(Substituted phenyl)-N'-[1-(2,4-dichlorophenyl)-2-(imidazol-1-yl)ethyl]-N''-(aminocarbonyl) guanidines (Iy)

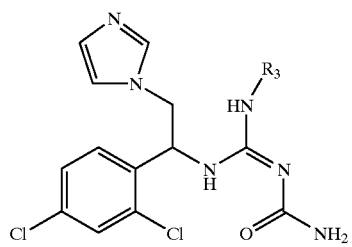

The compounds having the formula (Iy) wherein R$_3$ has the values listed in Table 20 were prepared by following the procedure described for Example 390 except urea was used in place of isoniconamide, and different arylisothiocyanates were used in place of 4-chlorophenylthioisocyanate (e.g., 2-bromo-4-chlorophenylisothiocyanate was used for Example 391).

TABLE 20

| Example # | R$_3$ | Data |
|---|---|---|
| 391 | Br, Cl substituted phenyl | MS 529 [M + H]$^+$ |
| 392 | Br substituted biphenyl | MS 571 [M + H]$^+$ |
| 393 | Cl, Cl substituted phenyl | MS 485 [M + H]$^+$ |
| 394 | Cl, Cl, Cl substituted phenyl | MS 519 [M + H]$^+$ |
| 395 | Cl substituted phenyl | MS 451 [M + H]$^+$ |

EXAMPLE 396

N-(2,4-Dichlorophenyl)-N'-[1-(2,4-dichlorophenyl)-2-(imidazol-1-yl)ethyl]-N''-(4-nitrophenylsulfonyl) guanidine

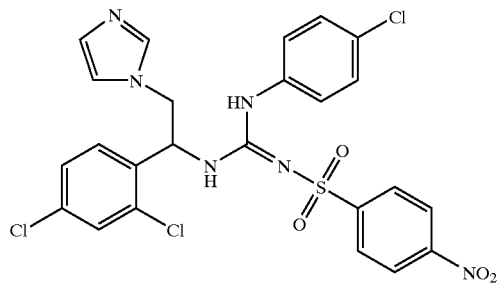

The titled compound was prepared by following the procedure of Example 390 except 4-nitrophenylsulfonamide was used instead of isoniconamide. MS (ES): m/z 593 [M+H]$^+$.

EXAMPLE 397

N-(2,4-Dichlorophenyl)-N'-[1-(2,4-dichlorophenyl)-2-(imidazol-1-yl)ethyl]-N"-(dimethylaminocarbonyl)guanidine

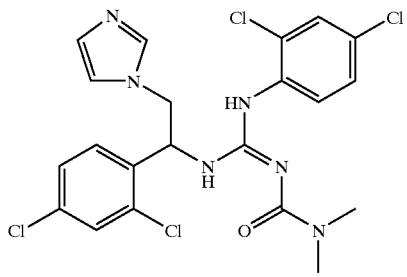

The titled compound was prepared by following the procedure of Example 390 except N,N-dimethylurea was used instead of isoniconamide and 2,4-dichlorophenylisothiocyanate was used instead of 4-chlorophenylthioisocyanate. MS (ES): m/z 513 [M+H]$^+$.

EXAMPLE 398

N-(2,4-Dichlorophneyl)-N'-[1-(2,4-dichlorophenyl)-2-(imidazol-1-yl)ethyl]-N"-(n-butylaminocarbonyl)guanidine

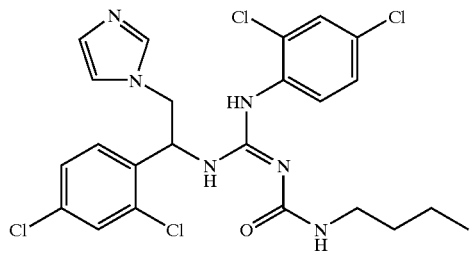

A. N-(2,4-Dichlorophenyl)-N'-[1-(2,4-dichlorophenyl)-2-(imidazol-1-yl)ethyl] guanidine. Compound A was prepared by following Example 231, Step A, except 2,4-dichlorophenylisothiocyanate was used.

B. N-(2,4-Dichlorophenyl)-N'-[1-(2,4-dichlorophenyl)-2-(imidazol-1-yl)ethyl] N"-(n-butylaminocarb The title compound was prepared by following the procedure of Example 314, except N-(2,4-dichlorophenyl)-N'-[1-(2,4-dichlorophenyl)-2-(imidazol-1-yl)ethyl] guanidine was used as the guanidine source and n-butylamine was used in place of 4-chlorophenylmethylamine. MS (ES): m/z 541 [M+H]$^+$.

EXAMPLES 399–400

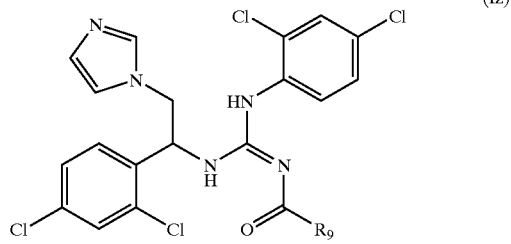

Compounds having the formula (Iz) wherein R$_9$ has the values listed in Table 21 were prepared by following the procedure of Example 398 except different amines were used instead of n-butylamine.

TABLE 21

| Example # | R$_9$ | Data |
|---|---|---|
| 399 | 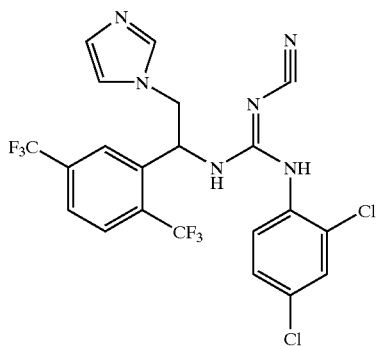 | MS 555 [M + H]$^+$ |
| 400 | | MS 556 [M + H]$^+$ |

EXAMPLE 401

N-(2,4-Dichlorophenyl)-N'-[-(2,5-bistrifluoromethylphenyl)-2-(imidazol-N-yl)-ethyl]-N"-cyanoguanidine A. 1-(2,5-Bistrifuoromethylphenyl)-2-(benzimidazol-2-yl)ethylamine. To a stirred solution of 1,1,1,3,3,3-hexamethyldisilazane (2.91 mL, 13.8 mmol, 1.11 equiv) in 13 mL anhydrous THF at 0° C. was added n-butyllithium (5.20 mL of a 2.5 M solution in hexane, 13.0 mmol, 1.05 equiv). After 15 min, 2,5-bistrifluoromethylbenzaldehyde (2.04 g, 8.43 mmol) in anhydrous THF (4 mL) at 0° C. was slowly added, followed by chlorotrimethylsilane (1.73 mL, 1.6 mmol, 1.10 equiv). The mixture was partitioned between EtOAc and water, and the organic layer was washed with brine (3×50 mL), dried (Na$_2$SO$_4$), and concentrated to give Compound A as a solid.

B. N-(2,4-Dichlorophenyl)-N'-[1-(2,5-bistrifluoromethylphenyl)-2-(imidazol-1-yl)-ethyl]-N"-cyanoguanidine. To a stirred solution of 1-(2,5-bistrifuoromethylphenyl)-2-(imidazol-1-yl)ethylamine (1.1 g, 3.4 mmol) in DMF at rt, N-cyano-N'-(2,4-dichlorophenyl)thiourea (1.1 g, 4.1 mmol) was added, followed by N-(3-dimethylaminopropyl)-N'-ethylcarbodiimide (800 mg, 4.1 mmol). The mixture was allowed to stir at rt for 18 h and then partitioned between EtOAc and saturated ammonium chloride solution. The organic layer was separated and washed with saturated ammonium chloride solution (3×50 mL). The organic layer was dried and concentrated, and the residue was purified by silica gel column chromatography (EtOAc, MeOH, NH$_4$OH; 95:5:0.1) to give a solid (350 mg). MS (ES): m/z 535 [M+H]$^+$.

EXAMPLES 402–430

N-[1-(2,4-Dichlorophenyl)-2-(imidazol-1-yl)-ethyl]-
N'-(4-chlorophenyl)-N''-(substituted)
carbonylguanidines

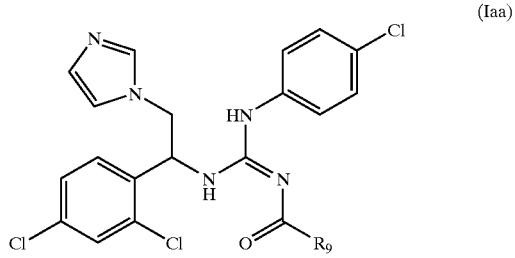
(Iaa)

Compounds having the formula (Iaa) wherein $R_9$ has the values listed in Table 22 were prepared following the same or similar procedure as for Example 390, except instead of isoniconamide, different ureas were used.

TABLE 22

| Example # | $R_9$ | Appearance | Data |
|---|---|---|---|
| 402 | Cl,Cl-cyclopropyl | White solid | $^1$H NMR (400 MHz, MeOD) δ 1.4 (1H, m), 1.50 (3H, m), 2.15 (1H, dd, J = 16.0, 8.0 Hz), 4.7 (2H, m), 6.0 (1H, m), 7.2–7.7 (9H, m), 8.95 (1H, s). |
| 403 | methylthiophene | White powder | MS 532 |
| 404 | methylthiomethyl | Yellow oil | MS 496 |
| 405 | propyl | | MS 464 |
| 406 | cyclopentylmethyl | | MS 518 |
| 407 | ethoxymethyl | | MS 494 |
| 408 | dimethylaminomethyl | | MS 493 |

TABLE 22-continued

| Example # | $R_9$ | Appearance | Data |
|---|---|---|---|
| 409 | cyclopentyl | | MS 504 |
| 410 | 1,1-dimethylcyclopropyl | | MS 490 |
| 411 | cyclopropyl | | MS 476 |
| 412 | 4-methoxyphenyl | | MS 542 |
| 413 | 2-methoxyphenyl | | MS 542 |
| 414 | 4-(dimethylamino)phenyl | | MS 555 |
| 415 | 3-(dimethylamino)phenyl | | MS 555 |
| 416 | 4-ethoxyphenyl | | MS 556 |
| 417 | neopentyl | White solid | MS 506 |
| 418 | tert-butyl | White solid | MS 492 |

TABLE 22-continued

| Example # | R$_9$ | Appearance | Data |
|---|---|---|---|
| 419 | (2,2-dimethyl-3-hydroxypropyl) | Pale yellow oil | MS 508 |
| 420 | (1-cyanocyclopropyl) | Colorless oil | MS 501 |
| 421 | (cyclopropylmethyl) | White solid | MS 490 |
| 422 | (cyclobutyl) | White solid | MS 490 |
| 423 | (2-methylcyclopropyl) | White solid | MS 490 |
| 424 | (3-acetyl-2,2-dimethylcyclobutylmethyl) | Yellow oil | MS 574 |
| 425 | (2,2,3,3-tetramethylcyclopropyl) | Yellow oil | MS 532 |
| 426 | (1-(4-chlorophenyl)cyclopropyl) | Yellow oil | MS 586 |
| 427 | (2,2-dimethyl-3-(2-methylprop-1-enyl)cyclopropyl) | Yellow oil | MS 558 |
| 428 | (2-(1,1-dichlorocyclopropyl)) | White solid | MS 544 |
| 429 | (1-(tert-butoxycarbonylamino)cyclopropyl) | White solid | MS 591 |
| 430 | (2,2-dichloro-1-methylcyclopropyl) | White solid | MS 558 |

EXAMPLES 431–448

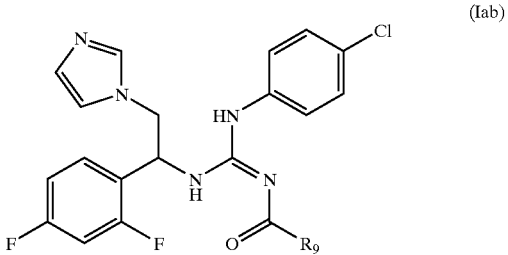
(Iab)

Compounds having the formula (Iab) wherein R$_9$ has the values listed in Table 23 were prepared following the same or similar procedure as Example 390, except the ethylamine added was 1-(2,4-difluorophenyl)-2-(imidazol-1-yl)ethylamine, and different ureas were used instead of isoniconamide.

TABLE 23

| Example # | R$_9$ | Data |
|---|---|---|
| 431 | (acetoxymethyl) | MS 475 |
| 432 | (3-cyanophenyl) | MS 504 |

TABLE 23-continued

| Example # | R₉ | Data |
|---|---|---|
| 433 | ethyl | MS 431 |
| 434 | cyclopentylmethyl | MS 485 |
| 435 | ethoxymethyl | MS 461 |
| 436 | (dimethylamino)ethyl | MS 460 |
| 437 | methoxyethyl | MS 447 |
| 438 | cyclopentyl | MS 471 |
| 439 | 1-methylcyclopropyl | MS 457 |
| 440 | cyclopropyl | MS 443 |
| 441 | (methylthio)methyl | MS 463 |
| 442 | thiophen-2-yl | MS 485 |
| 443 | 1-methyl-1H-pyrrol-2-yl | MS 482 |
| 444 | 4-methoxyphenyl | MS 509 |

TABLE 23-continued

| Example # | R₉ | Data |
|---|---|---|
| 445 | 3-methoxyphenyl | MS 509 |
| 446 | 2-methoxyphenyl | MS 509 |
| 447 | 3-(dimethylamino)phenyl | MS 523 |
| 448 | 4-ethoxyphenyl | MS 524 |

EXAMPLES 449–456

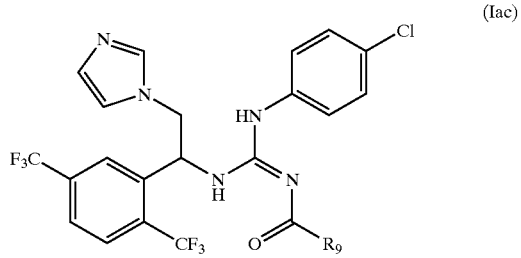

(Iac)

Compounds having the formula (Iac) wherein R₉ has the values listed in Table 24 were prepared following the same or similar procedure as Example 390, except the ethylamine used was 1-(2,5-Bistrifuoromethylphenyl)-2-(imidazol-2-yl)ethylamine and different ureas were used instead of isoniconamide.

TABLE 24

| Example # | R₉ | Appearance | Characterization |
|---|---|---|---|
| 449 | 2,2-dimethylbutyl | White solid | MS 574 |

TABLE 24-continued

| Example # | R₉ | Appearance | Characterization |
|---|---|---|---|
| 450 | tert-butyl | White solid | MS 560 |
| 451 | cyclopropyl | Colorless oil | MS 544 |
| 452 | 1-methylcyclopropyl | Yellow oil | MS 558 |
| 453 | cyclopentylmethyl | White solid | MS 586 |
| 454 | cyclopentyl | White solid | MS 572 |
| 455 | 2,2-dichloro-1-methylcyclopropyl | Yellow oil | MS 626 |
| 456 | 1,1-dimethyl-2-hydroxyethyl | Yellow oil | MS 576 |

EXAMPLES 457–480

N-[1-(2,4-Dichlorophenyl)-2-(benzimidazol-1 yl)-ethyl]-N'-(4-Chlorophenyl)-N''-(Substituted) carbonylguanidines

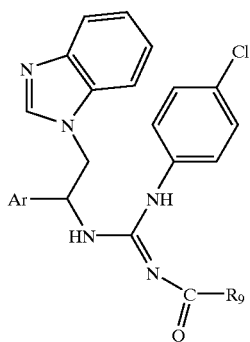

(Iad)

Compounds having the formula (Iad) wherein the phenyl group Ar and R₉ have the values listed in Table 25 were prepared following the same or similar procedure as Example 390, except instead of isoniconamide, different ureas were used, and and the ethylamines used were different 1-(Dihalosubstitutedphenyl)-2-(benzimidazol-1-yl) ethylamines.

TABLE 25

| Example # | Ar | R₉ | Data |
|---|---|---|---|
| 457 | 2,4-dichlorophenyl | 1,1-dichloro-2-methylcyclopropyl | MS 608 |
| 458 | 2,4-dichlorophenyl | 1,1-dimethylpropyl | MS 556 |
| 459 | 2,4-dichlorophenyl | 1,1-dimethyl-2-hydroxyethyl | MS 558 |
| 460 | 2,4-dichlorophenyl | tert-butyl | MS 542 |
| 461 | 2,4-dichlorophenyl | cyclopentylmethyl | MS 568 |
| 462 | 2,4-dichlorophenyl | 1-methylcyclopropyl | MS 540 |
| 463 | 2,4-dichlorophenyl | cyclopropyl | MS 526 |

TABLE 25-continued

| Example # | Ar | R₉ | Data |
|---|---|---|---|
| 464 | 2,4-diCl-phenyl | 4-methoxyphenyl | MS 592 |
| 465 | 2,4-diCl-phenyl | 3-methoxyphenyl | MS 592 |
| 466 | 2,4-diCl-phenyl | 2-methoxyphenyl | MS 592 |
| 467 | 2,4-diF-phenyl | 3-cyanophenyl | MS 555 |
| 468 | 2,4-diF-phenyl | CF₃CF₂– | MS 522 |
| 469 | 2,4-diF-phenyl | 2,2-dimethylbutyl | MS 524 |
| 470 | 2,4-diF-phenyl | 2,2-dimethyl-3-hydroxypropyl | MS 525 |
| 471 | 2,4-diF-phenyl | tert-butyl | MS 509 |
| 472 | 2,4-diF-phenyl | hexafluoro-2-hydroxyisopropyl | MS 619 |
| 473 | 2,4-diF-phenyl | 1-cyanocyclopropyl | MS 518 |
| 474 | 2,4-diF-phenyl | 2,2-dichloro-1-methylcyclopropyl | MS 576 |
| 475 | 2,4-diF-phenyl | cyclopentylmethyl | MS 536 |
| 476 | 2,4-diF-phenyl | 1-methylcyclopropyl | MS 507 |
| 477 | 2,4-diF-phenyl | cyclopropyl | MS 493 |

TABLE 25-continued

| Example # | Ar | R₉ | Data |
|---|---|---|---|
| 478 | 2,4-difluorophenyl | 4-methoxyphenyl (H₃CO) | MS 560 |
| 479 | 2,4-difluorophenyl | 3-methoxyphenyl (OCH₃) | MS 560 |
| 480 | 2,4-difluorophenyl | 2-methoxyphenyl (OCH₃) | MS 560 |

EXAMPLES 481–490

N-[1-(2,4-Dichlorophenyl)-2-(imidazol-1 yl)-ethyl]-N'-(Substituted benzyl)-N"-(Substituted) carbonylguanidines (Iae)

Compounds having the formula (Iae) wherein $R_{21}$ and $R_9$ have the values listed in Table 26 were prepared following the same or similar procedure as Example 390, except instead of isoniconamide different ureas were used, and instead of 4-chlorophenylthioisocyante, different benzyl-isothiocyanates were used.

TABLE 26

| Example # | R₂₁ | R₉ | Appearance | Characterization |
|---|---|---|---|---|
| 481 | 4-chlorophenyl | 1,1-dichloro-2,2-dimethylcyclopropyl | Colorless oil | MS 572 |
| 482 | 4-chlorophenyl | tert-pentyl | Colorless oil | MS 520 |
| 483 | 4-chlorophenyl | cyclobutyl | Colorless oil | MS 504 |

TABLE 26-continued
| Example # | R21 | R9 | Appearance | Characterization |
|---|---|---|---|---|
| 484 | 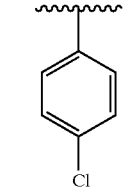 | 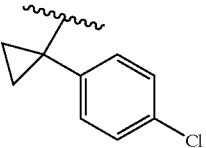 | Colorless oil | MS 600 |
| 485 | 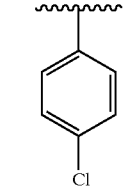 | 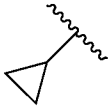 | Colorless oil | MS 490 |
| 486 | 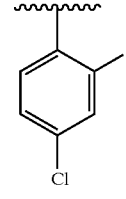 | 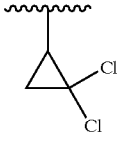 | Colorless oil | MS 591 |
| 487 | 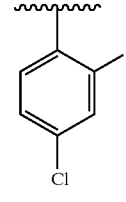 | 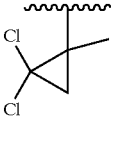 | White solid | MS 606; $^1$H NMR (500 MHz, MeOD) δ 1.3–1.4 (1H, m), 1.51 (3H, d, J = 15.0 Hz), 2.16 (1H, d, J = 10.0 Hz), 4.4–4.8 (4H, m), 6.0–6.3 (1H, m), 7.0–7.3 (2H, m), 7.3–7.7 (7H, m), 8.96 (1H, s). |
| 488 | 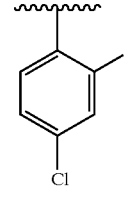 |  | Colorless oil | MS 538 |
| 489 | 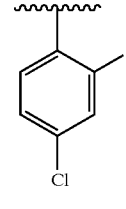 | 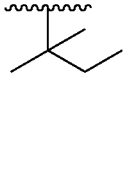 | White solid | MS 554 |
| 490 | 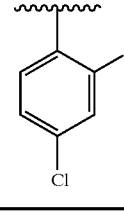 | 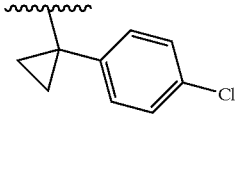 | White solid | MS 634 |

117

N-[1-(2,4-Dichlorophenyl)-2-(imidazol-1-yl)-ethyl]-
N'-(4-chlorophenyl)-N''-(4-tert-Butylphenyl)
sulfonylguanidine

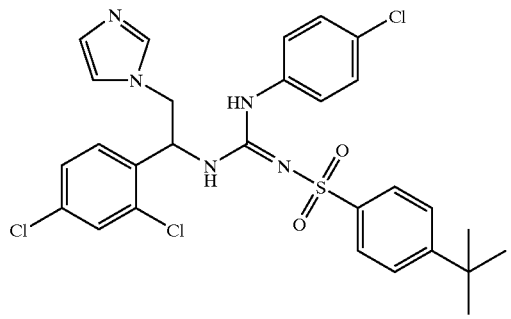

A. 4-tert-Butylphenylsulphonylamine.

To a 500-mL round-bottomed flask was added (4-tert-butylphenyl) sulfonyl chloride (2.30 g, 10.0 mmol) in 100 mL CH$_2$Cl$_2$ at 0° C. and then concentrated NH$_4$OH (50 mL, 100 mmol, 10 equiv). The mixture was allowed to warm to rt and stirred for 20 h. The solvent was evaporated under diminished pressure and the remaining slurry was filtered by Büchner funnel, giving 1.60 g (75%) of Compound A as a white solid.

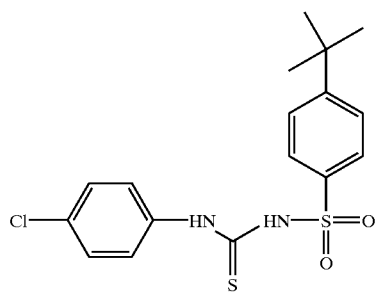

B.

To 1.60 g of Compound A in 30 mL DMF at 0° C. in a 250-mL round-bottomed flask was added NaH (0.72 g, 25 mmol, 3.5 equiv). This mixture was allowed to stir at 0° C. for 30 min and then p-chlorophenylisothiocyanate (1.70 g, 10 mmol, 1 equiv) was added. The mixture was slowly warmed to rt over 24 h. The mixture was poured into ice-water and the solution acidified to pH 2. The precipitate was collected to give 2.76 g (72%) of Compound B as a white solid.

C. Example 491. To a stirred solution of compound B (1.91 g, 5 mmol) in DMF was added 1-(2,4-dichlorophenyl)-2-imidazol-1-yl)ethylamine (1.35 g, 5 mmol, 1 equiv), followed by 1 mL diisopropylethylamine. The mixture was allowed to stir at rt for 15 min, and then HgCl$_2$ was added (2 g, 7.5 mmol, 1.5 equiv). After stirring at rt for 20 h, the mixture was poured into 1N HCl solution, and then filtered by Buchner funnel. The aqueous solution was neutralized to pH 9–10, extracted with EtOAc, and then purified using preparative HPLC, giving 2.0 g (63%) of Example 491 as a white solid. $^1$H NMR (400 MHz, MeOD) δ 1.30 (9H, s), 4.63 (2H, d, J=8.0 Hz), 5.7 (1H, m), 6.98 (2H, d, J=8.0 Hz), 7.4–7.6 (11H, m), 8.9 (1H, s). MS (ES): m/z 604 [M+H]$^+$.

118

EXAMPLE 492

N-[1-(2,4-Dichlorophenyl)-2-(imidazol-1-yl)-ethyl]-
N'-(4-chlorophenyl)-N''-isopropylsulfonylguanidine.

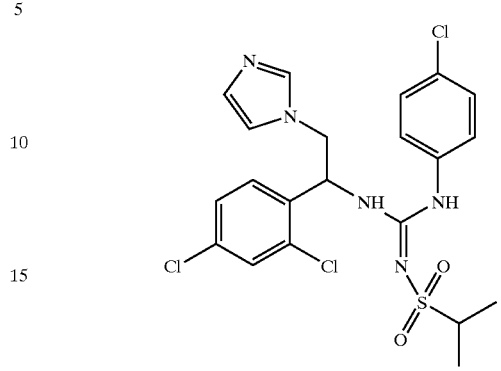

The same procedure of Example 491 was followed, except in step A, t-butyl sulfonyl chloride was used in place of 4-(t-butyl)phenyl sulfonyl chloride to give 50% yield of Example 492 as a white solid. $^1$H NMR (400 MHz, MeOD) δ 1.15 (6H, d, J=4.0 Hz), 2.98 (1H, m), 4.60 (2H, d, J=4.0 Hz), 5.82 (1H, t, J=4.0 Hz), 7.13 (2H, d, J=8.0 Hz, 7.4–7.6 (7H, m), 8.91 (1H, s). MS (ES): m/z 514 [M+H]$^+$.

EXAMPLE 493

N-[1-(2,4-Dichlorophenyl)]-N'-[1-(2,5-bistrifluoromethylphenyl)-2-(benzimidazol-2-yl)-ethyl]-N'''-cyanoguanidine.

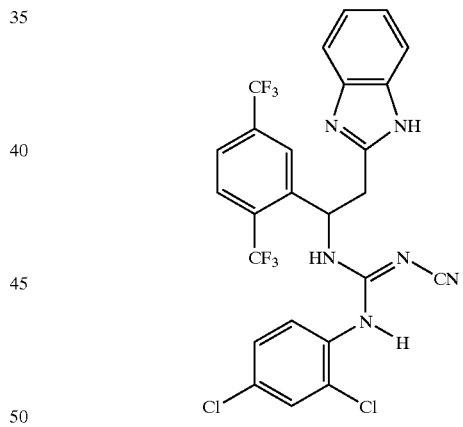

A. 1-[2,5-Bis(trifluromethyl)phenyl]-2-(benzimidazol-2-yl)-ethylamine.

To a flame-dried 200-mL round-bottomed flask containing hexamethyldisilazane (2.91 mL, 13.8 mmol, 1.11 equiv) in 13 mL THF at 0° C. was added n-butyllithium (5.20 mL of a 2.5 M solution in hexanes, 13.0 mmol, 0.95 equiv). After 10 minutes, 2,5-bis-(trifluoromethyl)benzaldehyde (3.00 g, 12.4 mmol) was added as a solution in 5 mL THF. After 5 minutes, chlorotrimethylsilane (1.73 mL, 13.6 mmol, 1.10 equiv) was added, and the mixture was allowed to stir at 0° C. for an additional 20 minutes. During this time, to a separate flame-dried 200-mL round-bottomed flask containing 2-methylbenzimidazole (1.63 g, 12.3 mmol, 1.05 equiv) in 45 mL THF at 0° C. was added n-butyllithium (9.91 mL of a 2.5 M solution in hexanes, 24.8 mmol, 2.00 equiv), and the mixture was stirred 20 minutes. To the N-silylimine generated in the first flask was then added BF$_3$.OEt$_2$ (1.65 mL, 12.4 mmol, 1.00 equiv) all at once, followed by the dianion of 2-methylbenzimidazole generated in the second flask (transferred via cannula). The combined reaction mixture was then allowed to stir, warming to rt overnight. The mixture was then poured into a 500-mL separatory funnel containing 100 mL saturated NH$_4$Cl solution, and the resultant biphasic mixture was extracted with CHCl$_3$ (2×100 mL). The combined organics were washed with 100 mL brine, dried over Na$_2$SO$_4$, and concentrated under reduced pressure. Purification by flash chromatography (silica gel, 10% MeOH in CH$_2$Cl$_2$) provided 1.61 g (35%) of the desired benzylic amine as an off-white solid. HPLC: 97% at 2.12 min (retention time) (YMC ODSA column 4.6×50 mm eluting with 10–90% aqueous MeOH over 4 min containing 0.1% TFA, 4 mL/min, monitoring at 220 nm) MS (ES): m/z 374 [M+H]$^+$.

B. N-[1-(2,4-Dichlorophenyl)]-N'-[1-(2,5-bistrifluoromethylphenyl)-2-(benzimidazol-2-yl)-ethyl]-N''-cyanoguanidine.

This compound was prepared from 1-[2,5-bis(trifluromethyl)phenyl]-2-(benzimidazol-2-yl)-ethylamine and N-cyano-N'-(2,4-dichlorophenyl)thiourea in a manner similar to that previously described for Example 1. HPLC: 99% at 1.75 min (retention time) (YMC S5 ODS column 4.6×33 mm eluting with 10–90% aqueous MeOH over 2 min containing 0.1% TFA, 4 mL/min, monitoring at 220 nm) MS (ES): m/z 585 M+.

EXAMPLE 494

N-[1-(4-Chlorophenyl)]-N'-[1-(2,5-bistrifluoromethylphenyl)-2-(benzimidazol-2-yl)-ethyl]-N''-cyanoguanidine

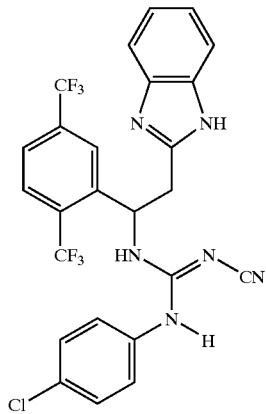

Example 494 was prepared from 1-[2,5-bis(trifluromethyl)phenyl]-2-(benzimidazol-2-yl)-ethylamine and N-cyano-N'-(4-chlorophenyl)thiourea in a manner similar to that previously described for Example 1, providing the desired cyanoguanidine as an off-white solid. HPLC: 99% at 3.16 min (retention time) (YMC ODSA column 4.6×50 mm eluting with 10–90% aqueous MeOH over 4 min containing 0.1% TFA, 4 mL/min, monitoring at 220 nm) MS (ES): m/z 551 [M+H]$^+$.

We claim:
1. A compound having the formula (I):

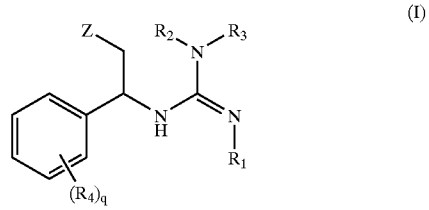

or a pharmaceutically-acceptable salt or hydrate, thereof, wherein:

R$_1$ is cyano, —SO$_2$R$_8$, —C(=O)R$_9$, or heteroaryl;

R$_2$ is (i) independently hydrogen, alkyl, or substituted alkyl, or (ii) taken together with R$_3$ forms a heterocyclo;

R$_3$ is (i) independently alkyl, substituted alkyl, alkylthio, aminoalkyl, carbamyl, A-aryl, A-heterocyclo, A-heteroaryl, or A-cycloalkyl, or (ii) taken together with R$_2$ forms a heterocyclo;

Z is heteroaryl provided that when R$_1$ is cyano, Z is not 2-pyridinyl;

A is a bond, C$_{1-4}$alkylene, C$_{2-4}$alkenylene, substituted C$_{1-4}$alkylene, substituted C$_{2-4}$alkenylene, —C(=O)NR$_{19}$—, —C$_{1-4}$alkylene-C(=O)NR$_{19}$—, or substituted C$_{1-4}$alkylene-C(=O)NR$_{19}$—:

R$_4$ at each occurence is selected independently of each other R$_4$ from the group consisting of halogen, alkyl, substituted akyl, haloalkyl, nitro, cyano, haloalkoxy, OR$_{25}$, SR$_{25}$, NR$_{25}$R$_{26}$, NR$_{25}$SO$_2$R$_{27}$, SO$_2$R$_{27}$, SO$_2$NR$_{25}$R$_{26}$, CO$_2$R$_{26}$, C(=O)R$_{26}$, C(=O)NR$_{25}$R$_{26}$, OC(=O)R$_{25}$, —OC(=O)NR$_{25}$R$_{26}$, NR$_{25}$C(=O)R$_{26}$, NR$_{25}$CO$_2$R$_{26}$, aryl, heteroaryl, heterocyclo and cycloalkyl;

R$_9$ is —NR$_{10}$R$_{11}$, alkyl, substituted alkyl, alkoxy, alkylthio, cyoloalkyl, aryl, heteroaryl, heterocyclo, or —CO$_2$R$_{12}$;

R$_{10}$ and R$_{11}$ are (i) independently selected from hydrogen, alkyl, substituted alkyl, alkoxy, heterocyclo, cycloalkyl, aryl, and heteroaryl;or (ii) taken together form a heterocyclo or heteroaryl;

R$_{12}$ and R$_{19}$ are hydrogen or alkyl;

R$_{25}$ and R$_{26}$ are independently selected from hydrogen, alkyl, or substitizted alkyl, or taken together form a heterocyclo or heteroaryl ring;

R$_{27}$ is alkyl or substituted alkyl, and q is 0, 1, 2, or 3.

2. The compound of claim 1, or a pharmaceutically-acceptable salt or hydrate, thereof, in which Z is an optionally-substituted bicyclic heteroaryl.

3. The compound of claim 1, or a pharmaceutically-acceptable salt or hydrate, thereof, in which:

Z is triazolyl optionally substituted with one to two R$_7$ or imidazolyl optioiially substituted with one to two R$_7$ and/or having fused thereto a benzene ring in turn optionally substituted with one to two R$_7$; and R$_7$is alkyl, carbamyl, or substituted alkyl.

4. The compound of claim 1, or a pharmaceutically-acceptable salt or hydrate, thereof, in which R$_1$ is cyano or —C(=O)R$_9$.

5. The compound of claim 1 or a pharmaceutically-acceptabl salt or hydrate, thereof, in which $R_1$ is cyano, —$SO_2R_8$, —C(=O)$R_9$, or thiazolyl;

$R_8$ is $C_{1-4}$alkyl or phenyl optionally substituted with alkyl, halogen, haloalkoxy, cyano, nitro, or trifluoromethyl;

$R_9$ is a) $NR_{10}R_{11}$;
  b) $C_{1-4}$alkyl optionally substituted with one to two of:
    i) $SR_{13}$, $OR_{13}$, $NR_{13a}R_{13b}$, halogen, trifluoromethyl, $CO_2R_{13a}$, and C(=O)$NR_{13a}R_{13b}$;
    ii) cycloalkyl optionally substituted with one to two of C(=O)H, $C_{1-4}$acyl, alkenyl, carbamyl, and/or phenyl in turn optionally substituted with halogen;
    iii) phenyl or napthyl optionally substituted with one to two of halogen, nitro, amino, alkyl, hydroxy, $C_{1-4}$alkoxy, or having fused thereto a five or six membered heterocyclo;
    iv) pyridinyl, thiophenyl, furanyl, tetrahydrofuranyl, or azepinyl, optionally substituted with alkyl or having fused thereto a five to six membered carbocyclic ring optionally substituted with keto or $C_{1-4}$alkoxy;
  c) $C_{1-4}$alkoxy;
  d) $C_{1-4}$alkylthio;
  e) $CO_2$alkyl;
  i) 3 to 6 membered cycloalkyl optionally having up to four substituetits selected from alkyl, halogen, cyano, alkenyl, acyl, alkylthio, carbamyl, phenyl in turn optionally substituted with halogen; or having an aryl fused thereto;
  g) pheuyl optionally substituted with one to four of halogen, cyano, trifluoromethyl, nitro, hydroxy, $C_{1-4}$alkoxy, haloalkoxy, $C_{1-4}$alkyl, $CO_2$alkyl, $SO_2$alkyl, $SO_2NH_2$, amino NH($C_{1-4}$alkyl), N($C_{1-4}$alkyl)$_2$, NHC(=O)alkyl, C(=O)alkyl, and/or $C_{1-4}$alkyl optionally substituted with one to three of trifluoromethyl, hydroxy, cyano, phenyl, pyridinyl; and/or a five or six membejed heteroaryl or heterocyle in turn optionally substituted with keto or having a benzene ring fused thereto;
  h) pyridinyl, thiazolyl, furanyl, thiophenyl, and pyrrolyl optionally substituted with one to two of halogen, alkyl, and phenyl in turn optionally substituted with halogen or trifluoromethyl;

$R_{10}$ and $R_{11}$ are
  a) independently selected from:
    i) hydrogen, $C_{1-4}$alkoxy, heterocyolo, cycloalkyl, aryl, and heteroaryl; and
    ii) $C_{1-4}$alkyl optionally substituted with one to two of —$CO_2$alkyl, —C(=O)NH(aryl), NH(aryl), cycloalkyl, phenyloxy, phenyl in turn optionally substituted with $C_{1-4}$alkyl, hydroxy, $C_{1-4}$alkoxy, halogen, amino, nitro, tetrahydrofuranyl, and/or five or six incrnbered heterocyclo, or having a five or six membered heterocyclo fused thereto; pyrrolidinyl optionally substituted with keto; napthyl, anthracenyl, pyridinyl, thiophenyl, furanyl, imidazolyl, benzimidazolyl, or indolyl in turn optionally substituted with $C_{1-4}$alkyl or $C_{1-4}$alkoxy; or
  b) $R_{10}$ and $R_{11}$ taken together form a heterocyclo selected from pyrrolidinyl, piperazinyl, piperidinyl, morpholinyl, tetrahydropyridinyl, and imidazoilidinyl, wherein said heterocyclo formed by $R_{10}$ and $R_{11}$ is optionally substisduted with one to two of keto, $CO_2H$, $C_{1-4}$alkoxy, $CO_2$alkyl, $C_{1-4}$carbamyl, benzyl; phenyl in turn optionally substituted with alkyl, halogen, or $C_{1-4}$ alkoxy; tetrahydropyridinyl in turn optionally substituited with keto and/or phenyl; alkyl optionally substituted with amino or $NHR_{21}$ wherein $R_{21}$ is alkyl or phenyl optionally substituted with alkyl; and/or has a benzene ring fused thereto in turn optionally substituted with one to two of alkyl, $C_{1-4}$alkoxy, $CO_2$alkyl, and/or $C_{1-4}$carbamyl;

$R_{13}$ is hydrogen or alkyl; and $R_{3a}$ and $R_{13b}$ are selected from hydrogen, alkyl, and aryl.

6. The compound of claim 1, or a pharmaceutically-acceptable salt or hydrate, thereof, in which $R_2$ is (i) independently hydrogen, alkyl, or substituted alkyl, or (ii) taken together with $R_3$ forms a heterocyclo optionally substituted with alkyl or substituted alkyl;

$R_3$ is (i) independently selected from $C_{1-4}$alkyl, alkylthio, aminoalkyl, -A-aryl, -A-heterocyclo, -A-cycloalkyl, and -A-hetaroaryl, optionally having one to three substituents selected from $R_{3a}$; and/or having fused thereto a five or six membered carbocyclic ring, or (ii) taken together with $R_2$ forms a heterocyclo optionally substituted with alkyl or substituted alkyl;

$R_{3a}$ at each occurrence is selected independently from alkyl, substituted alkyl, halogen, haloalkoxy, cyano, nitro, keto, trifluoromethyl, —$NR_{17}R_{18}$, —$SR_{17}$, —$OR_{17}$, —$SO_2R_{17a}$, —$SO_2NR_{17}R_{18}$, —$NR_{17}$C(=O)$R_{18}$, —$CO_2R_{17}$, —C(=O)$R_{17}$, cyoloalkyl, aryl, heterocyolo, and heteroaryl, wherein when $R_{3a}$ is cycloalkyl, aryl, heterocyclo or heteroaryl, said cycloalkyl, aryl, heterocyolo and heteroaryl in turn is optionally substituted with alkyl or substituted alkyl;

A is a bond, $C_{1-4}$alkylene, substituted $C_{1-4}$alkylene, —C(=O)NH—, —$C_{1-4}$alkylene-C(=O)NH—, or substituted $C_{1-4}$alkylene-C(=O)NH—;

$R_{17}$ and $R_{18}$ are independently selected from hydrogen, alkyl, substituted alkyl, and aryl; and $R_{17a}$ is alkyl or substituted alkyl.

7. The compound of claim 6, or a pharmaceutically-acceptable salt or hydrate, thereof, in which A is —(CHR$_{14}$)$_m$—(CR$_{15}$R$_{16}$)$_n$— or —(CHR$_{14}$)$_p$—C(=O)NH—;

$R_{14}$, $R_{15}$ and $R_{16}$ at each occurrence are independently selected from hydrogen, alkyl, hydroxy, hydroxyC$_{1-4}$alkyl, $C_{1-4}$alkoxy, and phenyl, and/or one of $R_{15}$ and one of $R_{16}$ join together to form a 3 to 6 membered cycloalkyl;

m and n are 0, 1 or 2; and is 0, 1, 2, or 3.

8. The compound of claim 6, or a pharmaceutially-acceptable salt or hydrate, thereof, in which $R_{17}$ and $R_{18}$ are independently selected from hydrogen, alkyl, phenyl, or benzyl wherein the phenyl or beazyl is optionally substituted with alkyl, hydroxy, or hydroxyalkyl.

9. The cornpoimd of claim 1, or a pharmaceutically-aeceptable salt or hydrate, thereof, in which $R_1$ cyano;

$R_2$ is hydrogen, alkyl, or benzyl;

$R_3$ is phenyl optionally substituted with $C_{1-4}$alkyl, halogen, mfluoromethyl, OCF$_3$, cyano, nitro, amino, hydroxy, or methoxy; and $R_4$ is halogen, alkyl, trifluoromethyl, or OCF$_3$.

10. The compound of claim 1, or a pharmaceutically-acceptable salt or hydrate, thereof, in which $R_1$ is C(=O)$R_9$;

$R_2$ is hydrogen, alkyl, or benzyl;

$R_3$ is phenyl optionally substituted with $C_{1-4}$alkyl, halogen, trifluoromethyl, OCF$_3$, cyano, nitro, amino, hydroxy, or methoxy;

$R_4$ is halogen, alkyl, trifluoromethyl, or $OCF_3$; and $R_9$ is $—NR_{10}R_{11}$, alkyl or phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, $NH(C_{1-4}$alkyl), $N(C_{1-4}$alkyl)$_2$, $NHC(=O)$akly, $C(=O)$alkyl, and/or $C_{1-4}$alkyl optionally substituted with one to three of trifluoromethyl, hydroxy, cyano, phenyl, pyridinyl; and/or a five or six membered heteroaryl or heterocylo in turn optionally substituted with keto or having a benzene ring fused thereto.

11. A compound having the formula:

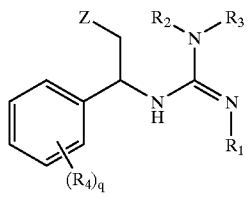

or a pharmaceutically-acceptable salt or hydrate thereof, wherein:

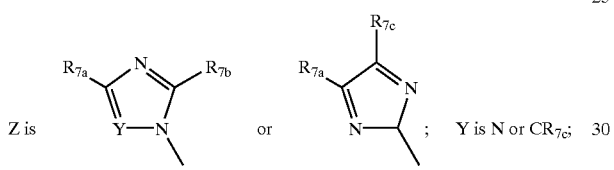

Z is ; Y is N or $CR_{7c}$;

$R_1$ is cyano, $—SO_2R_8$, $—C(=O)R_9$, or heteroaryl;

$R_2$ is (i) independently hydrogen, alkyl, or subititued alkyl, or (ii) taken together with $R_3$ forms a heterocyclo;

$R_3$ is (i) independently selected from
(a) alkyl optionally substituted with one to two of hydroxy and alkoxy;
(b) alkylthio or aminoalkyl optionally substituted with hydroxy or alkoxy;
(c) $-A_1$-aryl, wherein the aryl is optionally substituted with up to four substituents selected from alkyl, substituted alkyl, halogen, haloalkoxy, cyano, nitro, $—NR_{17}R_{18}$, $—SR_{17}$, $—OR_{17}$, $—SO_2R_{17a}$, $—SO_2NR_{17}R_{18}$, $—NR_{17}C(=O)R_{18}$, $—CO_2R_{17}$, $—C(=O)R_{17}$, cycloalkyl, aryl, heterocyclo, and heteroaryl, and/or has fused thereto a five or six membered cycloalkyl ring;
(d) $-A_2$-heteroaryl wherein the heteroaryl is a five or six membered monocyclic ring having 1 to 3 heteroatoms selected from N, O, and S, or an eight or nine membered bicyclic ringed system having at least one aromatic ring and 1 to 4 heteroatoms selected from N, O, and S in at least one of the rings, said heteroaryl being optionally substituted with halogen. alkyl, alkoxycarbonyl, sulfonamide, nitro, cyano, trifluoromethyl, alkylthio, alkoxy, keto, $—C(=O)H$, acyl, benzyloxy, hydroxy, hydroxyalkyl, or phenyl optionally substituted with alkyl or substituted alkyl;
(e) $-A_2$-hoterooyclo wherein the heterocyclo is optionally substituted with one to two groups selected from alkyl, keto, hydroxy, hydroxyalkyl, $—C(=O)H$, acyl, $CO_2H$, alkoxycarbonyl, phenyl, and/or benzyl, and/or has a bridged carbon—carbon chain or fused benzene ring joined thereto;
(f) $-A_2$-cycloalkyl wherein the cycloalkyl is optionally substituted with one to two groups selected from alkyl, keto, $—C(=O)H$, acyl, $CO_2H$, alkoxycarbonyl, and/or benzyl, and/or has a bridged carbon—carbon chain or fused benzene ring joined thereto; or (ii) taken together with $R_2$ forms a heterocyclo;

$R_4$ at each occurrence is selected independently of each other $R_4$ from the group consisting of halogen, alkyl, haloalkyl, intro, cyano, and haloalkoxy;

$R_{7a}$, $R_{7b}$ and $R_{7c}$ are alkyl, carbamyl, or carbamylalkyl, or $R_{7a}$ and $R_{7c}$ join to form an aryl or heteroaryl;

$R_8$ is alkyl, arylalkyl, or aryl;

$R_9$ is alkyl, substituted alkyl, alkoxy, alkylthio, cycloalkyl, aryl, heteroaryl, heterocyclo, or $CO_2R_{12}$;

$R_{10}$ is independently hydrogen, alkyl, or alkoxy; and $R_{11}$ is independently hydrogen, alkyl, substituted alkyl, alkoxy heterocyclo cycloalkyl, aryl, or heteroaryl; or $R_{10}$ and $R_{11}$ taken together form a heterocyclo or heteroaryl optionally substituted with alkyl, keto, $CO_2H$, alkoxycarbonyl, hydroxy, alkoxy, alkyl, carbamyl, aryl, or substituted alkyl, wherein when the $R_{10}$ and $R_{11}$ group comprises a phenyl ring, said phenyl ring is optionally substituted with one to two of alkyl, halogen, and alkoxy;

$R_{12}$ is hydrogen or alkyl;

$A_1$ is $—(CHR_{14})_m—V—(CR_{15}R_{16})_n—$ or $—(CHR_{14})_p—(C=O)NH—$;

$A_2$ is $—(CHR_{14})_m—V—(CR_{15}R_{16})_n$;

V is a bond, S, or $—NR_{22}—$;

$R_{14}$, $R_{15}$ and $R_{16}$ at each occurrence are independently selected from hydrogen, alkyl, hydroxy, hydroxyC$_{1-4}$alkyl, $C_{1-4}$alkoxy, and phenyl, and/or one of $R_{15}$ and one of $R_{16}$ join together to form a three to six membered cycloalkyl;

$R_{17}$ and $R_{18}$ are independently selected from hydrogen, alkyl, pheziyl, and benzyl, wherein the phenyl and benzyl is optionally substituted with alkyl, hydroxy, or hydroxyalkyl;

$R_{17a}$ is alkyl or substituted alkyl;

$R_{22}$ is hydrogen or alkyl;

m and n are 0, 1, 2, or 3;

p is 0, 1, 2, or 3; and q is 0, 1, 2, or 3.

12. The compound of claim 11, or a pharmaceutically-acceptable salt or hydrate, thereof, having the formula:

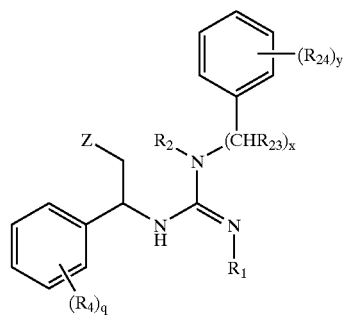

in which $R_{7a}$, $R_{7b}$ and $R_{7c}$ are alkyl, carbamyl or carbamylC$_{1-4}$alkyl, or $R_{7a}$ and $R_{7c}$ join to form a fused phenyl ring;

$R_{23}$ is selected from hydrogen, alkyl, hydroxyulkyl, or phenyl;

$R_{24}$ is selected from alkyl, halogen, trifluoromethyl, cyano, halogen, hydroxy, $OCF_3$, methoxy, phenyloxy, benzyloxy, cyano, acyl, or two $R_{24}$ groups join to form a fused cycloalkyl or benzene ring; and x is 0, 1, or 2; and y is 0, 1, 2, or 3.

13. The compound of claim 12, or a pharmacentically-acceptable salt or hydrate, thereof, in which $R_1$ is cyano or $-C(=O)R_9$.

14. The compound of claim 13, or a pharmacentically-acceptable salt or hydrate, thereof, in which $R_9$ is $-NR_{10}R_{11}$, alkyl or phenyl optionally substituted with one to four of halogen, cyano, trifluoromethyl, nitro, hydroxy, $C_{1-4}$alkoxy, haloalkoxy, $C_{1-6}$alkyl, $CO_2$alkyl, $SO_2$alkyl, $SO_2NH_2$, amino, $NH(C_{1-4}$alkyl), $N(C_{1-4}$alkyl)$_2$, $NHC(=O)$ alkyl, $C(=O)$alkyl, and/or $C_{1-4}$alkyl optionally substituted with one to three of trifluoromethyl, hydroxy, cyano, phenyl, pyridinyl; and/or a five or six membered heteroaryl or heterocyclo in turn optionally substituited with keto or having abenzene ring fused thereto.

15. A non-peptidic organic compound according to claim 1, or a pharmaceutically-acceptable salt or hydrate, thereof, having less than 1000 molecular weight that is effective for inhibiting $F_1F_0$-ATP hydrolase.

16. A compound according to claim 15, or a pharmaceutically-acceptable salt or hydrate thereof; having less than 750 molecular weight.

17. A method of inhibiting $F_1F_0$-ATP hydrolase by administering to a mammal a non-peptidic organic compound according to claim 1, or a pharmaeutically-acceptable salt or hydrate thereof, having less than 1000 molecular weight.

18. The method of claim 17, comprising administering to the mammal the non-peptidic organic compound in combination with a second compound selected from propafenone, propranolol; sotalol, dofetilide, amiodarone, azimilide, ibutilide, ditiazem, verapamil, captopril, lisinopril, zofenopril, ramipril, fosinopril, enalapril, eranopril, cilazopril, delapril, pentopril, quinapril, omapatrilat, gemopatrilat, losartan, irbesartan, valsartan, sitaxsentan, atrsentan;verapamil, nifedipine, diltiazem, amlodipine and mybefradil, digitalis, ouabain, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolatone, aplirinone, dipyridamole, cilostazol, sildenafil, ifetroban, picotamide, ketanserin, clopidogrel, picotamide, rosuvastaitin, atavastatin visastatin, questran, CP-529414, lovenox, enoxaparain dalteparinnadolol, carvedilol, albuterol, terbutaline, formoterol, salmeterol, bitolterol, pilbuterol, fenoterol, ipratropium bromide, metformin, acarbose, repaglinide, glimpepiride, glyburide, glyburide, glipizide, glucovance, troglitazone, rosiglitazone, pioglitazone, GLP-1, nefazodone, sertraline, diazepam, lorazepam, buspirone, hydroxyzine pamoate, acarbose, endostatin, probucol, BO-653, Vitamin A, Vitamin E, AGI-1067, alendronate, raloxifene, orlistate, cyclosperine A, paclitaxel, FK506, adriamycin, famotidine, rapitidine, ompeprazole, estrogen, estradiol, dipyridamole, cilostazol, sildenafil, ketanserin, taxol, cisplatin, paclitaxel, adriamycin, epothilones, carboplatin, cromolyn, nedocromil, theophylline, zileuton, zafirlukast, monteleukast, pranleukast, beclomethasone, triamcinolone, budesonide, fluticasone, flunisolidem prednisone; dexamethasone, etanercept, aspirin, indomethacin, pravastatin, simvastatin, atorvastatin, fluvastatin, cerivastatin, AZ4522, itavastatin, ZD-4522, rosuvastatin, atavastatin, visastatin, abciximab, eptifibatide, tirofiban, clopidogrel, ticlopidine, CS-747, ifetroban, aspirin; cariporide, streptokinase, reteplase, activase, lanoteplase, urokinase, prourokinse, tenecteplase, lanoteplase, anistreplase, eminase, lepirudin, argatroban, XR-330, T686, anti-α-2-antiplasmin antibody, and doesdipyridanmol.

19. A pharmaceutical composition comprising at least one compound of claim 1 and a pharmaceutically-acceptable carrier or diluent.

20. The pharmaceutical composition of claim 19 further comprising at least one additional therapeutic agent selected from one or more of propafenone, propranolol; sotalol, dofetilide, amiodarone, azimilide, ibutilide, ditiazem, verapamil, captopril, lisinopril, zofenopril, ramipril, fosinopril, enalapril, ceranopril, cilazopril, delapril, pentopril, quinapril, omapatrilat, gemopatrilat, losartan, irbesartan, valsartan, sitaxsentan, atrsentan;verapamil, nifedipine, diltiazem, amlodipine and mybefradil, digitalis, ouabain, chlorothiazide, hydrochlorothiazide, flumethiazide, hydroflumethiazide, bendroflumethiazide, methylchlorothiazide, trichloromehtiazide, polythiazide, benztiazide, ethacrynic acid tricrynafen, chlorthalidone, furosemide, musolimine, bumetanide, triamtrenene, amiloride, spironolatone, aplirinone, dipyridamole, cilostazol, sildenafil, ifetroban, picotamide, kentanserin, clopidogrel, picotamide, rosuvastatin, atavastatin visastatin, questran, CP-529414, lovenox, enoxaparain dalteparinnadolol, carvedilol, albuterol, terbutaline, formoterol, salmeterol, bitolterol, pilbuterol, fenoterol, ipratropium bromide, metformin acarbose, repaglinide, glimpepiride, glyburide, glipizide, glucovance, troglitazone, rosiglitazone, pioglitazone, GLP-1, nefazodone, sertraline, diazepam, lorazepam, buspirone, hydroxyzine pamoate, acarbose, endostatin, probucol, BO-653, Vitamin A, Vitamin E, AGI-1067, alendronate, raloxifene, orlistate, cyclosporine A, paclitaxel, FK506, adriamycin, famotidine, ranitidine, ompeprazole, estrogen, estradiol, dipyridamole, cilostazol, sildenafil, ketanserin, taxol, cisplatin, paclitaxel, adriamycin, epothilones, carboplatin, cromolyn, nedocromil, theophylline, zileuton, zafirlukast, monetleulast, pranlikast, beclomthasone, triamcinolone, budesonide, fluticasone, fluticasone, flunisolide, prednisone; dexamethasone; etanercept, aspirin, indomethacin, pravastatin, simvastatin, atorvastatin, fluvastatin, cerivastatin, AZ4522, itavastatin, ZD-4522, rosuvastatin, atavastatin, visastatin, abciximab, eptifibatide, tirofiban, clopidogrel, ticlopidine, CS-747, ifetroban, aspirin; cariporide, streptolinase, reteplase, activase, lanoteplase, urokinase, prourokinse, tepecteplase, lanoteplase, anistreplase, eminase, lepirudin, argatroban, XR-330, T686, anti-α-2-antiplasmin antibody, and doesdipyridanmol.

21. The pharmaceutical composition of claim 20 wherein the additional therapeutic agent is an anti-arrnyhthmic agent selected from sotalol, dofetilide, amiodarone, azimilide, ibutilide, diltiazem, and verapamil.

22. The pharmaceutical composition of claim 20 wherein the additional therapeutic agent is an anti-hypertensive agent selected from captopril, lisinopril, zofenopril, ramipril, fosinopril, enalapril, ceranopril, cilazopril, delapril, pentopril, quinapril, omapatrilat, gemopatrilat, losartan, irbesartan, valsartan; sitaxsentan, and atrsentan.

23. The pharmaceutical composition of claim 20 wherein the at least one additional therapeutic agent is a platelet inhibitor selected from one or more of abciximab, eptifibatide, tirofiban, clopidogrel, ticlopidine, CS-747, ifetroban, and aspirin.

24. A method of treating an ischemic condition comprising administering an effective amount of at least one compound of claim 1 to a patient in need thereof wherein the ischemic condition is an acute coronary syndrome selected from myocardial infarction, congestive heart failure, and cardiac arrhythmias.

25. A method of inhibiting mitochondrial $F_1F_0$ ATP hydrolase activity comprising administering an effective amount of at least one compound of claim 1 to a patient in need thereof.

* * * * *